(12) United States Patent
Rafique et al.

(10) Patent No.: US 10,829,424 B2
(45) Date of Patent: Nov. 10, 2020

(54) OXIDATIVE COUPLING OF METHANE IMPLEMENTATIONS FOR OLEFIN PRODUCTION

(71) Applicant: Lummus Technology LLC, The Woodlands, TX (US)

(72) Inventors: Humera A. Rafique, Dublin, CA (US); Srinivas Vuddagiri, Davis, CA (US); Guido Radaelli, South San Francisco, CA (US); Erik C. Scher, San Francisco, CA (US); Jarod McCormick, San Carlos, CA (US); Joel Cizeron, Redwood City, CA (US)

(73) Assignee: Lummus Technology LLC, The Woodlands, TX (US)

(*) Notice: Subject to any disclaimer, the term of this patent is extended or adjusted under 35 U.S.C. 154(b) by 0 days.

(21) Appl. No.: 16/509,279

(22) Filed: Jul. 11, 2019

(65) Prior Publication Data
US 2020/0216370 A1  Jul. 9, 2020

Related U.S. Application Data

(63) Continuation of application No. 15/076,402, filed on Mar. 21, 2016, now abandoned, which is a
(Continued)

(51) Int. Cl.
*C07C 2/84* (2006.01)
*C07C 1/12* (2006.01)
(Continued)

(52) U.S. Cl.
CPC ............... *C07C 2/84* (2013.01); *B01J 19/245* (2013.01); *B01J 21/04* (2013.01); *B01J 23/00* (2013.01);
(Continued)

(58) Field of Classification Search
CPC .... C07C 2/84; C07C 2/76; C07C 2/78; C07C 2/82; C07C 1/0425; C07C 1/041;
(Continued)

(56) References Cited

U.S. PATENT DOCUMENTS 2,324,172 A   7/1943  Parkhurst
2,486,980 A   11/1949 Robinson
(Continued)

FOREIGN PATENT DOCUMENTS

CA       2041874 C    4/1999
CA       2765769 A1   1/2011
(Continued)

OTHER PUBLICATIONS

Wang, et al. Low temperature selective oxidation of methane to ethane and ethylene over BaCO3/La2 03 catalysts prepared by urea combustion method. Catalysis communications 7: 5963, 2006.
(Continued)

*Primary Examiner* — Ali Z Fadhel
(74) *Attorney, Agent, or Firm* — Calfee, Halter & Griswold LLP

(57) ABSTRACT

The present disclosure provides oxidative coupling of methane (OCM) systems for small scale and world scale production of olefins. An OCM system may comprise an OCM subsystem that generates a product stream comprising $C_{2+}$ compounds and non-$C_{2+}$ impurities from methane and an oxidizing agent. At least one separations subsystem downstream of, and fluidically coupled to, the OCM subsystem can be used to separate the non-$C_{2+}$ impurities from the $C_{2+}$ compounds. A methanation subsystem downstream and fluidically coupled to the OCM subsystem can be used to react $H_2$ with CO and/or $CO_2$ in the non-$C_{2+}$ impurities to generate methane, which can be recycled to the OCM subsystem. The OCM system can be integrated in a non-OCM
(Continued)

system, such as a natural gas liquids system or an existing ethylene cracker.

18 Claims, 34 Drawing Sheets

Related U.S. Application Data continuation of application No. 14/789,946, filed on Jul. 1, 2015, now Pat. No. 9,352,295, which is a continuation of application No. 14/592,668, filed on Jan. 8, 2015, now Pat. No. 9,701,597.

(60) Provisional application No. 62/086,650, filed on Dec. 2, 2014, provisional application No. 62/073,478, filed on Oct. 31, 2014, provisional application No. 62/050,720, filed on Sep. 15, 2014, provisional application No. 61/996,789, filed on May 14, 2014, provisional application No. 61/955,112, filed on Mar. 18, 2014, provisional application No. 61/925,627, filed on Jan. 9, 2014.

(51) Int. Cl.
| | |
|---|---|
| *C07C 1/04* | (2006.01) |
| *B01J 21/04* | (2006.01) |
| *B01J 23/46* | (2006.01) |
| *B01J 23/755* | (2006.01) |
| *B01J 35/00* | (2006.01) |
| *B01J 35/06* | (2006.01) |
| *B01J 19/24* | (2006.01) |
| *C07C 5/327* | (2006.01) |
| *C07C 4/02* | (2006.01) |
| *B01J 23/00* | (2006.01) |
| *C07C 2/78* | (2006.01) |
| *C07C 2/76* | (2006.01) |
| *C07C 2/82* | (2006.01) |

(52) U.S. Cl.
CPC ........... *B01J 23/462* (2013.01); *B01J 23/755* (2013.01); *B01J 35/0013* (2013.01); *B01J 35/06* (2013.01); *C07C 1/041* (2013.01); *C07C 1/0425* (2013.01); *C07C 1/0485* (2013.01); *C07C 1/12* (2013.01); *C07C 2/76* (2013.01); *C07C 2/78* (2013.01); *C07C 2/82* (2013.01); *C07C 4/02* (2013.01); *C07C 5/327* (2013.01); *B01J 2219/00006* (2013.01); *B01J 2219/00074* (2013.01); *B01J 2219/24* (2013.01); *Y02P 20/121* (2015.11); *Y02P 20/123* (2015.11); *Y02P 20/124* (2015.11); *Y02P 20/126* (2015.11); *Y02P 20/52* (2015.11); *Y02P 20/572* (2015.11)

(58) Field of Classification Search
CPC .. C07C 5/327; C07C 4/02; C07C 1/12; C07C 1/0485; B01J 35/06; B01J 21/04; B01J 23/00; B01J 35/0013; B01J 23/462; B01J 23/755; B01J 19/245; B01J 2219/24; B01J 2219/00074; B01J 2219/00006; Y02P 20/124; Y02P 20/121; Y02P 20/52; Y02P 20/126; Y02P 20/123; Y02P 20/572
See application file for complete search history.

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,584,071 A | 6/1971 | McNulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood |
| 4,481,305 A | 11/1984 | Jorn et al. |
| 4,489,215 A | 12/1984 | Withers |
| 4,511,747 A | 4/1985 | Wright et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,882,400 A | 11/1989 | Dumain et al. |
| 4,891,457 A | 1/1990 | Owen et al. |
| 4,895,823 A | 1/1990 | Kolts et al. |
| 4,900,347 A | 2/1990 | McCue, Jr. et al. |

(56) References Cited

U.S. PATENT DOCUMENTS

| | | |
|---|---|---|
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hutton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |

(56) References Cited

U.S. PATENT DOCUMENTS

| | | |
|---|---|---|
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |

(56) References Cited

U.S. PATENT DOCUMENTS

| | | |
|---|---|---|
| 2008/0141713 A1 | 6/2008 | Verma |
| 2008/0154078 A1 | 6/2008 | Bozzano et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1* | 1/2014 | Iyer .................. C10G 57/00 585/302 |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |

(56) References Cited

U.S. PATENT DOCUMENTS

| | | |
|---|---|---|
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Wang, et al., Critical Influence of BaCO3 on Low Temperature Catalytic Activity of BaCO3/Zr02 Catalysts for Oxidative Coupling of Methane, Catalysis Letters (2009), 129:156-162.

Water Electrolysis & Renewable Energy Systems. FuelCellToday (May 2013).

Wikipedia search, Adiabatic Process, Mar. 2011, 10 pages.

Witek-Krowiak, A. et al. Carbon Dioxide Removal in a Membrane Contactor-Selection of Absorptive Liquid/Membrane System. Intl J Chem Eng and Appl. (2012) 3(6):391-395.

Wong, et al. Oxidative coupling of methane over alkali metal oxide promoted La2 03/BaCO3 catalysts. J. Chem. Tech. Biotechnol. 65:351-354, 1996.

Wu, et al., High-Capacity Methane Storage in Metal-Organic Frameworks M2(dhtp): The Important Role of Open Metal Sites, J. Am. Chem. Soc. 131 (13):4995-5000.

Xu, et al. Maximise ethylene gain and acetylene selective hydrogenation efficiency. Petroleum technology quarterly 18.3 (2013): 39-42.

Xu, G. et al. An Improved CO2 Separation and Purification System Based on Cryogenic Separation and Distillation Theory. Energies (2014) 7:3484-3502.

Yan, D. Modeling and Application of a Thermoelectric Generator. Thesis, Univ. Toronto (2011).

Yang, et al. Anistropic synthesis of boat shaped core shell Au—Ag nanocrystals and nanowires. Nanotechnology 17: 2304-2310, 2006.

Yu, et al. Oxidative coupling of methane over acceptor-doped SrTi 03: Correlation between p-type conductivity and 2,2 selectivity and C2 yield. Journal of Catalysis. 13 (5): 338-344, 1992.

Zhang, Q. Journal of Natural Gas Chem., 12:81, 2003.

(56) References Cited

OTHER PUBLICATIONS

Zhao, et al. Technologies and catalysts for catalytic preparation of ethene. Industrial catalysis 12 (Supplement): 285-289, 2004.
Zhou, et al. Functionalization of lanthanum hydroxide nanowires by atom transfer radical polymerization. Nanotechnology 18, 2007, 7 pages.
Zhou. BP-UOP Cyclar Process. Handbook of Petroleum Refining Processes, The McGraw-Hill Companies (2004), pp. 2.29-2.38.
Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
U.S. Appl. No. 62/073,478, filed Oct. 31, 2014.
International search report and written opinion dated Jun. 12, 2015 for PCT Application No. PCT/US2015/010688.
International preliminary report on patentability dated Jul. 21, 2016 for PCT. Application No. PCT/US2015/010688.
Office action dated Dec. 23, 2016 for U.S. Appl. No. 14/592,668.
Notice of allowance dated May 16, 2017 for U.S. Appl. No. 14/592,668.
Office action dated Sep. 11, 2015 for U.S. Appl. No. 14/789,946.
Notice of allowance dated Jan. 13, 2016 for U.S. Appl. No. 14/789,946.
Office action dated Oct. 4, 2016 for U.S. Appl. No. 15/076,402.
Office action dated Apr. 22, 2016 for U.S. Appl. No. 15/076,402.
Office action dated Jul. 21, 2017 for U.S. Appl. No. 15/076,402.
U.S. Appl. No. 15/076,402 Office Action dated Mar. 8, 2018.
U.S. Appl. No. 15/076,402 Office Action dated Jan. 11, 2019.
U.S. Appl. No. 15/888,777 Office Action dated Apr. 26, 2018.
U.S. Appl. No. 15/888,777 Office Action dated Nov. 5, 2018.
U.S. Appl. No. 16/021,441 Office Action dated Aug. 28, 2018.
U.S. Appl. No. 16/021,441 Notice of Allowance dated Nov. 21, 2018.
Extended European search report and opinion dated Jul. 19, 2017 for EP Application No. 15734911.9.
Communication pursuant to Article 94(3) dated Feb. 12, 2020 for EP Application No. 15734911.9.
Examination Report No. 1 dated Aug. 1, 2018 for AU Application No. 2015204709.
Notice of Acceptance dated Aug. 6, 2019 for AU Application No. 2015204709.
Office Action dated May 15, 2020 for U.S. Appl. No. 16/538,012.
Agarwal, et al., Aqueous Au—Pd colloids catalyze selective CH4 oxidation to CH3OH with O2 under mild conditions, Science 358, Oct. 13, 2017, 223-27.
Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.
American Petroleum Institute Publication 534 Heat Recovery Steam Generators Jan. 1995 (51 pages).
Autothermal Partial Oxidative Coupling of Methane. IP.com, Prior Art Database Technical Disclosure, Jul. 29, 2008, 5 pages.
Barrett, et al. The determination of pore volume and area distributions in porous substances—Compuatations from nitrogen isotherms. J. Am. Chem. Soc., 1951, vol. 73, pp. 373-380.
Berstad, D. et al. Low-temperature CO2 removal from natural gas. Energy Procedia (2012) 26:41-48.
Bloch, et al. Hydrocarbon Separations in a Metal-Organic Framework with Open Iron(II) Coordination Sites, Science, 2012, 335:1606-1610.
Bollmann, et al. Ethylene tetramerization: a new route to produce 1-octene in exceptionally high selectivities. J Am Chem Soc. Nov. 17, 2004;126(45):14712-3.

Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.
Carter, et al. High activity ethylene trimerisation catalysts based on diphosphine ligands. Chem Commun (Camb). Apr. 21, 2002;(8):858-9.
Caskey, et al., Dramatic Tuning of Carbon Dioxide Uptake via Metal Substitution in a Coordination Polymer with Cylindrical Pores, J. Am. Chem. Soc., (2009), 130(33): 10870-71.
Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted La2 03 Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Labinger. Oxidative coupling of methane: an inherent limit to selectivity? Catal. Lett. 1988; 1:371-376.
Corma, From Microporous to Mesoporous Molecular Sieve Materials and Their Use in Catalysis, Chern. Rev., 97, 1997, pp. 2373-2419.
Debart, et al. α-MNO2 Nanowires: A catalyst for the 02 Electrode in Rechargeabl Lithium Batteries. Angewandte Chemie International Edition 47: 4521-4524, 2008.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Li, B. et al. Advances in CO2 capture technology: A patent review. Applied Energy (2013) 102:1439-1447.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano-(2Li20/Mg0) Catalyst/Porous Alpha-Alumina Composite for the Oxidative Coupling of Methane Reaction, AIChE Journal, Mar. 2010, 56(3):717-28.
Gao, et al. A study on methanol steam reforming to CO2 and H2 over the La2 C04 nanofiber catalyst. Journal of Solid State Chemistry 181: 7-13, 2008.
Gao, et al. The direct decomposition of NO over the La2 Cu04 nanofiber catalyst. Journal of Solid State Chemistry 181: 2804-2807, 2008.
Geier, et al., Selective adsorption of ethylene over ethane and propylene over propane in the metal-organic frameworks M2(dobdc) (M=Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al, Mesoporous Material from Zeolite, Journal of Poruous Materials, 2002, pp. 43-48.

(56) References Cited

OTHER PUBLICATIONS

Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of the Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.
Haag, W.O. et al. Aromatics, Light Olefins and Gasoline from Methanol: Mechanistic Pathways with ZSM-5 Zeolite Catalyst. J Mol Catalysis (1982) 17:161-169.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale 5(22): 10844-10848, 2013.
Huang, et al. Exploiting shape effects of La2O3 nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Li, et al. Combined Single-Pass Conversion of Methane via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 W04—Mn.SiC monolithic foam catalyst with improved thermal properties for the oxidative coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Mokhatab et al. "Handbook of Natural Gas Transmission and Processing: Principles and Practices" 2015. Chapter 7, pp. 237-242. (Year 2015).
Morgan, C.R. et al. Gasoline from Alcohols. Ind Eng Chem Prod Res Dev(1981) 20:185-190.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Jounral of the Chinese Rare Earth Society 23 (Spec. Issue): 33-36, Dec. 2005.
Nyce, et al. PCT/US2015/010525 filed Jan. 7, 2015 for Ethylene-to-Liquids Systems and Methods.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 W04/Si02 and Mn/NA2 W04/MgO Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 2017—https://web.archive. org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Sheridan, D. et al. PCT/US2014/067465 filed Nov. 25, 2014 for Integrated Mixers and Heat Exchangers for Oxidative Coupling Methane Systems.

(56) References Cited

OTHER PUBLICATIONS

Simons, K. Membrane Technologies for CO2 Capture. Dissertation, U. of Twente (2010).

Smith, et al. Recent developments in solvent absorption technologies at the CO2CRC in Australia. Energy Procedia 1 (2009): 1549-1555.

Somorjai, et al. High technology catalysts towards 100% selectivity Fabrication, characterization and reaction studies. Catalysis today 100:201-215, 2005.

Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.

Suzuki, K. Toshiba's Activity in Clean Coal and Carbon Capture Technology for Thermal Power Plants. Apec Clean Fossil Energy Technical and Policy Seminar (Feb. 22, 2012).

Tabak, S.A. et al. Conversion of Methanol over ZSM-5 to Fuels and Chemicals. Cat Today (1990) 307-327.

Takanabe, et al. Mechanistic Aspects and Reaction Pathways for Oxidative Coupling of Methane on Mn/NA2 W04/Si02 Catalysts. Journal of Physical Chemistry C 113(23):10131-10145, 2009.

Takanabe, et al. Rate and Selectivity Enhancements Mediated by OH Radicals in the Oxidative coupling of Methane Catalyzed by Mn/NA2 W04/SiO2 . Angewandte Chemie International Edition 47:7689-7693, 2008.

Tong, et al. Development strategy research of downstream products of ethene in Tianjin. Tianjin Economy, pp. 37-40,1996.

Trautmann, et al. Cryogenic technology for nitrogen rejection from variable content natural gas. Presented at the XIV Convencion Internacional de Gas, Caracas, Venezuela, May 10-12, 2000, 13 pages.

Wang, et al. Autothermal oxidative coupling of methane on the SrCO3/Sm2 03 catalysts. Catalysis communications 10: 807-810, 2009.

Wang, et al. Comparative study on oxidation of methane to ethane and ethylene over NA2 W04—Mn/SiO2 catalysts prepared by different methods. Journal of Molecular Catalysis A: Chemical 245:272-277, 2006.

\* cited by examiner

OXIDATIVE COUPLING OF METHANE IMPLEMENTATIONS FOR OLEFIN PRODUCTION

CROSS-REFERENCE

This application is a continuation application of U.S. patent application Ser. No. 15/076,402, filed Mar. 21, 2016, which is a continuation application of U.S. patent application Ser. No. 14/789,946, filed Jul. 1, 2015, now U.S. Pat. No. 9,352,295, which is a continuation application of U.S. patent application Ser. No. 14/592,668, filed Jan. 8, 2015, now U.S. Pat. No. 9,701,597, which application claims the benefit of U.S. Provisional Patent Application Ser. No. 61/925,627, filed Jan. 9, 2014, U.S. Provisional Patent Application Ser. No. 61/955,112, filed Mar. 18, 2014, U.S. Provisional Patent Application Ser. No. 61/996,789, filed May 14, 2014, U.S. Provisional Patent Application Ser. No. 62/050,720, filed Sep. 15, 2014, U.S. Provisional Patent Application Ser. No. 62/073,478, filed Oct. 31, 2014, and U.S. Provisional Patent Application Ser. No. 62/086,650, filed Dec. 2, 2014, each of which is entirely incorporated herein by reference.

BACKGROUND

The modern petrochemical industry makes extensive use of cracking and fractionation technology to produce and separate various desirable compounds from crude oil. Cracking and fractionation operations are energy intensive and generate considerable quantities of greenhouse gases.

The gradual depletion of worldwide petroleum reserves and the commensurate increase in petroleum prices may place extraordinary pressure on refiners to minimize losses and improve efficiency when producing products from existing feedstocks, and also to seek viable alternative feedstocks capable of providing affordable hydrocarbon intermediates and liquid fuels to downstream consumers.

Methane may provide an attractive alternative feedstock for the production of hydrocarbon intermediates and liquid fuels due to its widespread availability and relatively low cost when compared to crude oil. Worldwide methane reserves may be in the hundreds of years at current consumption rates and new production stimulation technologies may make formerly unattractive methane deposits commercially viable.

Ethylene is an important commodity chemical intermediate. The worldwide production of ethylene exceeds that of any organic compound. Ethylene is used in the production of polyethylene plastics, polyvinyl chloride, ethylene oxide, ethylene chloride, ethylbenzene, alpha-olefins, linear alcohols, vinyl acetate, and fuel blendstocks such as, but not limited to, aromatics, alkanes and alkenes. The growth in demand for ethylene and ethylene based derivatives is forecast to increase as the developing world continues to register higher economic growth. The bulk of worldwide annual commercial production of ethylene is based on thermal cracking of petroleum hydrocarbons with stream; the process is commonly called pyrolysis or steam cracking. The feedstocks for steam cracking can be derived either from crude oil (e.g., naphtha) or from associated or natural gas (e.g., ethane, propane, LPG). Ethylene production is primarily limited to high volume production as a commodity chemical in relatively large steam crackers or other petrochemical complexes that also process the large number of other hydrocarbon byproducts generated in the steam cracking process. Producing ethylene from far more abundant and significantly less expensive methane in natural gas provides an attractive alternative to ethylene produced from steam cracking (e.g., naphtha or gaseous feedstocks). Oligomerization processes can be used to further convert ethylene into longer chain hydrocarbons useful as polymer components for plastics, vinyls, and other high value polymeric products. Additionally, these oligomerization processes may be used to convert ethylene to other longer hydrocarbons, such as $C_6$, $C_7$, $C_8$ and longer hydrocarbons useful for fuels like gasoline, diesel, jet fuel and blendstocks for these fuels, as well as other high value specialty chemicals.

SUMMARY

Recognized herein is the need for efficient and commercially viable systems and methods for converting methane to higher chain hydrocarbons, such as hydrocarbon compounds with two or more carbon atoms (also "$C_{2+}$ compounds" herein), such as olefins and/or alkanes. An oxidative coupling of methane ("OCM") reaction is a process by which methane can form one or more $C_{2+}$ compounds.

In an OCM process, methane is oxidized to yield products comprising $C_{2+}$ compounds, including alkanes (e.g., ethane, propane, butane, pentane, etc.) and alkenes (e.g., ethylene, propylene, etc.). Such alkane (also "paraffin" herein) products may not be suitable for use in downstream processes. Unsaturated chemical compounds, such as alkenes (or olefins), may be employed for use in downstream processes. Such compounds may be polymerized to yield polymeric materials, which may be employed for use in various commercial settings.

An aspect of the present disclosure provides oxidative coupling of methane (OCM) system for small scale or world scale production of olefins, comprising: (a) an OCM subsystem that (i) takes as input a feed stream comprising methane ($CH_4$) and a feed stream comprising an oxidizing agent, and (ii) generates from the methane and the oxidizing agent a product stream comprising $C_{2+}$ compounds and non-$C_{2+}$ impurities; and (b) at least one separations subsystem downstream of, and fluidically coupled to, the OCM subsystem, wherein the separations subsystem comprises a first heat exchanger, a de-methanizer unit downstream of the first heat exchanger, and a second heat exchanger downstream of the de-methanizer unit, wherein (1) the first heat exchanger cools the product stream, (2) the de-methanizer unit accepts the product stream from the first heat exchanger and generates an overhead stream comprising methane and at least a portion of the non-$C_{2+}$ impurities, and a bottoms stream comprising at least a portion of the $C_{2+}$ compounds, and (3) at least a portion of the overhead stream is cooled in the second heat exchanger and is subsequently directed to the first heat exchanger to cool the product stream.

In some embodiments of aspects provided herein, the overhead stream is split into at least two streams, and at least one of the two streams is pressurized prior to introduction to the second heat exchanger. In some embodiments of aspects provided herein, the system further comprises a hydrogenation unit downstream of the de-methanizer, wherein the hydrogenation unit accepts a stream comprising the $C_{2+}$ compounds and hydrogenates alkynes in the $C_{2+}$ compounds to alkanes and/or alkenes. In some embodiments of aspects provided herein, the system further comprises a de-ethanizer unit downstream of the hydrogenation unit, wherein the de-ethanizer unit accepts the stream and separates ethane from ethylene. In some embodiments of aspects provided herein, the system further comprises a methanation subsystem upstream of the OCM subsystem, wherein the methanation subsystem reacts $H_2$ with CO and/or $CO_2$ to generate methane, which methane is directed to the OCM subsystem. In some embodiments of aspects provided herein, the system further comprises a sulfur removal subsystem upstream of the OCM subsystem, wherein the sulfur removal subsystem accepts a feed stream comprising methane and decrease the concentration of sulfur in the feed stream. In some embodiments of aspects provided herein, the sulfur removal subsystem further comprises a heat recovery steam generator unit. In some embodiments of aspects provided herein, the system further comprises an absorption system downstream of the OCM subsystem, wherein the absorption system decreases the concentration of $CO_2$ in the product stream. In some embodiments of aspects provided herein, the absorption system comprises an absorption unit and a scrubber downstream of the absorption unit. In some embodiments of aspects provided herein, the oxidizing agent is $O_2$. In some embodiments of aspects provided herein, the $O_2$ is provided by air. In some embodiments of aspects provided herein, the OCM subsystem comprises at least one OCM reactor. In some embodiments of aspects provided herein, the OCM subsystem comprises at least one post-bed cracking unit downstream of the at least one OCM reactor, which post-bed cracking unit is configured to convert at least a portion of alkanes in the product stream to alkenes. In some embodiments of aspects provided herein, the system further comprises a non-OCM process upstream of the OCM subsystem. In some embodiments of aspects provided herein, the non-OCM process is a natural gas liquids process. In some embodiments of aspects provided herein, the non-$C_{2+}$ impurities comprise one or more of nitrogen ($N_2$), oxygen ($O_2$), water ($H_2O$), argon (Ar), carbon monoxide (CO), carbon dioxide ($CO_2$) and $CH_4$.

An aspect of the present disclosure provides an oxidative coupling of methane (OCM) system for small scale or world scale production of olefins, comprising: (a) an OCM subsystem that (i) takes as input a feed stream comprising methane ($CH_4$) and a feed stream comprising an oxidizing agent, and (ii) generates from the methane and the oxidizing agent a product stream comprising $C_{2+}$ compounds and non-$C_{2+}$ impurities; and (b) at least one methanation subsystem downstream of, and fluidically coupled to, the OCM subsystem, wherein the methanation subsystem reacts $H_2$ and CO and/or $CO_2$ included in the non-$C_{2+}$ impurities to generate methane.

In some embodiments of aspects provided herein, at least a portion of the methane generated in the methanation subsystem is recycled to the OCM subsystem. In some embodiments of aspects provided herein, the oxidizing agent is $O_2$. In some embodiments of aspects provided herein, the $O_2$ is provided by air. In some embodiments of aspects provided herein, the OCM subsystem comprises at least one OCM reactor. In some embodiments of aspects provided herein, the OCM subsystem comprises at least one post-bed cracking unit downstream of the at least one OCM reactor, which post-bed cracking unit is configured to convert at least a portion of alkanes in the product stream to alkenes. In some embodiments of aspects provided herein, the system further comprises a non-OCM process upstream of the OCM subsystem. In some embodiments of aspects provided herein, the non-OCM process is a natural gas liquids process. In some embodiments of aspects provided herein, the non-$C_{2+}$ impurities comprise one or more of nitrogen ($N_2$), oxygen ($O_2$), water ($H_2O$), argon (Ar), carbon monoxide (CO), carbon dioxide ($CO_2$) and $CH_4$. In some embodiments of aspects provided herein, the methanation subsystem comprises at least one methanation reactor.

An aspect of the present disclosure provides a catalyst for hydrogenation of acetylene in an oxidative coupling of methane (OCM) process comprising at least one metal element, wherein the catalyst is capable of decreasing the concentration of acetylene to less than about 100 parts per million (ppm) in an OCM effluent.

In some embodiments of aspects provided herein, the catalyst is capable of decreasing the concentration of acetylene to less than about 10 ppm in the OCM effluent. In some embodiments of aspects provided herein, the catalyst is capable of decreasing the concentration of acetylene to less than about 1 ppm in the OCM effluent. In some embodiments of aspects provided herein, the at least one metal element is palladium. In some embodiments of aspects provided herein, the at least one metal element is part of a metal oxide. In some embodiments of aspects provided herein, the catalyst is capable of providing an OCM effluent that comprises at least about 0.5% carbon monoxide. In some embodiments of aspects provided herein, the catalyst is capable of providing an OCM effluent that comprises at least about 1% carbon monoxide. In some embodiments of aspects provided herein, the catalyst is capable of providing an OCM effluent that comprises at least about 3% carbon monoxide. In some embodiments of aspects provided herein, the catalyst has a lifetime of at least about 1 year. In some embodiments of aspects provided herein, the catalyst is capable of providing an OCM effluent that comprises at least about 0.1% acetylene. In some embodiments of aspects provided herein, the catalyst is capable of providing an OCM effluent that comprises at least about 0.3% acetylene. In some embodiments of aspects provided herein, the catalyst is capable of providing an OCM effluent that comprises at least about 0.5% acetylene. In some embodiments of aspects provided herein, the at least one metal element comprises a plurality of metal elements.

An aspect of the present disclosure provides a catalyst for converting carbon monoxide (CO) and/or carbon dioxide ($CO_2$) into methane ($CH_4$) in an oxidative coupling of methane (OCM) process, wherein the catalyst comprises at least one metal element for converting CO and/or $CO_2$ into $CH_4$ at a selectivity for the formation of methane that is at least about 10-fold greater than the selectivity of the catalyst for formation of coke in an OCM effluent.

In some embodiments of aspects provided herein, the catalyst has a selectivity for the formation of methane that is at least about 100-fold greater than the selectivity of the catalyst for formation of coke. In some embodiments of aspects provided herein, the catalyst has a selectivity for the formation of methane that is at least about 1000-fold greater than the selectivity of the catalyst for formation of coke. In some embodiments of aspects provided herein, the catalyst has a selectivity for the formation of methane that is at least about 10000-fold greater than the selectivity of the catalyst for formation of coke. In some embodiments of aspects provided herein, the OCM effluent comprises at least about 3% olefin and/or acetylene compounds. In some embodiments of aspects provided herein, the OCM effluent comprises at least about 5% olefin and/or acetylene compounds. In some embodiments of aspects provided herein, the OCM effluent comprises at least about 10% olefin and/or acetylene compounds. In some embodiments of aspects provided herein, the at least one metal element is nickel. In some embodiments of aspects provided herein, the at least one metal element is part of a metal oxide.

An aspect of the present disclosure provides a method for preventing coke formation on a methanation catalyst in an oxidative coupling of methane (OCM) process, the method comprising (a) providing an OCM effluent comprising carbon monoxide (CO) and/or carbon dioxide ($CO_2$) and (b) using a methanation catalyst to perform a methanation reaction with the OCM effluent, wherein (i) hydrogen and/or water is added to the OCM effluent prior to (b), (ii) olefins and/or acetylene in the OCM effluent is hydrogenated prior to (b); and/or (iii) olefins and/or acetylene are separated and/or condensed from the OCM effluent prior to (b).

In some embodiments of aspects provided herein, (iii) is performed using absorption or adsorption. In some embodiments of aspects provided herein, the methanation reaction forms at least about 1000-fold more methane than coke. In some embodiments of aspects provided herein, the methanation reaction forms at least about 10000-fold more methane than coke. In some embodiments of aspects provided herein, the methanation reaction forms at least about 100000-fold more methane than coke. In some embodiments of aspects provided herein, the method further comprises any two of (i), (ii) and (iii). In some embodiments of aspects provided herein, the method further comprises all of (i), (ii) and (iii).

An aspect of the present disclosure provides an oxidative coupling of methane (OCM) system for production of olefins and power, comprising: (a) an OCM subsystem that (i) takes as input a feed stream comprising methane ($CH_4$) and a feed stream comprising an oxidizing agent, and (ii) generates from the methane and the oxidizing agent a product stream comprising $C_{2+}$ compounds and heat; and (b) a power subsystem fluidically and/or thermally coupled to the OCM subsystem that converts the heat into electrical power.

In some embodiments of aspects provided herein, the oxidizing agent is $O_2$. In some embodiments of aspects provided herein, the $O_2$ is provided by air. In some embodiments of aspects provided herein, the OCM subsystem comprises at least one OCM reactor. In some embodiments of aspects provided herein, the OCM subsystem comprises at least one post-bed cracking unit within the at least one OCM reactor or downstream of the at least one OCM reactor, which post-bed cracking unit is configured to convert at least a portion of alkanes in the product stream to alkenes. In some embodiments of aspects provided herein, the power subsystem is a gas turbine combined cycle (GTCC). In some embodiments of aspects provided herein, the system further comprises a steam generator for generating steam from the heat, which steam is converted to electrical power in the power subsystem. In some embodiments of aspects provided herein, the power subsystem comprises a gas turbine and un-reacted methane from the OCM subsystem is converted to electrical power using the gas turbine. In some embodiments of aspects provided herein, a ratio of production of $C_{2+}$ alkenes and production of power can be varied by adjusting a composition of the feed stream. In some embodiments of aspects provided herein, a ratio of production of $C_{2+}$ alkenes and production of power can be varied by adjusting an amount of $C_{2+}$ alkanes fed into a post-bed cracking section of the OCM subsystem.

An aspect of the present disclosure provides a method for producing at least one $C_{2+}$ alkene and power, comprising: (a) directing methane and an oxidizing agent into a reactor comprising a catalyst unit, wherein the catalyst unit comprises an oxidative coupling of methane (OCM) catalyst that facilitates an OCM reaction that produces $C_{2+}$ alkene; (b) reacting the methane and oxidizing agent with the aid of the OCM catalyst to generate at least one OCM product comprising at least one $C_{2+}$ compound and heat; and (c) generating electrical power from the heat.

In some embodiments of aspects provided herein, the heat is converted to steam and the steam is converted to power in a steam turbine. In some embodiments of aspects provided herein, un-reacted methane from the reactor is converted to electrical power in a gas turbine. In some embodiments of aspects provided herein, the reactor comprises a cracking unit downstream of the catalyst unit, wherein the cracking unit generates $C_{2+}$ alkene from $C_{2+}$ alkane, and wherein the method further comprises; (d) providing at least one hydrocarbon-containing stream that is directed through the cracking unit, which hydrocarbon-containing stream comprises at least one $C_{2+}$ alkane; and (e) in the cracking unit, cracking the at least one $C_{2+}$ alkane to provide the at least one $C_{2+}$ alkene in a product stream that is directed out of the reactor. In some embodiments of aspects provided herein, the hydrocarbon-containing stream comprises at least one OCM product. In some embodiments of aspects provided herein, the $C_{2+}$ alkene produced from the at least one hydrocarbon-containing stream in the cracking unit is in addition to the $C_{2+}$ alkene produced from the methane and the oxidizing agent in the reactor. In some embodiments of aspects provided herein, the amount of steam produced is varied or the amount of at least one hydrocarbon-containing stream that is directed through the cracking unit is varied to alter the amount of electrical power produced and the amount of $C_{2+}$ alkene produced. In some embodiments of aspects provided herein, the OCM catalyst is a nanowire catalyst. In some embodiments of aspects provided herein, the oxidizing agent is $O_2$. In some embodiments of aspects provided herein, the at least one $C_{2+}$ alkane comprises a plurality of $C_{2+}$ alkanes. In some embodiments of aspects provided herein, the cracking unit generates $C_{2+}$ alkene from $C_{2+}$ alkane with the aid of the heat generated in the OCM reaction. In some embodiments of aspects provided herein, the reactor is adiabatic.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent comprising carbon dioxide ($CO_2$), hydrogen ($H_2$), one or more $C_{2+}$ compounds, and methane ($CH_4$); (b) separating the OCM effluent into (i) a first stream comprising at least some of the one or more $C_{2+}$ compounds and (ii) a second stream comprising carbon monoxide (CO), $CO_2$, $H_2$, and $CH_4$; (c) methanating the second stream to produce a first OCM reactor feed comprising $CH_4$ formed from the $H_2$ and CO and/or $CO_2$ in the second stream; (d) methanating a third stream comprising $CH_4$ and $H_2$ to produce a second OCM reactor feed comprising $CH_4$, which third stream is from an ethylene cracker; and (e) directing the first and second OCM reactor feeds to the OCM reactor.

In some embodiments of aspects provided herein, the second stream and the third stream are methanated in a single methanation reactor. In some embodiments of aspects provided herein, the method further comprises providing at least a portion of the first stream to the ethylene cracker. In some embodiments of aspects provided herein, the at least the portion of the first stream is provided to a gas compressor or a fractionation unit of the ethylene cracker. In some embodiments of aspects provided herein, the third stream is the overhead stream of a demethanizer unit of the ethylene cracker. In some embodiments of aspects provided herein, the separating in (b) is performed at least in part in a pressure swing adsorption (PSA) unit. In some embodiments of aspects provided herein, the separating in (b) is performed at least in part with a $CO_2$ removal system or a process gas dryer. In some embodiments of aspects provided herein, the OCM effluent is compressed prior to (b). In some embodiments of aspects provided herein, the method further comprises feeding oxygen ($O_2$) as an oxidizing agent to the OCM reactor, which $O_2$ takes part in the OCM reaction. In some embodiments of aspects provided herein, the OCM effluent comprises carbon monoxide (CO) that is converted into $CH_4$ in (c). In some embodiments of aspects provided herein, the OCM reaction further reacts $CH_4$ from natural gas to achieve additional ethylene production. In some embodiments of aspects provided herein, the third stream further comprises $CH_4$.

An aspect of the present disclosure provides an oxidative coupling of methane (OCM) system for production of hydrocarbon compounds including two or more carbon atoms ($C_{2+}$ compounds), comprising: (a) an OCM subsystem that (i) takes as input a first feed stream comprising methane ($CH_4$) and a second feed stream comprising an oxidizing agent, and (ii) generates a product stream comprising $C_{2+}$ compounds from the $CH_4$ and the oxidizing agent; (b) a separation subsystem fluidically coupled to the OCM subsystem that separates the product stream into (i) a first stream comprising $C_{2+}$ compounds and (ii) a second stream comprising hydrogen ($H_2$) and carbon dioxide ($CO_2$) and/or carbon monoxide (CO); (c) a methanation subsystem fluidically coupled to the second stream and to the OCM subsystem, wherein the methanation subsystem converts $H_2$ and $CO_2$ and/or CO into $CH_4$; and (d) an ethylene cracker subsystem fluidically coupled to the methanation subsystem that provides $CH_4H_2$, $CO_2$ and/or CO to the methanation subsystem.

In some embodiments of aspects provided herein, the methanation subsystem provides $CH_4$ to the OCM subsystem. In some embodiments of aspects provided herein, at least some of the additional $H_2$ is derived from a demethanizer of the ethylene cracker subsystem. In some embodiments of aspects provided herein, the first stream is fluidically coupled to the ethylene cracker subsystem. In some embodiments of aspects provided herein, the first stream is fractionated in the ethylene cracker subsystem. In some embodiments of aspects provided herein, the separation subsystem comprises a pressure swing adsorption (PSA) unit. In some embodiments of aspects provided herein, the OCM subsystem reacts $CH_4$ from natural gas with the oxidizing agent in an OCM reaction. In some embodiments of aspects provided herein, the oxidizing agent comprises $O_2$. In some embodiments of aspects provided herein, the $O_2$ is generated from air. In some embodiments of aspects provided herein, the OCM subsystem comprises at least one OCM reactor. In some embodiments of aspects provided herein, the OCM subsystem comprises at least one post-bed cracking unit within the at least one OCM reactor or downstream of the at least one OCM reactor, which post-bed cracking unit is configured to convert at least a portion of alkanes in the product stream to alkenes. In some embodiments of aspects provided herein, the reactor is adiabatic.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) methanating the second stream to produce a first methanated stream comprising $CH_4$ formed from the $H_2$ and CO and/or $CO_2$ in the second stream; (d) removing at least a portion of the first methanated stream; and (e) directing the portion of the first methanated stream into a natural gas pipeline.

In some embodiments of aspects provided herein, (e) comprises directing the portion of the first methanated stream into the natural gas pipeline in exchange for an item of value.

An aspect of the present disclosure provides a method for producing hydrocarbon compounds including two or more carbon atoms ($C_{2+}$ compounds), the method comprising: (a) performing a natural gas liquids (NGL) extraction in an NGL extraction unit to produce an NGL stream comprising ethane, propane, and/or butane and a methane stream comprising methane; (b) directing the methane stream to an oxidative coupling of methane (OCM) reactor; and (c) performing an OCM reaction in the OCM reactor using the methane stream to produce an OCM effluent comprising carbon dioxide ($CO_2$), hydrogen ($H_2$), one or more $C_{2+}$ compounds, and methane ($CH_4$).

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) directing the second stream to a Fischer-Tropsch (F-T) reactor; (d) in the F-T reactor, performing an F-T reaction using the second stream to produce a first OCM reactor feed comprising $CH_4$ formed from the $H_2$ and CO in the second stream; and (e) directing the first OCM reactor feeds to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; and (c) directing the OCM effluent stream to a heat recovery steam generator (HRSG) system; (d) with the HRSG system, transferring heat from the OCM effluent stream to a water stream to produce steam.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) directing the second stream and an air stream to a gas compressor, and burning at least a portion of the second stream and compressing the air stream to produce a compressed air stream; (d) separating the compressed air stream in an air separation unit (ASU) into an third stream comprising $O_2$ and a fourth stream comprising $N_2$; and (e) feeding the oxygen-rich stream to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) transferring heat from the OCM effluent stream in a first heat exchanger and a second heat exchanger downstream of the first heat exchanger with respect to a flow direction of the OCM effluent stream, thereby cooling the OCM effluent stream; (c) demethanizing the OCM effluent stream in a demethanizer, thereby producing an overhead stream comprising carbon dioxide ($CO_2$), hydrogen ($H_2$), and methane ($CH_4$) and a bottom stream comprising one or more $C_{2+}$ compounds; (d) expanding the overhead stream, thereby cooling the overhead stream; (e) transferring heat to the overhead stream in the second heat exchanger and the first heat exchanger downstream of the second heat exchanger with respect to a flow direction of the overhead stream, thereby heating the overhead stream; and (f) feeding the overhead stream from the first heat exchanger into the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) transferring heat from the OCM effluent stream in a first heat exchanger and subsequently expanding the OCM effluent stream, thereby cooling the OCM effluent stream; (c) demethanizing the OCM effluent stream in a demethanizer, thereby producing an overhead stream comprising carbon dioxide ($CO_2$), hydrogen ($H_2$), and methane ($CH_4$) and a bottom stream comprising one or more $C_{2+}$ compounds; (d) transferring heat to a first portion of the overhead stream in a second heat exchanger and the first heat exchanger downstream of the second heat exchanger with respect to a flow direction of the first portion of the overhead stream, thereby heating the first portion of the overhead stream; (e) compressing a second portion of the overhead stream and, in a phase separation unit, separating the second portion of the overhead stream into a liquid stream and a vapor stream; and (f) directing the liquid stream through the second heat exchanger and into the demethanizer.

In some embodiments of aspects provided herein, the method further comprises expanding the vapor stream to cool the vapor stream. In some embodiments of aspects provided herein, the method further comprises transferring heat to the vapor stream in the second heat exchanger and the first heat exchanger.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) transferring heat from the OCM effluent stream in a first heat exchanger and subsequently expanding the OCM effluent stream, thereby cooling the OCM effluent stream; (c) demethanizing the OCM effluent stream in a demethanizer, thereby producing an overhead stream comprising carbon dioxide ($CO_2$), hydrogen ($H_2$), and methane ($CH_4$) and a bottom stream comprising one or more $C_{2+}$ compounds; (d) compressing a first portion of the overhead stream, thereby heating the first portion of the overhead stream, and subsequently in a second heat exchanger transferring heat from the first portion of the overhead stream, thereby cooling the first portion of the overhead stream; (e) in a phase separation unit, separating the first portion of the overhead stream into a liquid stream and a vapor stream; and (f) transferring heat from the liquid stream in a third heat exchanger and subsequently directing the liquid stream into the demethanizer.

In some embodiments of aspects provided herein, the method further comprises: expanding the vapor stream, thereby cooling the vapor stream; and transferring heat to the vapor stream in the third heat exchanger, the second heat exchanger, and/or the first heat exchanger, thereby heating the vapor stream. In some embodiments of aspects provided herein, the method further comprises: expanding a second portion of the overhead stream, thereby cooling the second portion of the overhead stream; and transferring heat to the second portion of the overhead stream in the third heat exchanger, the second heat exchanger, and/or the first heat exchanger, thereby heating the second portion of the overhead stream.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) transferring heat from the OCM effluent stream in a first heat exchanger, thereby cooling the OCM effluent stream; (c) demethanizing the OCM effluent stream in a demethanizer, thereby producing an overhead stream comprising carbon dioxide ($CO_2$), hydrogen ($H_2$), and methane ($CH_4$) and a bottom stream comprising one or more $C_{2+}$ compounds; (d) compressing a first portion of the overhead stream, thereby heating the first portion of the overhead stream, and subsequently transferring heat from the first portion of the overhead stream in a second heat exchanger, thereby cooling the first portion of the overhead stream; (e) in a first phase separation unit, separating the first portion of the overhead stream into a first liquid stream and a first vapor stream; (f) expanding the vapor stream, thereby cooling the first vapor stream and subsequently transferring heat to the first vapor stream in the second heat exchanger and/or the first heat exchanger, thereby heating the first vapor stream; and (g) sub-cooling and flashing the first liquid stream to produce a two-phase stream and, in a second phase separation unit, separating the two-phase stream into a second liquid stream and a second vapor stream, and directing the second liquid stream to the demethanizer.

An aspect of the present disclosure provides a method for producing hydrocarbon compounds with two or more carbon atoms ($C_{2+}$ compounds), the method comprising: (a) performing an oxidative coupling of methane (OCM) reaction in an OCM system comprising two or more OCM reactor stages to produce an OCM effluent stream comprising carbon dioxide ($CO_2$), hydrogen ($H_2$), one or more $C_{2+}$ compounds, and methane ($CH_4$); (b) separating the OCM effluent into a first stream comprising at least some of the one or more $C_{2+}$ compounds and a second stream comprising carbon monoxide (CO), $CO_2$, $H_2$, and $CH_4$; (c) methanating the second stream to produce a first OCM reactor feed comprising $CH_4$ formed from the $H_2$ and CO and/or $CO_2$ in the second stream; and (d) directing the first OCM reactor feed to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor using air as an oxidant to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) methanating the second stream to produce an OCM reactor feed comprising $CH_4$ formed from the $H_2$ and CO and/or $CO_2$ in the second stream; and (d) directing the OCM reactor feed to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor using $O_2$ as an oxidant to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) methanating the second stream to produce an OCM reactor feed comprising $CH_4$ formed from the $H_2$ and CO and/or $CO_2$ in the second stream; and (d) directing the OCM reactor feed to the OCM reactor.

In some embodiments of aspects provided herein, the OCM reactor feed comprises water.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) separating the second stream in a pressure swing adsorption (PSA) unit to produce an OCM reactor feed comprising $CH_4$ and a third stream comprising $H_2$ and CO and/or $CO_2$; and (d) directing the OCM reactor feed to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream into a first stream comprising at least some of the one or more $C_{2+}$ compounds and a second stream comprising carbon monoxide (CO), $CO_2$, $H_2$, and $CH_4$; (c) separating the second stream in a membrane separation unit to produce an OCM reactor feed comprising $CH_4$ and a third stream comprising $H_2$ and CO and/or $CO_2$; and (d) directing the OCM reactor feed to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream in a pressure swing adsorption (PSA) unit into a first stream comprising at least some of the one or more $C_{2+}$ compounds and $CH_4$ and a second stream comprising carbon monoxide (CO), $CO_2$, and $H_2$; (c) separating the first stream in a demethanizer unit to produce an OCM reactor feed comprising $CH_4$ and a third stream comprising the at least some of the one or more $C_{2+}$ compounds; and (d) directing the OCM reactor feed to the OCM reactor.

An aspect of the present disclosure provides a method for producing hydrocarbon compounds including two or more carbon atoms ($C_{2+}$ compounds), the method comprising: (a) performing an oxidative coupling of methane (OCM) reaction in an OCM reactor to produce an OCM effluent stream comprising carbon dioxide ($CO_2$), hydrogen ($H_2$), one or more $C_{2+}$ compounds, and methane ($CH_4$); (b) separating the OCM effluent stream in a pressure swing adsorption (PSA) unit into a first stream comprising $CH_4$ and a second stream comprising at least some of the one or more $C_{2+}$ compounds, carbon monoxide (CO), $CO_2$, and $H_2$; (c) separating the second stream to produce a third stream comprising the at least some of the one or more $C_{2+}$ compounds and a fourth stream comprising carbon monoxide (CO), $CO_2$, and $H_2$; and (d) directing the first stream to the OCM reactor.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1:
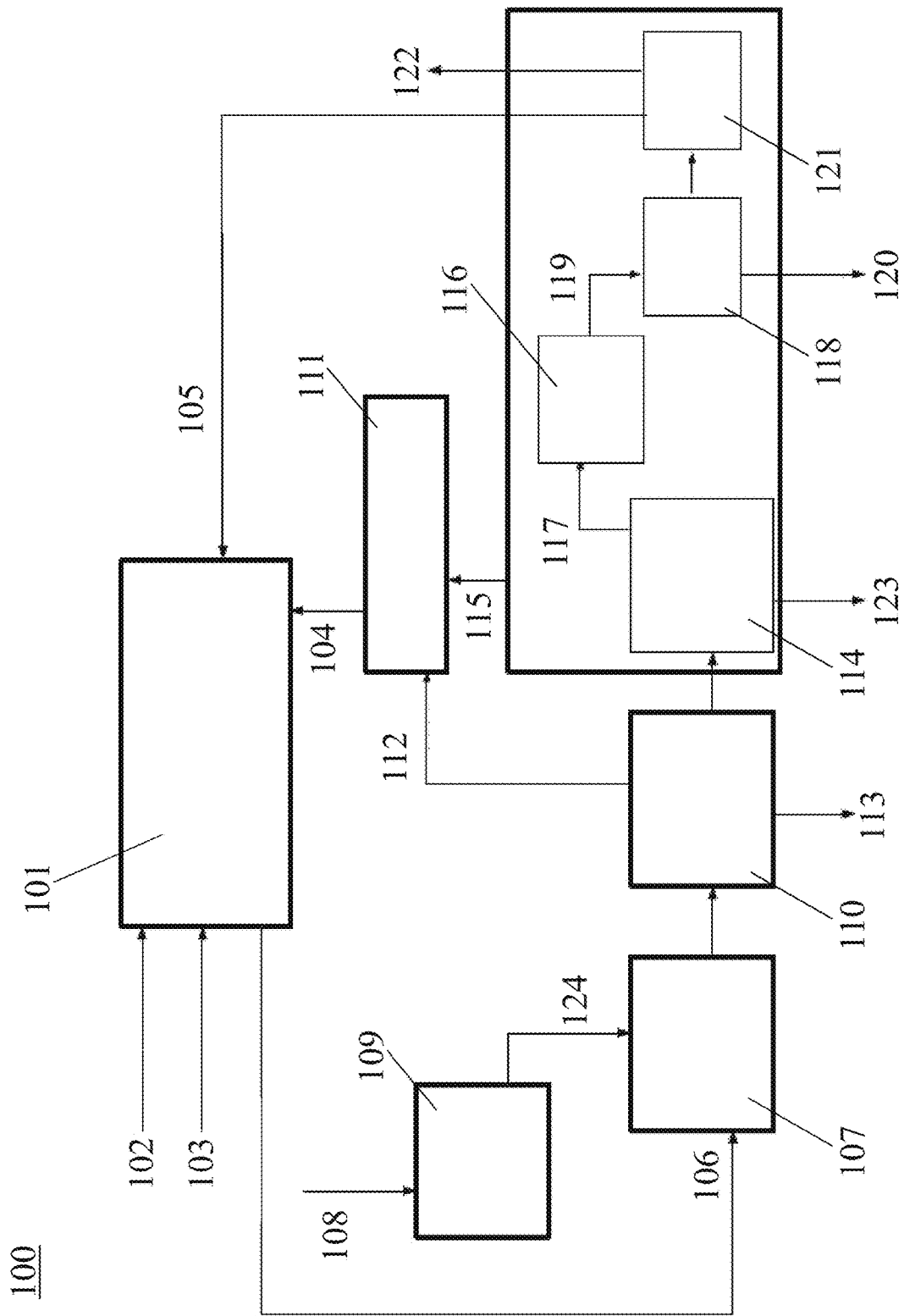
FIG. 1 is a block flow diagram of a system that is configured to generate olefins, such as ethylene.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "higher hydrocarbon," as used herein, generally refers to a higher molecular weight and/or higher chain hydrocarbon. A higher hydrocarbon can have a higher molecular weight and/or carbon content that is higher or larger relative to starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and involves an exothermic reaction. In an OCM reaction, methane can be partially oxidized and coupled to form one or more $C_{2+}$ compounds, such as ethylene. In an example, an OCM reaction is $2CH_4 + O_2 \rightarrow C_2H_4 + H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The terms "$C_{2+}$" and "$C_{2+}$ compound," as used herein, generally refer to a compound comprising two or more carbon atoms. For example, $C_{2+}$ compounds include, without limitation, alkanes, alkenes, alkynes and aromatics containing two or more carbon atoms. $C_{2+}$ compounds can include aldehydes, ketones, esters and carboxylic acids. Examples of $C_{2+}$ compounds include ethane, ethene, acetylene, propane, propene, butane, and butene.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "small scale," as used herein, generally refers to a system that generates less than or equal to about 250 kilotons per annum (KTA) of a given product, such as an olefin (e.g., ethylene).

The term "world scale," as used herein, generally refers to a system that generates greater than about 250 KTA of a given product, such as an olefin (e.g., ethylene). In some examples, a world scale olefin system generates at least about 1000, 1100, 1200, 1300, 1400, 1500, or 1600 KTA of an olefin.

The term "item of value," as used herein, generally refers to money, credit, a good or commodity (e.g., hydrocarbon). An item of value can be traded for another item of value.

OCM Processes

In an OCM process, methane ($CH_4$) reacts with an oxidizing agent over a catalyst bed to generate $C_{2+}$ compounds. For example, methane can react with oxygen over a suitable catalyst to generate ethylene, e.g., 2 $CH_4+O_2 \rightarrow C_2H_4+H_2O$ (See, e.g., Zhang, Q., *Journal of Natural Gas Chem.*, 12:81, 2003; Olah, G. "Hydrocarbon Chemistry", Ed. 2, John Wiley & Sons (2003)). This reaction is exothermic ($\Delta H=-67$ kcals/mole) and has typically been shown to occur at very high temperatures (e.g., >450° C. or >700° C.). Non-selective reactions that can occur include (a) $CH_4+O_2 \rightarrow CO_2+2 H_2O$ and (b) $CH_4+\frac{1}{2}O_2 \rightarrow CO+2H_2$. These non-selective reactions are also exothermic, with reaction heats of −891 kJ/mol and −36 kJ/mol respectively. The conversion of methane to COx products is undesirable due to both heat management and carbon efficiency concerns.

Experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couples in the gas phase to form ethane ($C_2H_6$), followed by dehydrogenation to ethylene ($C_2H_4$). The OCM reaction pathway can have a heterogeneous/homogeneous mechanism, which involves free radical chemistry. Experimental evidence has shown that an oxygen active site on the catalyst activates the methane, removes a single hydrogen atom and creates a methyl radical. Methyl radicals react in the gas phase to produce ethane, which is either oxidative or non-oxidatively dehydrogenated to ethylene. The main reactions in this pathway can be as follows: (a) $CH_4+O^- \rightarrow CH_3^*+OH^-$; (b) 2 $CH_3^* \rightarrow C_2H_6$; (c) $C_2H_6+O^- \rightarrow C_2H_4+H_2O$. In some cases, to improve the reaction yield, ethane can be introduced downstream of the OCM catalyst bed and thermally dehydrogenated via the following reaction: $C_2H_6 \rightarrow C_2H_4+H_2$. This reaction is endothermic ($\Delta H=-144$ kJ/mol), which can utilize the exothermic reaction heat produced during methane conversion. Combining these two reactions in one vessel can increase thermal efficiency while simplifying the process.

Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e., ethane and ethylene), and more importantly, all such reported yields operate at extremely high temperatures (>800° C.). Novel catalysts and processes have been described for use in performing OCM in the production of ethylene from methane at substantially more practicable temperatures, pressures and catalyst activities. These are described in U.S. Patent Publication Nos. 2012/0041246, 2013/0023079, 2013/165728, 2014/0012053 and 2014/0018589, the full disclosures of each of which are incorporated herein by reference in its entirety for all purposes.

An OCM reactor can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed. In some embodiments, at least a portion of the OCM catalyst in at least a portion of the OCM reactor can include one or more OCM catalysts and/or nanostructure-based OCM catalyst compositions, forms and formulations described in, for example, U.S. Patent Publication Nos. 2012/0041246, 2013/0023709, 2013/0158322, 2013/0165728, 2014/0181877 and 2014/0274671, each of which is entirely incorporated herein by reference. Using one or more nanostructure-based OCM catalysts within the OCM reactor, the selectivity of the catalyst in converting methane to desirable $C_{2+}$ compounds can be about 10% or greater; about 20% or greater; about 30% or greater; about 40% or greater; about 50% or greater; about 60% or greater; about 65% or greater; about 70% or greater; about 75% or greater; about 80% or greater; or about 90% or greater.

In some cases, the selectivity of an OCM process in converting methane to desirable $C_{2+}$ compounds is from about 20% to about 90%. In some cases, the selectivity of an OCM process in converting methane to desirable $C_{2+}$ compounds is from about 30% to about 90%. In some cases, the selectivity of an OCM process in converting methane to desirable $C_{2+}$ compounds is from about 40% to about 90%. In some cases, the selectivity of an OCM process in converting methane to desirable $C_{2+}$ compounds is from about 50% to about 90%. In some cases, the selectivity of an OCM process in converting methane to desirable $C_{2+}$ compounds is from about 60% to about 90%. In some cases, the selectivity of an OCM process in converting methane to desirable $C_{2+}$ compounds is from about 70% to about 90%. In some cases, the selectivity of an OCM process in converting methane to desirable $C_{2+}$ compounds is from about 80% to about 90%. The selectivity of an OCM process in converting methane to desirable $C_{2+}$ compounds can be about 10% or greater; about 20% or greater; about 30% or greater; about 40% or greater; about 50% or greater; about 60% or greater; about 65% or greater; about 70% or greater; about 75% or greater; about 80% or greater; or about 90% or greater.

An OCM process can be characterized by a methane conversion fraction. For example, from about 5% to about 50% of methane in an OCM process feed stream can be converted to higher hydrocarbon products. In some cases, about 5%, 10%, 15%, 20%, 25%, 30%, 35%, 40%, 45%, or 50% of methane in an OCM process feed stream is converted to higher hydrocarbon products. In some cases, at least about 5%, 10%, 15%, 20%, 25%, 30%, 35%, 40%, 45%, or 50% of methane in an OCM process feed stream is converted to higher hydrocarbon products. In some cases, at most about 5%, 10%, 15%, 20%, 25%, 30%, 35%, 40%, 45%, or 50% of methane in an OCM process feed stream is converted to higher hydrocarbon products.

An OCM reactor can be sized, shaped, configured, and/or selected based upon the need to dissipate the heat generated by the OCM reaction. In some embodiments, multiple, tubular, fixed bed reactors can be arranged in parallel to facilitate heat removal. At least a portion of the heat generated within the OCM reactor can be recovered, for example the heat can be used to generate high temperature and/or pressure steam. Where co-located with processes requiring a heat input, at least a portion of the heat generated within the OCM reactor may be transferred, for example, using a heat transfer fluid, to the co-located processes. Where no additional use exists for the heat generated within the OCM reactor, the heat can be released to the environment, for example, using a cooling tower or similar evaporative cooling device. In some embodiments, an adiabatic fixed bed reactor system can be used and the subsequent heat can be utilized directly to convert or crack alkanes into olefins. In some embodiments, a fluidized bed reactor system can be utilized. OCM reactor systems useful in the context of the present invention may include those described in, for example, U.S. patent application Ser. No. 13/900,898 (filed May 23, 2013), which is incorporated herein by reference in its entirety for all purposes.

The methane feedstock for an OCM reactor can be provided from various sources, such as non-OCM processes. In an example, methane is provided through natural gas, such as methane generated in a natural gas liquids (NGL) system.

Methane can be combined with a recycle stream from downstream separation units prior to or during introduction into an OCM reactor. In the OCM reactor, methane can catalytically react with an oxidizing agent to yield $C_{2+}$ compounds. The oxidizing agent can be oxygen ($O_2$), which may be provided by way of air or enriched air. Oxygen can be extracted from air, for example, in a cryogenic air separation unit.

To carry out an OCM reaction in conjunction with some catalytic systems, the methane and oxygen containing gases generally need to be brought up to appropriate reaction temperatures, e.g., typically in excess of 450° C. for some catalytic OCM processes, before being introduced to the catalyst, in order to allow initiation of the OCM reaction. Once that reaction begins or "lights off," then the heat of the reaction is typically sufficient to maintain the reactor temperature at appropriate levels. Additionally, these processes may operate at a pressure above atmospheric pressure, such as in the range of about 1 to 30 bars (absolute).

In some cases, the oxidizing agent and/or methane are pre-conditioned prior to, or during, the OCM process. The reactant gases can be pre-conditioned prior to their introduction into a catalytic reactor or reactor bed, in a safe and efficient manner. Such pre-conditioning can include (i) mixing of reactant streams, such as a methane-containing stream and a stream of an oxidizing agent (e.g., oxygen) in an OCM reactor or prior to directing the streams to the OCM reactor, (ii) heating or pre-heating the methane-containing stream and/or the stream of the oxidizing agent using, for example, heat from the OCM reactor, or (iii) a combination of mixing and pre-heating. Such pre-conditioning can minimize, if not eliminate auto-ignition of methane and the oxidizing agent. Systems and methods for pre-conditioning reactant gases are described in, for example, U.S. patent application Ser. No. 14/553,795, filed Nov. 25, 2014, which is entirely incorporated herein by reference.

A wide set of competitive reactions can occur simultaneously or substantially simultaneously with the OCM reaction, including total combustion of both methane and other partial oxidation products. An OCM process can yield $C_{2+}$ compounds as well as non-$C_{2+}$ impurities. The $C_{2+}$ compounds can include a variety of hydrocarbons, such as hydrocarbons with saturated or unsaturated carbon-carbon bonds. Saturated hydrocarbons can include alkanes, such as ethane, propane, butane, pentane and hexane. Unsaturated hydrocarbons may be more suitable for use in downstream non-OCM processes, such as the manufacture of polymeric materials (e.g., polyethylene). Accordingly, at least some, all or substantially all of the alkanes in the $C_{2+}$ compounds may be converted to compounds with unsaturated moieties, such as alkenes, alkynes, alkoxides, ketones, including aromatic variants thereof.

Once formed, $C_{2+}$ compounds can be subjected to further processing to generate desired or otherwise predetermined chemicals. In some situations, the alkane components of the $C_{2+}$ compounds are subjected to cracking in an OCM reactor or a reactor downstream of the OCM reactor to yield other compounds, such as alkenes (or olefins). See, e.g., U.S. patent application Ser. No. 14/553,795, filed Nov. 25, 2014, which is entirely incorporated herein by reference.

The OCM effluent can be cooled after the conversion to ethylene has taken place. The cooling can take place within a portion of the OCM reactor and/or downstream of the OCM reactor (e.g., using at least about 1, 2, 3, 4, 5 or more heat exchangers). In some cases, a heat exchanger is a heat recovery steam generator (HRSG). Cooling the OCM effluent suitably rapidly and to a suitably low temperature can prevent undesirable reactions from occurring with the OCM effluent, including, but not limited to the formation of coke or other by-products.

In some embodiments, the OCM effluent is cooled to a target temperature of equal to or less than about 700° C., equal to or less than about 650° C., equal to or less than about 600° C., equal to or less than about 550° C., equal to or less than about 500° C., equal to or less than about 450° C., equal to or less than about 400° C., equal to or less than about 350° C., equal to or less than about 300° C., equal to or less than about 250° C., or equal to or less than about 200° C. In some cases, the OCM effluent is cooled to the target temperature within about 1 second, within about 900 milliseconds (ms), within about 800 ms, within about 700 ms, within about 600 ms, within about 500 ms, within about 400 ms, within about 300 ms, within about 200 ms, within about 100 ms, within about 80 ms, within about 60 ms, within about 40 ms, or within about 20 ms of the production of the desired or otherwise predetermined concentration of ethylene in the OCM reaction.

In some situations, an OCM system generates ethylene that can be subjected to further processing to generate different hydrocarbons with the aid of conversion processes (or systems). Such a process can be part of an ethylene to liquids (ETL) process flow comprising one or more OCM reactors, separations units, and one or more conversion processes for generating higher molecular weight hydrocarbons. The conversion processes can be integrated in a switchable or selectable manner in which at least a portion or all of the ethylene containing product can be selectively directed to 1, 2, 3, 4, 5, 6, 7, 8, 9, 10, or more different process paths to yield as many different hydrocarbon products. An example OCM and ETL (collectively "OCM-ETL" herein) is provided in U.S. Patent Publication No. 2014/0171707, filed on Dec. 6, 2013, which is entirely incorporated herein by reference.

OCM Processes for Producing Olefins

An aspect of the present disclosure provides OCM processes that are configured to generate olefins (or alkenes), such as ethylene, propylene (or propene), butylenes (or butenes), etc. An OCM process can be a standalone process or can be integrated in a non-OCM process, such as a natural gas liquids (NGL or NGLs) or gas processing system.

Reference will now be made to the figures, wherein like numerals refer to like parts throughout. It will be appreciated that the figures and features therein are not necessarily drawn to scale. In the figures, the direction of fluid flow between units is indicated by arrows. Fluid may be directed from one unit to another with the aid of valves and a fluid flow system. In some examples, a fluid flow system can include compressors and/or pumps, as well as a control system for regulating fluid flow, as described elsewhere herein.

FIG. 1 is a block flow diagram of a system 100 that is configured to generate olefins, such as ethylene. The system 100 can be a small scale or world scale system. The system 100 comprises an OCM sub-system 101 that can include one or more OCM units in series and/or parallel. The OCM sub-system 101 can include one or more post-bed cracking (PBC) units for generating olefins (e.g., ethylene) from alkanes (e.g., ethane and/or propane). A PBC unit can be disposed downstream of an OCM unit. The OCM unit and PBC unit can be situated in separate reactor, or included in the same reactor (e.g., a packed bed for OCM disposed upstream of a PBC unit in the same reactor). In some cases, an integrated OCM unit and PBC unit may be collectively referred to as an OCM reactor.

The OCM sub-system 101 can accept ethane and an oxidizing agent (e.g., $O_2$). In the illustrated example, the OCM sub-system 101 accepts ethane from ethane stream 102 and oxygen ($O_2$) from oxygen stream 103. Ethane can be injected into the OCM sub-system 101 at a PBC unit of the OCM sub-system 101. Oxygen can be provided by way of air or provided from an oxygen generation unit, such as a cryogenic unit that accepts air and generates individual $O_2$ and $N_2$ streams, or by $O_2$ pipeline. The OCM sub-system 101 also accepts methane from $C_1$ recycle stream 104 and ethane from $C_2$ recycle stream 105.

In an OCM unit of the OCM sub-system 101, methane can be catalytically reacted with oxygen in an OCM process to generate an OCM effluent stream 106 comprising $C_{2+}$ compounds and non-$C_{2+}$ impurities. The OCM effluent stream 106 can be directed to a PBC unit of the OCM sub-system 101 to convert one or more alkanes in the OCM effluent stream 106 to alkenes. Next, the OCM effluent stream 106 can be directed to a process gas compressor (PGC) unit 107. Natural gas (NG) is directed along an NG feed 108 to a sulfur removal unit 109, which can remove sulfur-containing chemicals from the NG feed 108 to yield a sulfur-free methane feed 124 to the PGC unit 107. As an alternative, the sulfur removal unit 109 can be excluded if the concentration of Sulfur in the incoming natural gas feed stream is very low and acceptable for the OCM process. As another alternative, the methane feed 124 can be provided from other sources that may not be natural gas. In some cases, for example if the natural gas feed has a considerable quantity of hydrogen, it can be routed to the methanation unit. From the PGC unit 107, the OCM effluent can be directed to $CO_2$ removal unit 110, which can remove $CO_2$ from the OCM effluent. At least a portion of the removed $CO_2$ can be directed to a methanation unit 111 along a $CO_2$ stream 112. At least a portion of the removed $CO_2$ can be directed along $CO_2$ stream 113 for other users, such as, for example, storage or purged from the $CO_2$ removal unit 110. In some cases, the $CO_2$ removal system can comprise a pressure swing adsorption (PSA) unit; in other cases, the $CO_2$ removal system can be based on any other membrane separation process. The effluent from the $CO_2$ removal unit can be treated to remove water. The water removal system can be a molecular sieve dryer, or a series of dryers (not shown in the figure).

Next, the OCM effluent can be directed from the $CO_2$ removal unit 110 to a demethanizer (also "de-methanizer" herein) unit 114, which can separate methane from higher molecular weight hydrocarbons (e.g., acetylene, ethane and ethylene). The separated (or recovered) methane can be directed to the methanation unit 111 along a $C_1$ recycle stream 115. Alternatively, or in addition to, the separated methane can be directed to the OCM sub-system 101. A purge stream 123 can be directed out of the demethanizer unit 114, which is a portion of stream 115. The purge stream can contain methane and inert gas, such as, e.g., $N_2$, He or Ar. The purge flow rate may be sufficient such that the inert gas will not accumulate in the system. The purge stream may be required to remove inert gas(es) that are built-up in the recycle loop.

The methanation unit 111 can generate methane from CO, $CO_2$ and $H_2$. Methane generated in the methanation unit 111 can be directed to the OCM sub-system 101 along $C_1$ recycle stream 104. The methanation unit 111 can be as described elsewhere herein.

In some examples, the demethanizer unit 114 includes one or more distillations columns in series and/or parallel. A serial configuration can enable the separation of different components. A parallel configuration can enable separation of a fluid stream of greater volumetric flow rate. In an example, the demethanizer unit 114 comprises a distillation column and is configured to separate methane from $C_{2+}$ compounds in the OCM effluent stream. The demethanizer unit 114 can be as described elsewhere herein.

Higher molecular weight hydrocarbons separated from methane in the demethanizer unit 114 can be directed to an acetylene conversion unit 116 along stream 117. The acetylene conversion unit 116 can react acetylene ($C_2H_2$) in the OCM effluent with $H_2$ to generate ethylene. The acetylene conversion unit 116 in some cases can react other alkenes with $H_2$ to generate alkanes, such as ethane. The acetylene conversion unit 116 can be a hydrogenation reactor. The OCM effluent stream can then be directed from the acetylene conversion unit 116 to a deethanizer (also "de-ethanizer" herein) unit 118 along stream 119. The deethanizer unit 118 can separate $C_2$ compounds (e.g., ethane and ethylene) from $C_{3+}$ compounds (e.g., propane and propylene). Separated $C_{3+}$ compounds can leave the deethanizer unit 118 along stream 120. $C_2$ compounds from the deethanizer unit 118 can be directed to a $C_2$ splitter 121, which can separate ethane from ethylene. The $C_2$ splitter 121 can be a distillation column. Recovered ethylene can be directed along stream 122 and employed for downstream use.

OCM effluent can be characterized by a particular ethane-to-ethylene ratio or range of ratios. For example, OCM effluent can have an ethane-to ethylene-ratio from about 3:1 to about 1:20. OCM effluent can have an ethane-to-ethylene ratio of about 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

OCM effluent can be characterized by a particular ratio or range of ratios of hydrocarbon compounds with three or more carbon atoms ("$C_{3+}$ compounds") to $C_2$ compounds. For example, OCM effluent can have a $C_{3+}$ compounds-to-$C_2$ compounds ratio from about 0 to about 1:3. OCM effluent can have a $C_{3+}$ compounds-to-$C_2$ compounds ratio of about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, or 1:3.

OCM effluent can be characterized by a particular acetylene-to-ethylene ratio or range of ratios. For example, OCM effluent can have an acetylene-to-ethylene ratio from about 0 to about 1:1. OCM effluent can have an acetylene-to-ethylene ratio of about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, or 1:1.

OCM effluent can be characterized by a particular CO-to-$CO_2$ ratio or range of ratios. For example, OCM effluent can have a CO-to-$CO_2$ ratio from about 0 to about 2:1. OCM effluent can have a CO— to $CO_2$ ratio of about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, or 2:1.

Systems, methods, and processes of the present disclosure, such as those for OCM-ETL, operate on feedstocks with particular ethane-to-methane ratios. For example, a system feedstock can have an ethane-to-methane ratio from about 0 to about 1:3. A system feedstock can have an ethane-to-methane ratio of about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, or 1:3.

The systems of the present disclosure, such as the systems of FIGS. 1-2, can be suited for the production of any olefin, such as, for example, ethylene. Thus, the systems above and elsewhere herein are not limited to ethylene but may be configured to generate other olefins, such as propylene, butenes, pentene, or other alkenes.

Post-bed cracking (PBC) units that may be suitable for use with systems of the present disclosure, such as the systems of FIGS. 1-2, are described in, for example, U.S. patent application Ser. No. 14/553,795, filed Nov. 25, 2014, which is entirely incorporated herein by reference.

Figure 17:
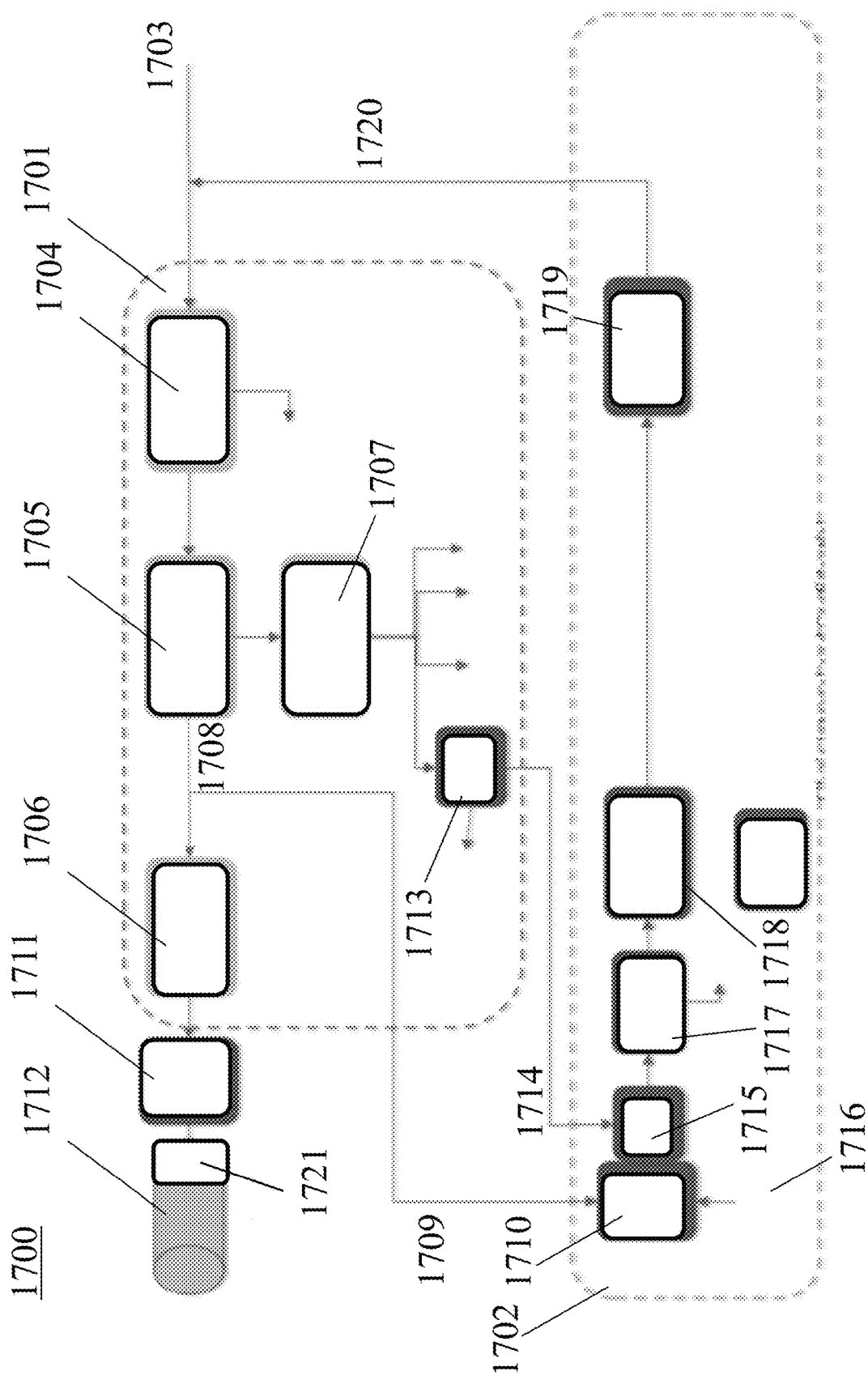
FIG. 17 shows a system comprising an existing natural gas liquids (NGL)/gas processing plant that has been retrofitted with an oxidative coupling of methane (OCM) system for small scale and world scale olefin production (e.g., ethylene production)

The systems of FIGS. 1 and 17 may employ different unit operations for small scale and world scale olefin production (e.g., ethylene production). The present disclosure provides non-limiting example unit operations and process flows for various units that may be employed for use with the systems of FIGS. 1 and 17.

Subsystems in an OCM Unit

Figure 2A:
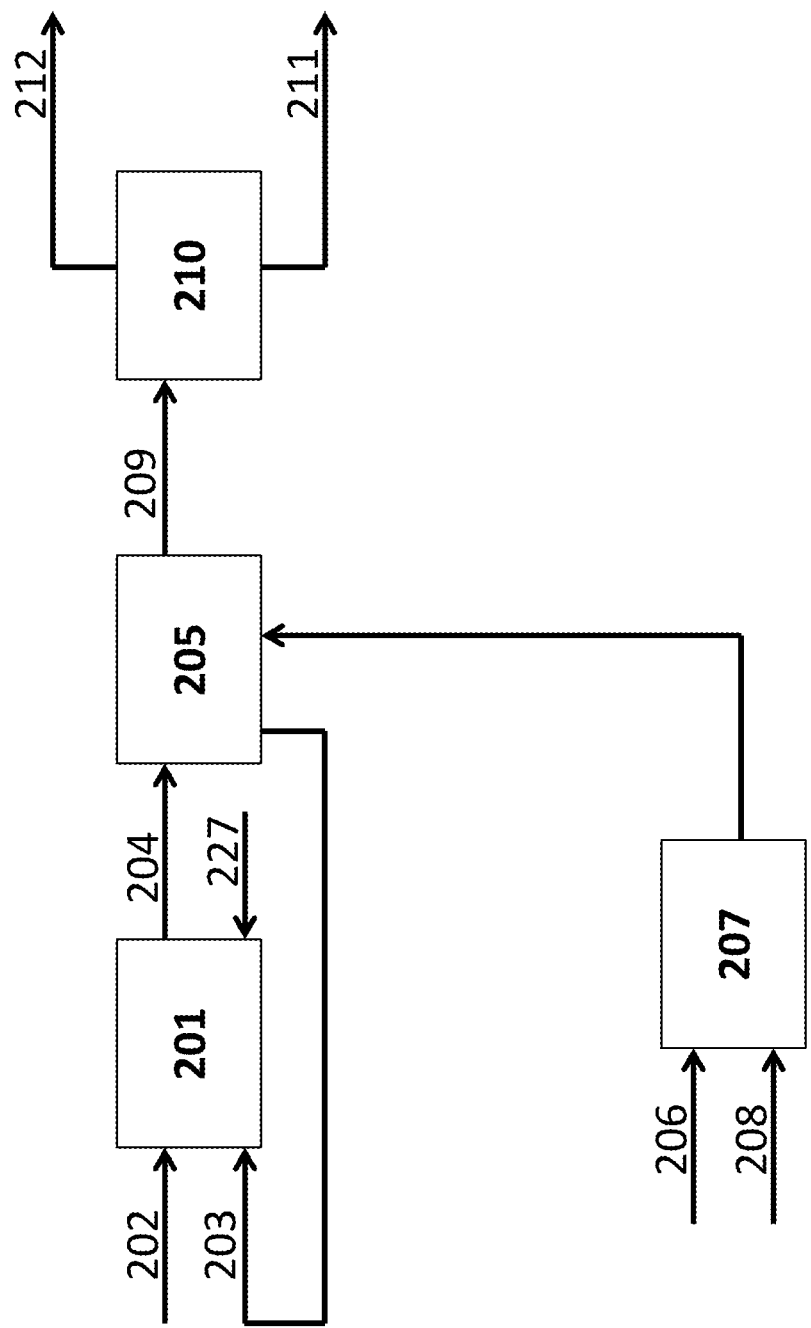
FIGS. 2A and 2B show an oxidative coupling of methane (OCM) system for small scale olefin production.
Figure 2B:
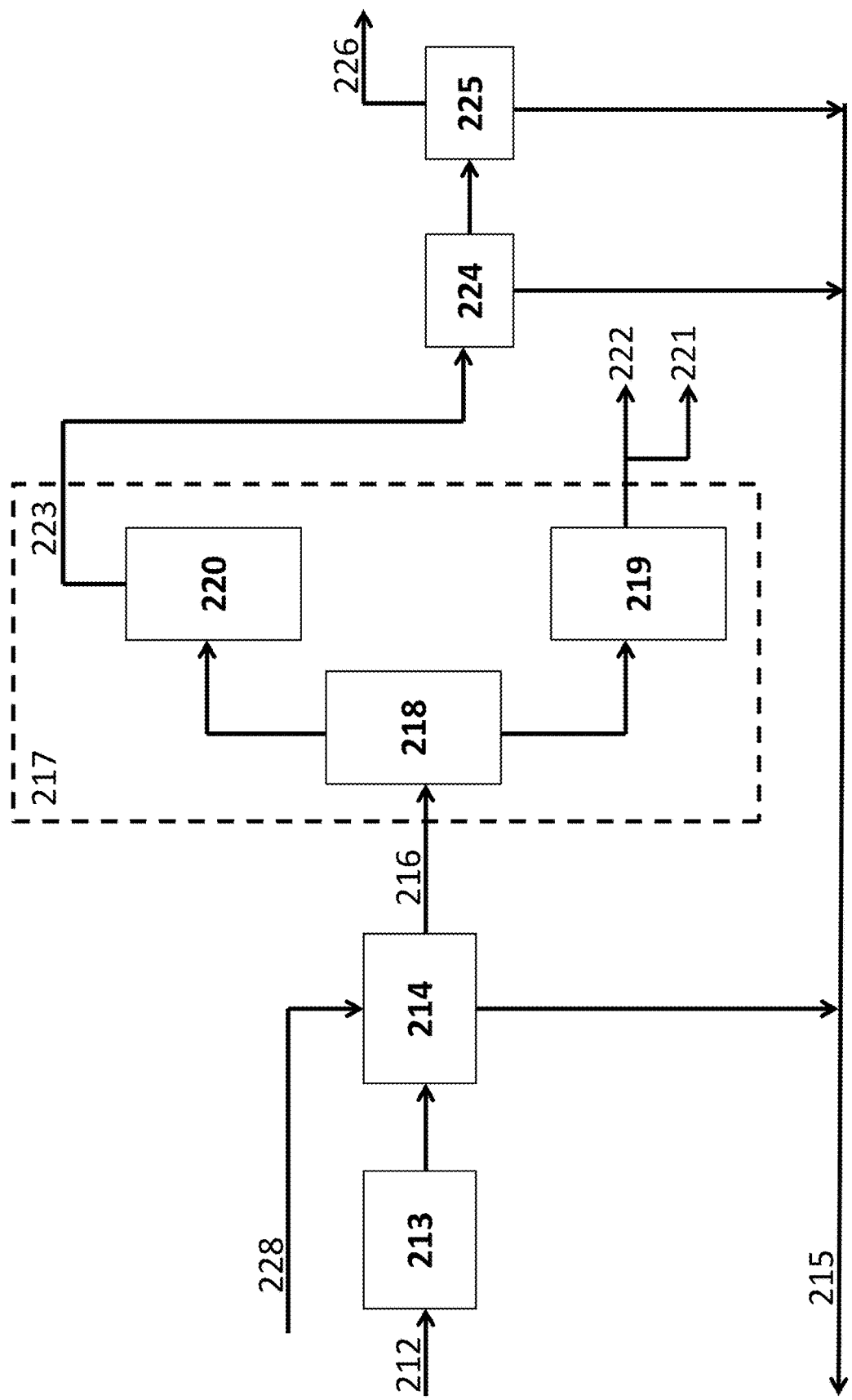
Figure 3:
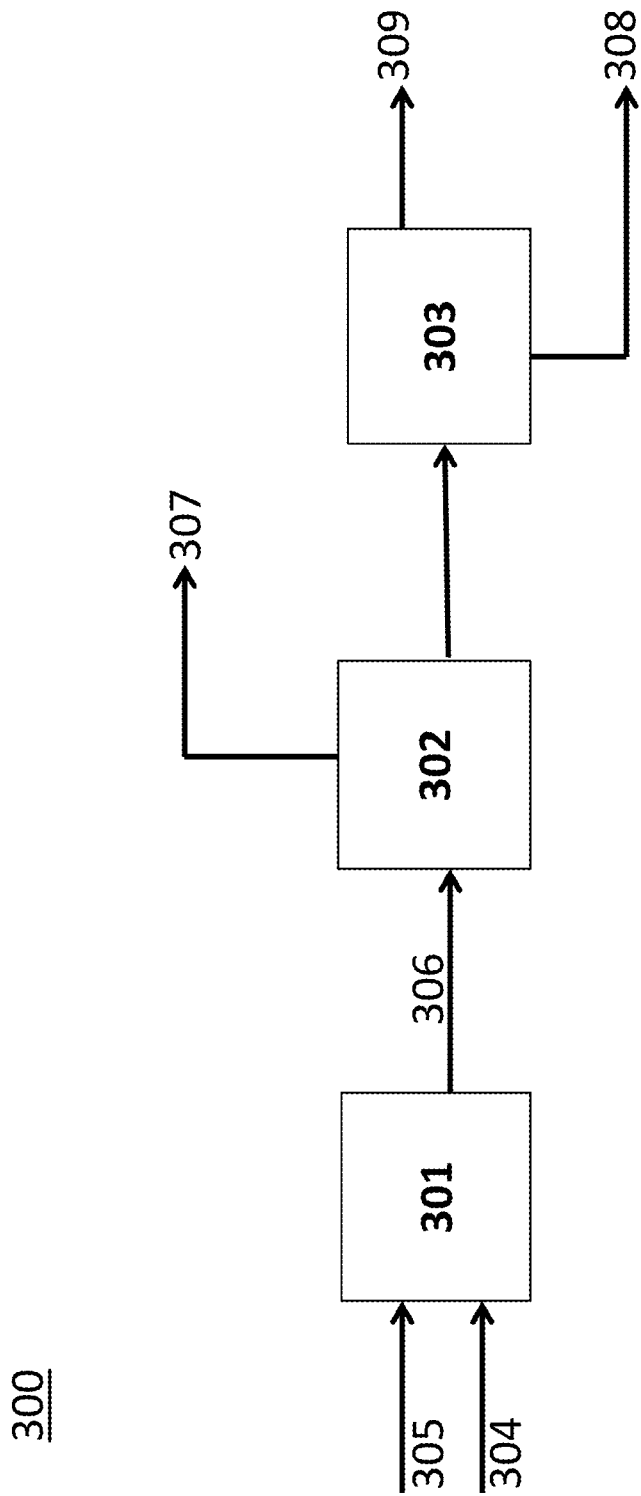
FIG. 3 is a process flow diagram of a system that comprises a hydrogenation unit and a deethanizer unit, which can be employed for small scale and world scale olefin production.
Figure 4:
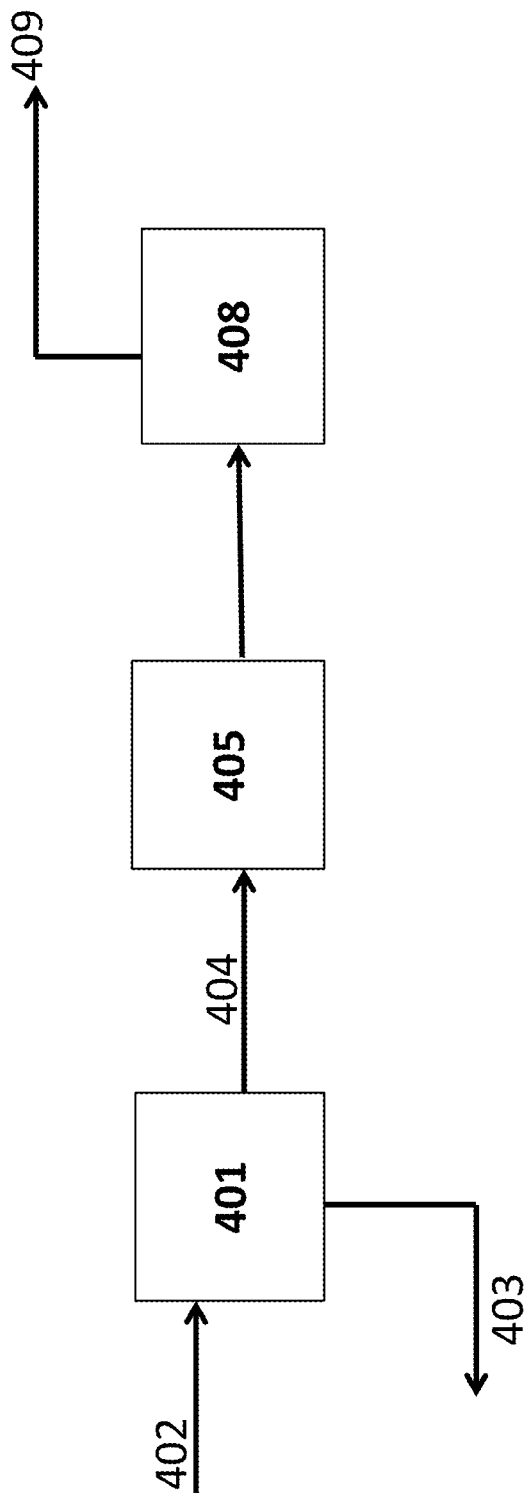
FIG. 4 is process flow diagram of a sulfur removal system for small scale olefin production.

FIGS. 2-4 show various sub-systems that may be suitable for use in a system that is configured for the production of ethylene or other olefins at small scale. Any suitable gas processing technology (e.g., recycle split gas (RSV) or other gas processing technologies may be implemented in the extraction unit to separate methane from NGLs or $C_{2+}$ components with an economic recovery that may be at least about 70%, 80%, 90%, 91%, 92%, 93%, 94%, 95%, 96%, 97%, 98%, or 99%. FIG. 2A shows an OCM reactor 201 that is configured to generate $C_{2+}$ compounds from oxygen ($O_2$) and methane, which can be directed into the OCM reactor 201 along an oxygen stream 202 and a methane stream 203, respectively. Ethane can be directed into the OCM reactor 201 along an ethane recycle stream 227. The streams 202, 203 and 227 can each be pre-conditioned prior to injection into the OCM reactor 201. Such pre-conditioning can include pre-heating and/or pre-mixing. For example, the methane stream 203 can be mixed with the oxygen stream 202 prior to injection into the OCM reactor 201.

The OCM reactor 201 can include an OCM unit upstream of a PBC unit. The OCM unit can include one or more catalysts for catalyzing an OCM reaction using oxygen and methane directed into the OCM reactor 201 along streams 202 and 203, respectively. The OCM reactor 201 can generate an OCM effluent comprising $C_{2+}$ compounds and non-$C_{2+}$ impurities. The OCM effluent can be directed along an OCM effluent stream 204 from the OCM reactor 201 to a plurality of heat exchangers, shown in the figure as a single heat recovery block 205, which transfers heat from the OCM effluent stream 204 to the methane stream 203 to pre-heat the methane stream 203. The OCM effluent stream 204 can be directed to a separator 210, which can remove water from the OCM effluent stream 204 and provide a water stream 211 comprising water and an OCM effluent stream 212 comprising $C_{2+}$ compounds and non-$C_{2+}$ impurities. The concentration of water in the stream 212 may be substantially reduced in relation to the concentration of water in the OCM effluent stream 204.

With continued reference to FIG. 2A, CO and/or $CO_2$ in a recycle stream 206 from downstream processes (see below) are directed into a methanation system 207 and used to generate methane in a methanation process, as described elsewhere herein. Methane generated in the methanation system 207 is directed along the methane stream 203 into the OCM reactor 201. Recycle methane (CO is directed along $C_1$ recycle stream 208 into the methanation system 207 and combined with the methane formed in the methanation system 207. The $C_1$ recycle stream can be pre-heated in a heat exchanger prior to introduction into the methanation system 207.

With reference to FIG. 2B, the OCM effluent stream 212 is directed into the compression and treatment section. The OCM effluent 212 is routed to a quench tower 213 where the OCM effluent gases are quenched with a cooling medium and any process condensates are condensed and removed. The cooled OCM effluent is then fed to the compressor unit 214, which can comprise of a single or multiple stages of compression. The compressor unit 214 can also comprise inter-stage coolers and separator vessels which raise the pressure of the OCM effluent stream 212 (e.g., by a factor of from about 2.5:1 to 4:1) and remove water from the OCM effluent stream 212. The condensate streams from the separator vessels from 214 are routed along 215 as the net condensate removed from the unit. The pressurized OCM effluent stream 216 (which includes $C_{2+}$ compounds) can be mixed with methane from stream 228 (e.g., natural gas stream) and subsequently directed to a $CO_2$ removal system 217 for removing $CO_2$ from the OCM effluent stream 216. The $CO_2$ removal system 217 can be an amine system, a membrane separation system or a caustic based wash system. The absorption system 217 comprises an absorption unit 218, a regenerator 219 and a scrubber 220. The absorption unit 218 can employ an aqueous solution of various alkylamines (also "amines" herein) to scrub $CO_2$ and $H_2S$ from the OCM effluent stream 216. Examples of amines include, without limitation, diethanolamine, monoethanolamine, methyldiethanolamine and diisopropanolamine. The resultant "rich" amine is then routed into the regenerator 219 (e.g., a stripper with a reboiler) to produce regenerated or "lean" amine that is recycled for reuse in the absorption unit 218. The separated $CO_2$ can be purged 221 or recycled 222 (e.g., to the methanation system 207 in stream 206).

The absorption unit 218 generates an OCM effluent stream that can have a low $CO_2$ content, which is directed to the scrubber 220. The scrubber removes additional $CO_2$ and entrained solvents from the OCM effluent stream, using, for example, a sodium hydroxide stream that is directed through the scrubber 220 in a counter flow configuration. The OCM effluent stream 223 is then directed from the scrubber 220 to a separator 224, which removes water from the OCM effluent stream 223. The removed water is directed along stream 215. The OCM effluent stream is then directed to dryers 225 and subsequently directed along stream 226. The dryers 225 can remove water from the OCM effluent stream. The OCM effluent stream 223 may be cooled in a heat exchanger upon heat transfer to a $C_1$ recycle stream, for example.

The system of FIGS. 2A and 2B may be employed for use with other systems of the present disclosure. For example, the absorption system 217 of FIG. 2B may be employed for use as the amine unit 110 of FIG. 1. The series of compressors 213, heat exchangers and separators of FIG. 2B may be employed for use as the PGC 107 of FIG. 1.

FIG. 3 is a process flow diagram of a system 300 that can be used to generate ethane and ethylene from acetylene ($C_2H_2$) and subsequently separate ethane from ethylene. The sub-system 300 may be suitable for the small scale production of ethylene. The system 300 can be employed for use as the acetylene reactor 116, deethanizer 118 and $C_2$ splitter 121 of FIG. 1. The system 300 comprises a hydrogenation reactor unit 301, a first separation unit 302 and a second separation unit 303. The first separation unit 302 and second separation unit 303 can be distillation columns. The hydrogenation reactor unit 301 accepts a stream 304 comprising $H_2$ and a stream 305 comprising $C_{2+}$ compounds, which can include acetylene, and converts any acetylene in the stream 305 to ethane and/or ethylene. The $C_{2+}$ compounds are then directed in stream 306 to the first separation unit 302, which separates $C_{3+}$ compounds (e.g., propane, propylene, butane, butene, etc.) from $C_2$ compounds (ethane and/or ethylene) in the $C_{2+}$ compounds. The first separation unit 302 may be referred to as a deethanizer. The $C_{3+}$ compounds are directed along stream 307 and employed for downstream use. The $C_2$ compounds are directed to the second separation unit 303, which separates ethane from ethylene. The second separation unit 303 may be referred to as a $C_2$ splitter. Ethane from the second separation unit 303 is directed along stream 308 and ethylene is directed along stream 309. Ethane can be recycled, such as recycled to an OCM reactor. In some examples, the ethane is recycled to a PBC unit of an OCM reactor.

The stream 304 may be directed to a pressure swing adsorption (PSA) unit (not shown) that is configured to separate $H_2$ from $N_2$. $H_2$ from the stream 304 may then be directed to the hydrogenation reactor 301. The stream 304 may be provided by a separation system, such as the system 1100 of FIG. 11. In situations in which a PSA is employed, the system 300 may be suitable for use in world scale olefin production. For small scale olefin production, the PSA may be precluded.

The acetylene hydrogenation reaction can be practiced over a palladium-based catalyst, such as those used to convert acetylene to ethylene in conventional steam cracking (e.g., the PRICAT™ series including models PD 301/1, PD 308/4, PD 308/6, PD 508/1, PD 408/5, PD 408/7 and PD 608/1, which may be commercially available as tablets or spheres supported on alumina). In some cases, the acetylene hydrogenation catalyst is a doped or modified version of a commercially available catalyst.

However, in some cases, applying an acetylene hydrogenation catalyst to the OCM process that has been developed or optimized for another process (e.g., steam cracking separations and purification processes) can result in operational issues and/or non-optimized performance. For example, in steam cracking, the acetylene conversion reactor can either be located on the front end (prior to cryogenic separations) or back end (after cryogenic separations) of the process. In steam cracking, these differences in running front end and back end typically have to do with the ratio of hydrogen to acetylene present, the ethylene to acetylene ratio, and the non-ethylene olefin (e.g., butadiene) to acetylene ratio. All of these factors can impact the catalyst selectivity for forming ethylene from acetylene, the lifetime and regeneration of the catalyst, green oil formation, specific process conditions for the reactor, and additional hydrogen required for the reaction. These factors are also different between steam cracking versus OCM processes, therefore, provided herein is an acetylene hydrogenation catalyst that is designed to be used in an OCM process.

In OCM implementations, the chemical components going into the acetylene reactor can be different than for steam cracking. For example, OCM effluent can include carbon monoxide and hydrogen. Carbon monoxide can be undesirable because it can compete with the acetylene for the active sites on the hydrogenation catalyst and lead to lower activity of the catalyst (e.g., by occupying those active sites). Hydrogen can be desirable because it is needed for the hydrogenation reaction, however that hydrogen is present in the OCM effluent in a certain ratio and adjusting that ratio can be difficult. Therefore, the catalyst described herein provides the desired outlet concentrations of acetylene, desired selectivity of acetylene conversion to ethylene, desired conversion of acetylene, desired lifetime and desired activity in OCM effluent gas. As used herein, "OCM effluent gas" generally refers to the effluent taken directly from an OCM reactor, or having first undergone any number of further unit operations such as changing the temperature, the pressure, or performing separations on the OCM reactor effluent. The OCM effluent gas can have CO, $H_2$ and butadiene.

In some embodiments, the catalyst decreases the acetylene concentration below about 100 parts per million (ppm), below about 80 ppm, below about 60 ppm, below about 40 ppm, below about 20 ppm, below about 10 ppm, below about 5 ppm, below about 3 ppm, below about 2 ppm, below about 1 ppm, below about 0.5 ppm, below about 0.3 ppm, below about 0.1 ppm, or below about 0.05 ppm.

The concentration of acetylene can be reached in the presence of carbon monoxide (CO). In some embodiments, the feed stream entering the acetylene hydrogenation reactor contains at least about 10%, at least about 9%, at least about 8%, at least about 7%, at least about 6%, at least about 5%, at least about 4%, at least about 3%, at least about 2%, or at least about 1% carbon monoxide.

When used in an OCM process, the acetylene hydrogenation catalyst can have a lifetime of at least about 6 months, at least about 1 year, at least about 2 years, at least about 3 years, at least about 4 years, at least about 5 years, at least about 6 years, at least about 7 years, at least about 8 years, at least about 9 years, or at least about 10 years.

FIG. 4 is a process flow diagram of a sulfur removal system 400, which can be employed for use in removing sulfur-containing compounds from a gas stream. The sulfur removal system 400 can be employed for use as the sulfur removal system 109 of FIG. 1, for example. The system 400 can be employed for use in a system that is configured to generate small scale ethylene. The system 400 comprises a separation unit 401 for removing water form a natural gas stream 402. Water is removed along stream 403. The natural gas stream with decreased water content is directed along stream 404 to a heat exchanger 405, another optional heat exchanger 406 and an absorption unit 408. The heat exchangers 405 and 406 raise the temperature of the natural gas stream. The absorption unit removes $H_2S$ from the natural gas stream. This can provide a stream 409 comprising methane and having a substantially low sulfur and $H_2O$ content. In some examples, the stream 409 is directed to an OCM reactor. As an alternative, or in addition to, the stream 409 can be directed to a natural gas pipeline.

In certain cases, depending on the concentration of sulfur compounds in the natural gas feed stream, the sulfur removal unit can comprise one or more hydrodesulfurization (hydrotreater) reactors to convert the sulfur compounds to H2S, which is then subsequently removed by an amine system.

Figure 5:
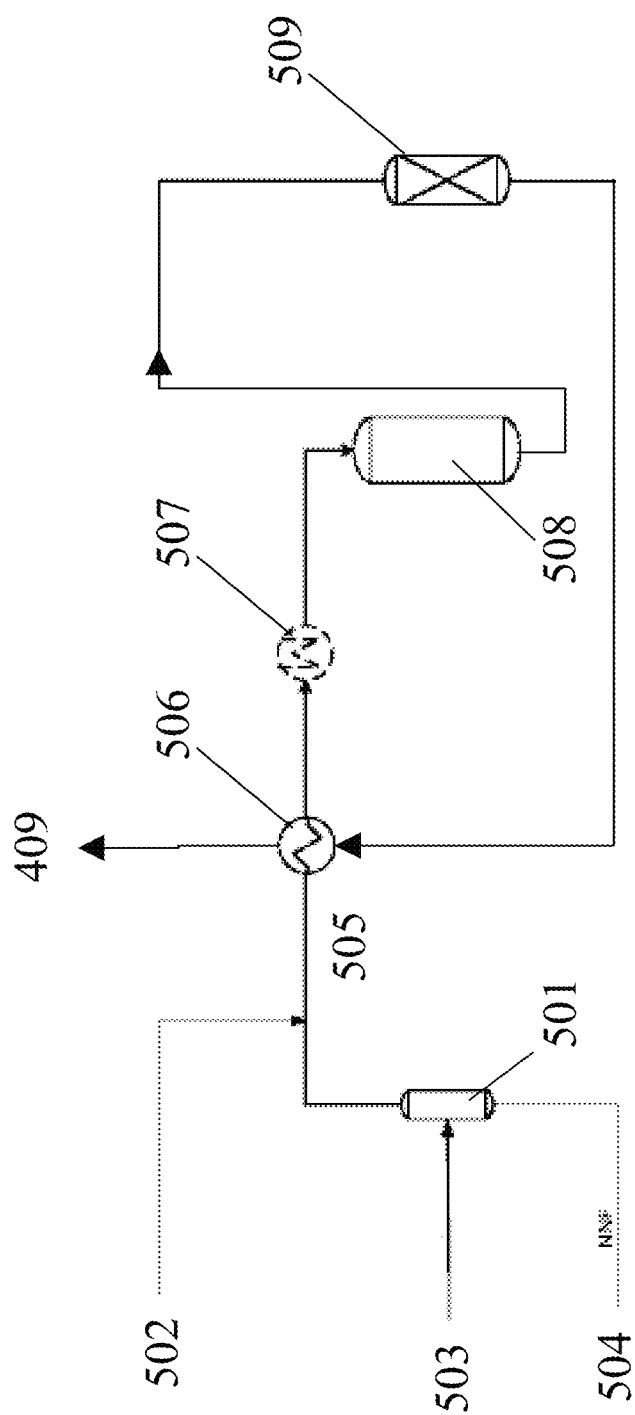
FIG. 5 shows a process flow diagram of a sulfur removal system for world scale olefin production.

FIG. 5 shows a sulfur removal unit comprising a separation unit 501, a hydrogen feed stream 502, a natural gas stream 503, a flare header 504, a methane-containing stream 505, a heat exchanger 506, a heat recovery steam generator (HRSG) system 507, a hydro treating unit 508, an absorption unit 509, and a product stream 510. The separation unit 501 is configured to remove water from the stream 503. Water removed from the stream 503 is directed to the flare header 504. The hydro treating unit 508 generates $H_2S$ from $H_2$ provided by the stream 502 any sulfur in the stream 503. Any sulfur-containing compounds in the stream 503 and generated in the hydro treating unit 508 can be removed in the absorption unit 509. The resulting product stream 510 can include methane and substantially low concentrations of sulfur-containing compounds, such as $H_2S$. In some examples, the product stream 510 can be directed to an OCM reactor or a natural gas pipeline.

The HRSG system 507 is an energy recovery heat exchanger that recovers heat from the stream 505. The HRSG system 507 can produce steam that can be used in a process (cogeneration) or used to drive a steam turbine (combined cycle). The HRSG unit 507 can be as described herein.

Methanation Systems

Oxidative coupling of methane (OCM) can convert natural gas to ethylene and other longer hydrocarbon molecules via reaction of methane with oxygen. Given the operating conditions of OCM, side reactions can include reforming and combustion, which can lead to the presence of significant amounts of $H_2$, CO and $CO_2$ in the OCM effluent stream. $H_2$ content in the effluent stream can range between about 5% and about 15%, between about 1% and about 15%, between about 5% and about 10%, or between about 1% and about 5% (molar basis). The content of CO and $CO_2$ can each range between about 1% and about 5%, between about 1% and about 3%, or between about 3% and about 5% (molar basis). In some cases, the ethylene and all the other longer hydrocarbon molecules contained in the effluent stream are separated and purified to yield the final products of the process. This can leave an effluent stream containing the unconverted methane, hydrogen, CO and $CO_2$ and several other compounds, including low amounts of the product themselves depending on their recovery rates.

In some cases, this effluent stream is recycled to the OCM reactor. However, if CO and $H_2$ are recycled to the OCM reactor along with methane, they can react with oxygen to produce $CO_2$ and $H_2O$, causing various negative consequences to the process including, but not limited to: (a) an increase of the natural gas feed consumption (e.g., because a larger portion of it may result in $CO_2$ generation instead of product generation); (b) a decrease of the OCM per-pass methane conversion (e.g., because a portion of the allowable adiabatic temperature increase may be exploited by the $H_2$ and CO combustion reactions instead of the OCM reactions); and an increase of the oxygen consumption (e.g., because some of the oxygen feed may react with CO and $H_2$ instead of methane).

The effluent stream can be exported to a natural gas pipeline (e.g., to be sold as sales gas into the natural gas infrastructure). Given that specifications can be in place for natural gas pipelines, the concentrations of CO, $CO_2$ and $H_2$ in the effluent can need to be reduced to meet the pipeline requirements. The effluent stream may also be used as a feedstock for certain processes that may require lower concentrations of $H_2$, CO and $CO_2$.

Therefore, it can be desirable to reduce the concentration of $H_2$, CO and $CO_2$ in the OCM effluent stream, upstream or downstream of the separation and recovery of the final products. This can be accomplished using methanation systems and/or by separating $H_2$ and CO from the effluent stream (e.g., using cryogenic separations or adsorption processes). The disclosure also includes separating $CO_2$ from the effluent stream using $CO_2$ removal processes, such as chemical or physical absorption or adsorption or membranes. However, these separation processes can require significant capital investments and can consume considerable amounts of energy, in some cases making an OCM-based process less economically attractive.

The present disclosure also provides systems and methods for reducing CO, $CO_2$ and $H_2$ concentration in a methane stream. Such compounds can be reacted to form methane in a methanation reaction.

An aspect of the present disclosure provides a methanation system that can be employed to reduce the concentration of CO, $CO_2$ and $H_2$ in a given stream, such as an OCM product stream. This can advantageously minimize the concentration of CO, $CO_2$ and $H_2$ in any stream that may be ultimately recycled to an OCM reactor. The methanation system can be employed for use with any system of the present disclosure, such as an OCM-ETL system described herein.

In a methanation system, CO reacts with $H_2$ to yield methane via $CO+3H_2 \rightarrow CH_4+H_2O$. In the methanation system, $CO_2$ can react with $H_2$ to yield methane via $CO_2+4H_2 \rightarrow CH_4+2H_2O$. Such processes are exothermic ($\Delta H=-206$ kJ/mol and $-178$ kJ/mol, respectively) and generate heat that may be used as heat input to other process units, such as heating an OCM reactor of a PBC reactor, or pre-heating reactants, such as methane and/or an oxidizing agent (e.g., O2) prior to an OCM reaction. The methanation reaction can take place in two or more reactors in series, in some cases with intercooling. In some situations, a methanation reactor can be implemented in tandem with an OCM reactor to increase carbon efficiency.

In some cases, to limit the heat release per unit of flow of reactants, methanation can be conducted on streams that contain CO, $CO_2$, $H_2$ and a suitable carrier gas. The carrier gas can include an inert gas, such as, e.g., $N_2$, He or Ar, or an alkane (e.g., methane, ethane, propane and/or butane). The carrier gas can add thermal heat capacity and significantly reduce the adiabatic temperature increase resulting from the methanation reactions.

In some examples, methane and higher carbon alkanes (e.g., ethane, propane and butane) and nitrogen are employed as carrier gases in a methanation process. These molecules can be present in an OCM process, such as in an OCM product stream comprising $C_{2+}$ compounds. Downstream separation units, such as a cryogenic separation unit, can be configured to produce a stream that contains any (or none) of these compounds in combination with CO and $H_2$. This stream can then be directed to the methanation system.

A methanation system can include one or more methanation reactors and heat exchangers. CO, $CO_2$ and $H_2$ can be added along various streams to the one or more methanation reactors. A compressor can be used to increase the $CO_2$ stream pressure up to the methanation operating pressure, which can be from about 2 bar (absolute) to 60 bar, or 3 bar to 30 bar. $CO_2$ can be added to the inlet of the system in order to create an excess of $CO_2$ compared to the amount stoichiometrically required to consume all the available $H_2$. This is done in order to minimize $H_2$ recycled to OCM.

Given the exothermicity of the methanation reactions, a methanation system can include various methanation reactors for performing methanation. In some cases, a methanation reactor is an adiabatic reactor, such as an adiabatic fixed bed reactor. The adiabatic reactor can be in one stage or multiple stages, depending, for example, on the concentration of CO, $CO_2$ and $H_2$ in the feed stream to the methanation system. If multiple stages are used, inter-stage cooling can be performed by either heat exchangers (e.g., a stage effluent can be cooled against the feed stream or any other colder stream available in the plant, such as boiler feed water) or quenching via cold shots, i.e. the feed stream is divided into multiple streams, with one stream being directed to the first stage while each of the other feed streams being mixed with each stage effluent for cooling purposes. As an alternative, or in addition to, a methanation reactor can be an isothermal reactor. In such a case, reaction heat can be removed by the isothermal reactor by, for example, generating steam, which can enable a higher concentration of CO, $CO_2$ and $H_2$ to be used with the isothermal reactor. Apart from adiabatic and isothermal reactors, other types of reactors may be used for methanation, such as fluidized bed reactors.

Figure 6A:
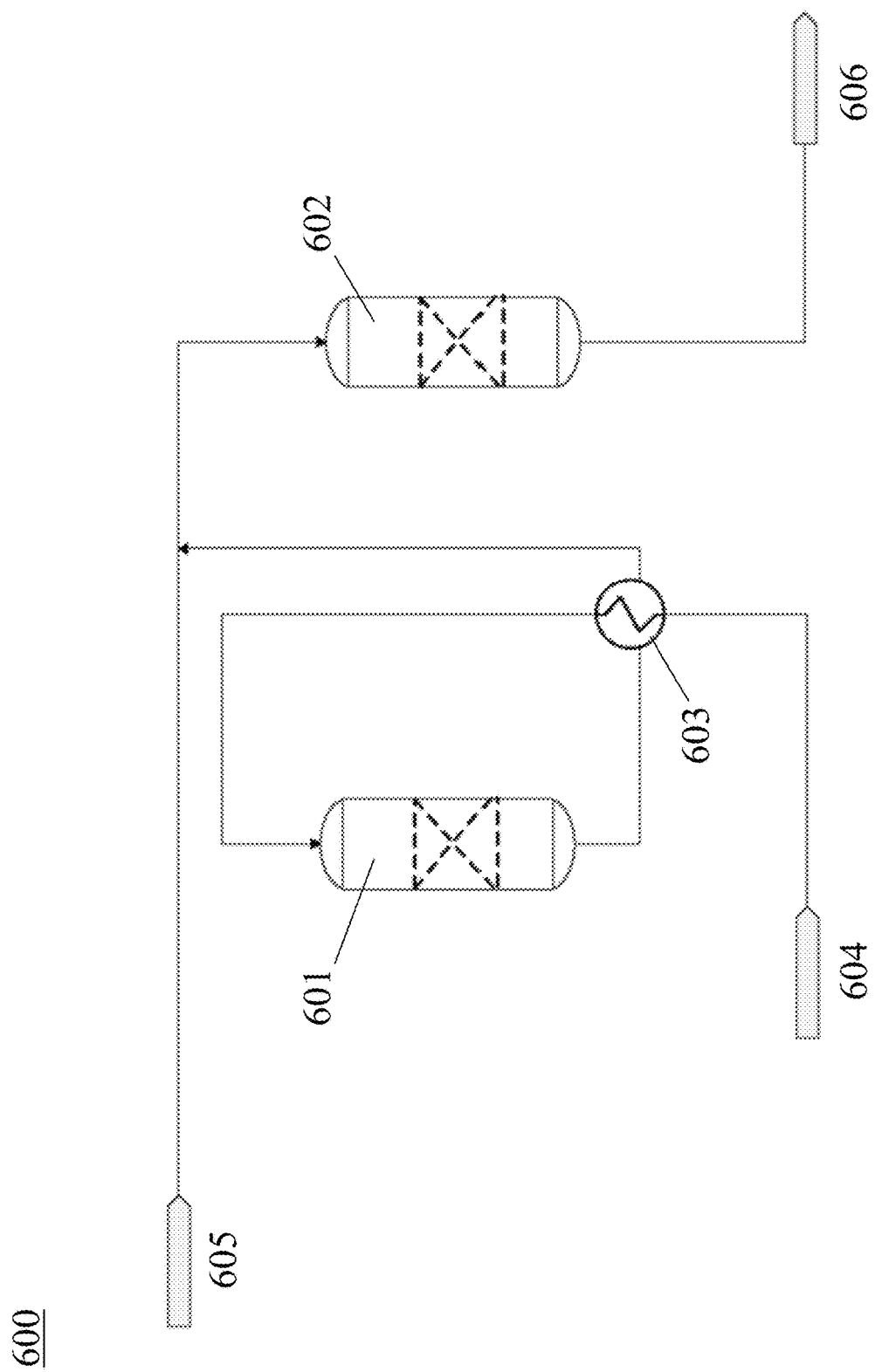
FIGS. 6A and 6B show methanation systems that can be used with systems of the present disclosure.

FIG. 6A shows an example methanation system 600. The system 600 may be used in OCM systems that are for small scale or world scale production of ethylene or other olefins. The system 600 comprises a first reactor 601, second reactor 602 and a heat exchanger 603. The first reactor 601 and second reactor 602 can be adiabatic reactors. During use, a recycle stream 604 comprising methane, CO and $H_2$ (e.g., from a cryogenic separation unit) is directed to the heat exchanger 603. In an example, the recycle stream 604 comprises between about 65% and 90% (molar basis) methane, between about 5% and 15% $H_2$, between 1% and 5% CO, between about 0% and 0.5% ethylene, and the balance inert gases (e.g., $N_2$, Ar and He). The recycle stream 604 can have a temperature from about 20° C. to 40° C., or 20° C. to 30° C., and a pressure from about 2 bar to 60 bar (absolute), or 3 bar to 30 bar. The recycle stream 604 can be generated by a separation unit downstream of an OCM reactor, such as a cryogenic separation unit.

In the heat exchanger 603, the temperature of the recycle stream 604 is increased to about 100° C. to 400° C., or 200° C. to 300° C. The heated recycle stream 604 is then directed to the first reactor 601. In the first reactor 601, CO and $H_2$ in the recycle stream 604 react to yield methane. This reaction can progress until all of the $H_2$ is depleted and/or a temperature approach to equilibrium of about 0 to 30° C., or 0 to 15° C. is achieved. The methanation reaction in the first reactor 601 can result in an adiabatic temperature increase of about 20° C. to 300° C., or 50° C. to 150° C.

Next, products from the first reactor, including methane and unreacted CO and/or $H_2$, can be directed along a first product stream to the heat exchanger 603, where they are cooled to a temperature of about 100° C. to 400° C., or 200° C. to 300° C. In the heat exchanger 603, heat from the first product stream 603 is removed and directed to the recycle stream 604, prior to the recycle stream 604 being directed to the first reactor 601.

Next, a portion of the heated first product stream is mixed with a $CO_2$ stream 605 to yield a mixed stream that is directed to the second reactor 602. The $CO_2$ stream 605 can be generated by a separation unit downstream of an OCM reactor, such as a cryogenic separation unit. This can be the same separation unit that generated the recycle stream 604.

In the second reactor 602, CO and $CO_2$ react with $H_2$ to yield a second product stream 606 comprising methane. The reaction(s) in the second reactor 602 can progress until substantially all of the $H_2$ is depleted and/or a temperature approach to equilibrium of about 0 to 30° C., or 0 to 15° C. is achieved. The proportions of CO, $CO_2$ and $H_2$ in the mixed stream can be selected such that the second product stream 606 is substantially depleted in CO and $H_2$.

The first reactor 601 and the second reactor 602 can be two catalytic stages in the same reactor vessel or can be arranged as two separate vessels. The first reactor 601 and second reactor 602 can each include a catalyst, such as a catalyst comprising one or more of ruthenium, cobalt, nickel and iron. The first reactor 601 and second reactor 602 can be fluidized bed or packed bed reactors. Further, although the system 600 comprises two reactors 601 and 602, the system 600 can include any number of reactors in series and/or in parallel, such as at least 1, 2, 3, 4, 5, 6, 7, 8, 9, 10, 20, 30, 40, or 50 reactors.

Although the $CO_2$ stream 605 is shown to be directed to the second reactor 602 and not the first reactor 601, in an alternative configuration, at least a portion or the entire $CO_2$ stream 605 can be directed to the first reactor 601. The proportions of CO, $CO_2$ and $H_2$ can be selected such that the methanation product stream is substantially depleted in CO and $H_2$.

Methane generated in the system 600 can be employed for various uses. In an example, at least a portion of the methane can be recycled to an OCM reactor (e.g., as part of an OCM-ETL system) to generate $C_{2+}$ compounds, including alkenes (e.g., ethylene). As an alternative, or in addition to, at least a portion of the methane can be directed to a non-OCM process, such as a natural gas stream of a natural gas plant. As another alternative, or in addition to, at least a portion of the methane can be directed to end users, such as along a natural gas pipeline.

Figure 6B:
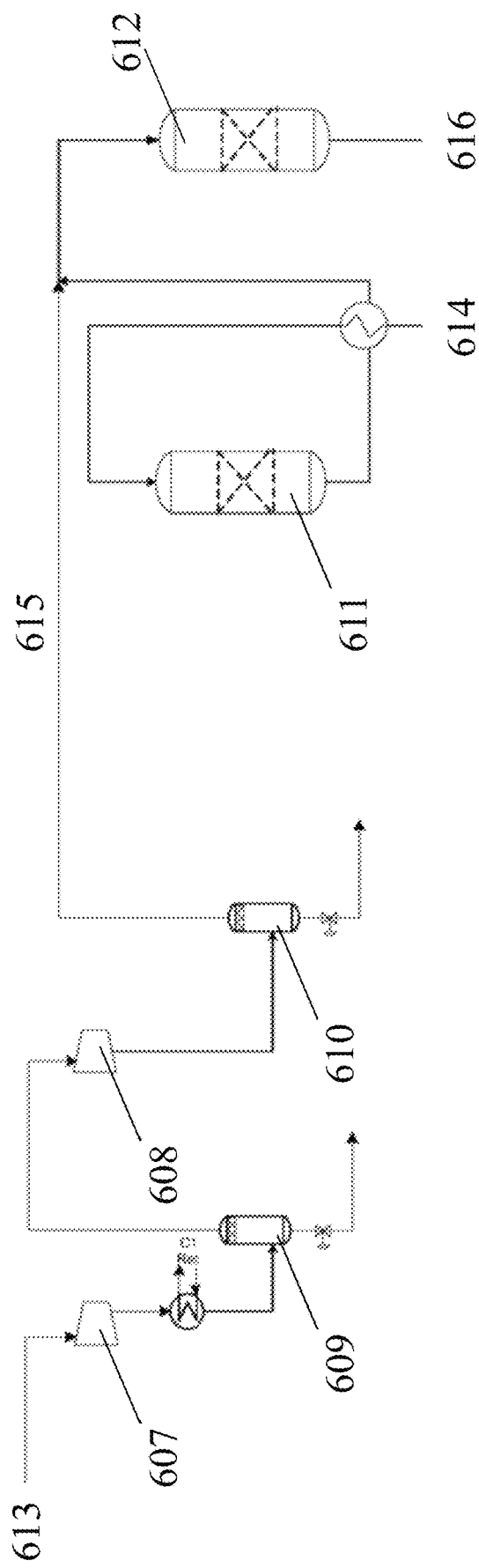

FIG. 6B is a process flow diagram of an example of a methanation system that can be employed to generate ethylene. The system of FIG. 6B can be used in other systems of the present disclosure, such as the system 100 of FIG. 1. The system comprises compressors 607 and 608, separation units 609 and 610, and methanation reactors 611 and 612. The separation units 609 and 610 can be quench towers, which may separate water from a stream comprising CO and/or $CO_2$. During use, a stream 613 comprising CO and/or $CO_2$ is directed to the compressor 607 and subsequently the separator unit 609. In stream 614, CO and/or $CO_2$ along with $H_2$ are directed to the methanation reactor 611 and are reacted to form methane, which, along with any excess CO, $CO_2$ and $H_2$, is subsequently directed to the methanation reactor 612, where CO and/or $CO_2$ provided in stream 615 is reacted with $H_2$ to form additional methane. The methane generated in the methanation reactors 611 and 612 is directed along stream 616. The methane in stream 616 can be, for example, recycled to an OCM reactor.

Use of methanation systems with OCM systems of the present disclosure can reduce the quantity CO and/or $CO_2$ that are directed to the environment, which may advantageously decrease overall greenhouse emissions from such systems. In some examples, using a methanation system, the emission of CO and/or $CO_2$ from an OCM system can be reduced by at least about 0.01%, 0.1%, 1%, 2%, 3%, 4%, 5%, 6%, 7%, 8%, 9%, 10%, 20%, 30%, 40%, or 50%.

The methanation reaction can be practiced over a nickel-based catalyst, such as those used to produce SNG (Substitute Natural Gas or Synthetic Natural Gas) from syngas or used to purify streams containing CO and $CO_2$ (e.g., to remove CO and $CO_2$ present in the make-up feed to an ammonia synthesis unit). Examples of such catalysts include the KATALCO™ series (including models 11-4, 11-4R, 11-4M and 11-4MR) that may include nickel supported on refractory oxides; the HTC series (including NI 500 RP 1.2) having nickel supported on alumina; and Type 146 having ruthenium supported on alumina. Additional methanation catalysts can include models PK-7R and METH-134. The methanation catalyst can be tableted or an extruded. The shapes of such catalysts can be, for example, cylindrical, spherical, or ring structures, for or partial shapes and/or combinations of shapes thereof. In some cases, ring structures are advantageous due to their reduced pressure drop across the reactor bed relative to cylindrical and spherical commercial forms. In some cases, the methanation catalyst is a doped or modified version of a commercially available catalyst.

In some cases, merely applying a methanation catalyst to the OCM process that has been developed or optimized for another process (e.g., SNG production or gas purification) can result in operational problems and/or non-optimal performance, including carbon formation (or coking) over the methanation catalyst. Coking can lead to de-activation of the catalyst and, eventually, to loss of conversion through the methanation reactor, thus making the methanation process ineffective, severely limiting the performances of the overall OCM-based process and, possibly, preventing the final products from achieving the required specifications.

The selectivity and/or conversion produced by an existing and/or commercially available methanation catalyst at a given process condition (e.g., gas-hourly space velocity, molar composition, temperature, pressure) may not be ideal for OCM implementations. For example, ammonia plants can have between about 100 ppm and 1% CO with a molar excess of $H_2$ (e.g., 2, 5, 10, 50, 100-fold or more excess) that drives equilibrium in favor of complete methanation. Methanation systems in ammonia plants have a small temperature difference between inlet and outlet of the adiabatic methanation reactor (e.g., 20 to 30° C.) and can be sized for catalyst lifetime. SNG production does not have a vast molar excess of $H_2$ in some cases. Methanation in SNG processes can have an inlet versus outlet temperature difference of greater than 100° C. and be performed in multiple stages. Furthermore, the purpose of methanation can be different for OCM. Ammonia and SNG processes typically perform methanation primarily to eliminate CO and/or $CO_2$ (although $H_2$ can also be eliminated or substantially reduced in concentration), while methanation is performed in OCM processes primarily to eliminate $H_2$ (although CO and/or $CO_2$ can also be eliminated or substantially reduced in concentration).

A methanation catalyst and/or catalytic process is described herein that can prevent or reduce carbon formation in the methanation reactor or other operational inefficiencies. The catalyst and/or catalytic process is achieved through any combination of: (a) removing chemical species that can contribute to coke formation from the methanation inlet feed; (b) introducing chemical species into the methanation feed that eliminate or reduce the rate of coke formation; and (c) using the methanation catalyst described herein that reduces or eliminates coke formation and/or is designed to operate at the process conditions of OCM effluent or OCM process streams (e.g., gas-hourly space velocity, molar composition, temperature, pressure).

In some instances, the species present in the OCM effluent stream that can lead to carbon formation in the methanation reactor are removed or reduced in concentration using a separations or reactive process. The typical operating conditions of a methanation reactor can be at a pressure between about 3 bar and about 50 bar and a temperature between about 150° C. and about 400° C. Any hydrocarbon species containing carbon-carbon double or triple bonds may be sufficiently reactive to form carbon deposits (i.e., coke). Examples of such species are acetylene, all olefins and aromatic compounds. Removal or significant reduction of these species can be achieved via different methods including, but not limited to: (a) hydrogenation (i.e., reaction of these species with the hydrogen present in the effluent stream itself to produce alkanes) over suitable catalysts prior to the methanation reactor; (b) condensation and separation of these species from methane prior to the methanation reactor; (c) absorption or adsorption of these species; (d) by utilizing suitable membranes; or (d) any combination thereof.

In some embodiments, species are introduced into the methanation inlet stream that eliminate or reduce the rate of carbon formation. Molecular species that can create a reducing atmosphere can be used to counteract an oxidation reaction and can therefore reduce the rate of carbon formation. Hydrogen and water are examples of these particular compounds and can be added to the OCM effluent stream prior to methanation to increase their concentration in the methanation reactor.

An aspect of the present disclosure provides a methanation catalyst for an OCM process. Coke formation is typically the product of surface driven reactions. Therefore, the methanation catalyst for OCM alters the local electronic environment around the active site of the catalyst. This can be done by changing the elemental composition (for example via post-impregnation doping, or creating a new mixed metal of nickel and another transition metal), morphology and structure (for example via synthesizing the metal in a non-bulk form factor). Examples of such syntheses include; nanowires of the same material, nanoparticles coated on a support, and vapor deposition of the active material on a support material. Additional modifications to the surface may result from post synthetic processing steps, such as etching of the surface, oxidizing and reducing the metal to create a different surface reconstruction, calcination steps under different atmospheres (e.g., oxidizing or reducing), heating to achieve different crystal phases, and inducing defect formation. The end result of the modifications of the methanation catalyst is specifically designed to minimize carbon (coke) formation, while still effectively at conducting the methanation reactions.

The methanation process and/or methanation catalyst can operate with OCM product gas, either directly or after one or more heat exchangers or separation operations. For example, the methanation feed stream can have the following composition on a molar basis: $CH_4$ between about 65% and about 90%; $H_2$ between about 5% and about 15%; CO between about 1% and about 5% (molar basis); $C_2H_4$ between about 0% and about 0.5%; $C_2H_2$ between about 0% and about 0.1%; and the balance inert gases such as $N_2$, Ar and He. The methanation feed stream typically has a temperature close to ambient temperature and a pressure ranging between about 3 and about 50 bar.

The methanation reaction can produce water and/or have water in the methanation effluent. In some cases, it is desirable to remove this water prior to recycling the methanation effluent to the OCM reactor. This can be accomplished by lowering the temperature of the methanation effluent or performing any separation procedure that removes the water. In some embodiments, at least about 70%, at least about 80%, at least about 70%, at least about 90%, at least about 95%, or at least about 99% of the water is removed from the methanation effluent prior to the OCM reactor. Removing the water can increase the lifetime and/or performance of the OCM catalyst.

A methanation process can be implemented in an OCM-based process using adiabatic reactors. In an example, the process does not require a methanation catalyst specially designed or optimized for OCM. In this example, an OCM-based process is designed to produce ethylene from natural gas. In this case the product and recovery section of the OCM plant (e.g., a cryogenic unit) can be designed to separate ethylene and all other hydrocarbons from methane, CO and $H_2$ in the OCM effluent. The mixed stream that contains methane, CO and $H_2$ can be fed to the methanation section.

Figure 7:
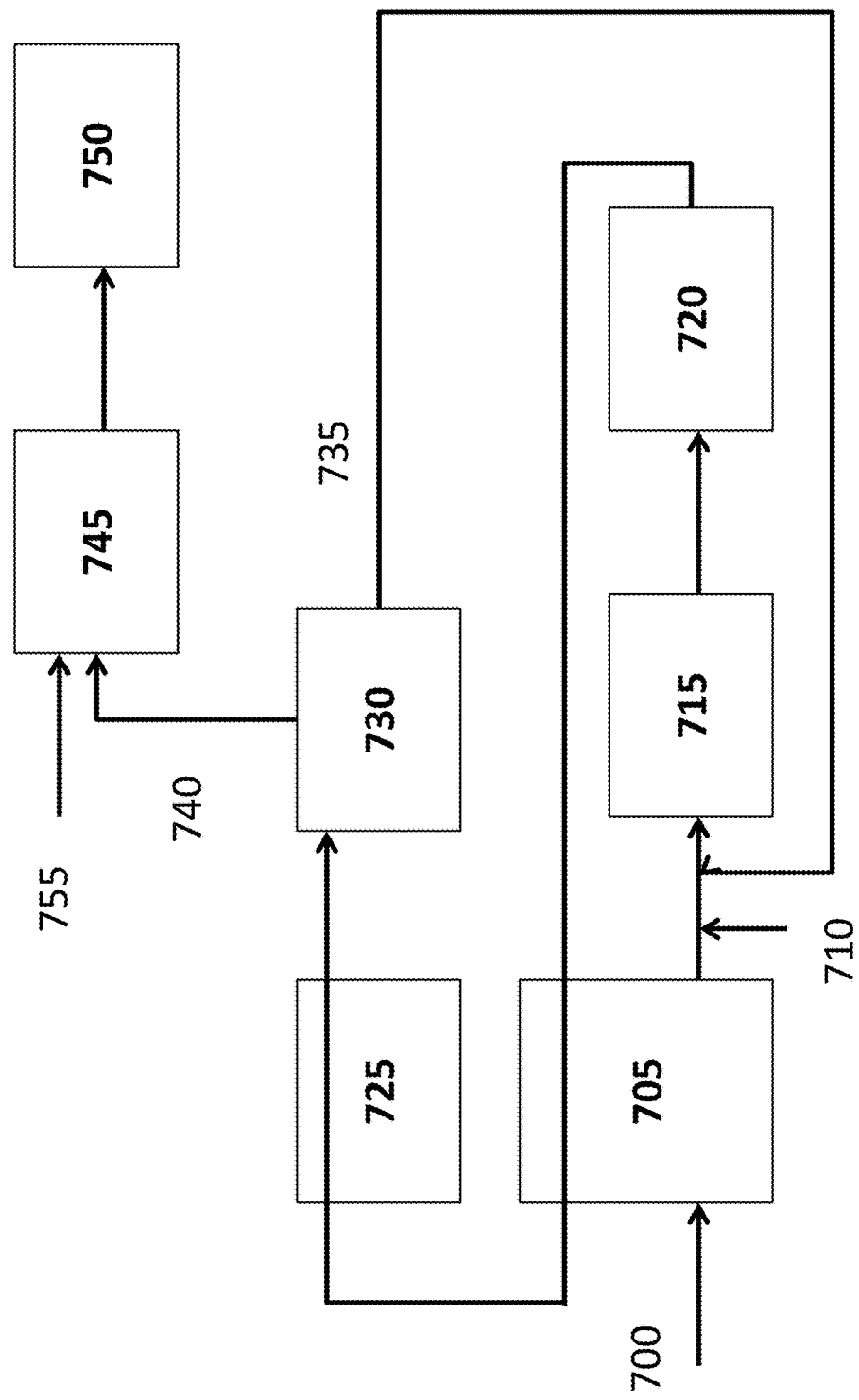
FIG. 7 shows an example of a methanation system for OCM.

FIG. 7 shows an example of a methanation system for OCM. The methanation feed stream 700 is first sent to a first heat exchanger 705 where its temperature is increased to the methanation reactor inlet temperature, typically between 150° C. and 300° C. Steam 710 is injected immediately downstream of the first heat exchanger to increase water concentration in the methanation feed stream. Then the heated stream is fed to a first adiabatic reactor 715 where ethylene, acetylene and any other hydrocarbon that presents carbon-carbon double or triple bonds are hydrogenated via reaction with the $H_2$ present in the stream.

The effluent from the first reactor 715 is then fed to a second reactor 720, where CO reacts with $H_2$ until a certain approach to equilibrium is achieved, typically 0° C.-15° C. to equilibrium. The adiabatic temperature increase that results from CO methanation depends on the exact composition of the feed stream and is typically in the 50° C.-150° C. range.

The second reactor 720 effluent is then sent to the first heat exchanger 705 and a second heat exchanger 725 where it is cooled down to a temperature below water condensation. The stream is then fed to a phase separator 730 where the condensed water 735 is separated from the vapors 740 in order to minimize the water concentration in the vapors. It can be important to remove water at this stage to optimize the conditions for the second methanation stage (water is a product of the methanation reaction and is no longer needed in the second stage because all carbon forming species have been either removed or converted at this point).

The vapor stream 740 is fed to a third heat exchanger 745 where it is heated up to the temperature required at the inlet of the third adiabatic reactor 750, which is the second methanation stage, typically operated at between about 150° C. and about 300° C. Additional $CO_2$ 755 produced in the process is mixed with effluent from the second reactor 720 and fed to the third reactor 750. CO and $CO_2$ react with $H_2$ in the third reactor 750 until a 0° C.-15° C. temperature approach to equilibrium is reached. Typically the amount of $CO_2$ that is added to the second reactor effluent is more than what may be stoichiometrically required to consume all $H_2$, to push the equilibrium towards CO and $H_2$ complete depletion.

The liquid stream from the phase separator 735 is re-injected into the methanation feed stream alongside the steam. Alternatively, it can be first vaporized and then re-injected, or it can be sent to a water treatment system for water recovery and purification.

The three reactors, 715, 720 and 750 or any combination of them can be physically situated in the same vessel or can be arranged in separate individual vessels. A portion or even all of the $CO_2$ addition may be performed at the inlet of 715 or 720, depending on the type of catalyst used in the two reactors.

OCM System Configurations

An OCM reactor system can comprise a single reactor or multiple reactors in series and/or in parallel. For example, the OCM reactor system includes at least 2, 3, 4, or 5 OCM reactors in series. As another example, the OCM reactor system includes at least 2, 3, 4, or 5 OCM reactors in parallel. As another example, the OCM reactor includes two OCM reactors in parallel, both of which are downstream of another OCM reactor. In some cases, an OCM reactor system can comprise two reactors, three reactors, or four reactors in series. In certain embodiments, the above mentioned number of reactors can be connected in parallel, or a combination thereof (e.g., mixed series and parallel). In addition, either one or more of the OCM reactor can contain a post-bed cracking (PBC) section as a part of the OCM reactor.

The OCM reaction is highly exothermic and the heat produced can be used to generate steam. A heat recovery system can be designed so as to cool down OCM reactor effluent to a temperature of less than or equal to about 600° C., 500° C., 400° C., 300° C. or 200° C., or a temperature between any two of these values (e.g., between 200° C. and 600° C., or 300° C. and 500° C.), and to use that heat as process heat within the OCM unit, to heat boiler feed water (BFW) or steam, or for other processes.

Figure 8A:
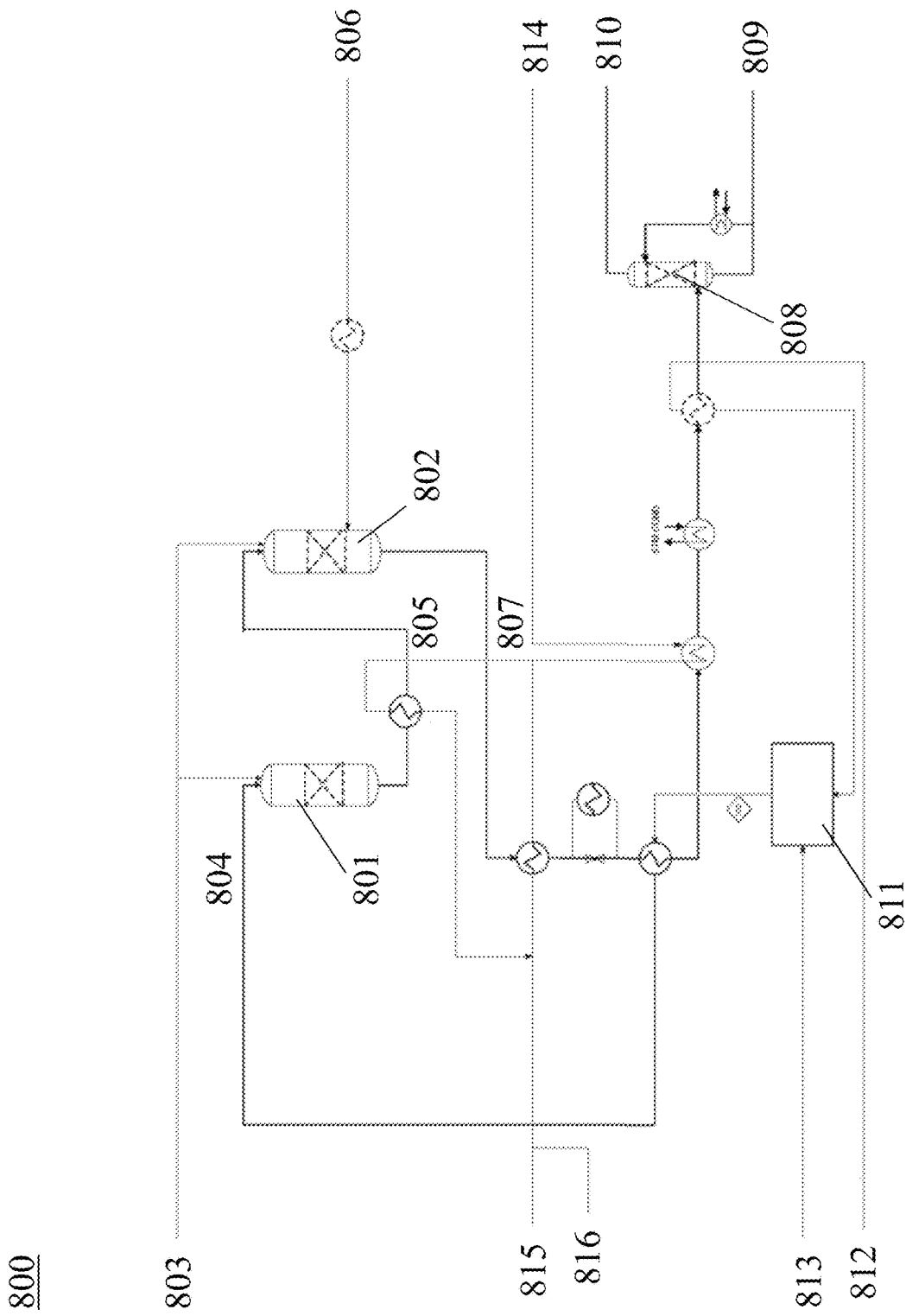
FIGS. 8A and 8B show an OCM system for world scale olefin production.
Figure 13:
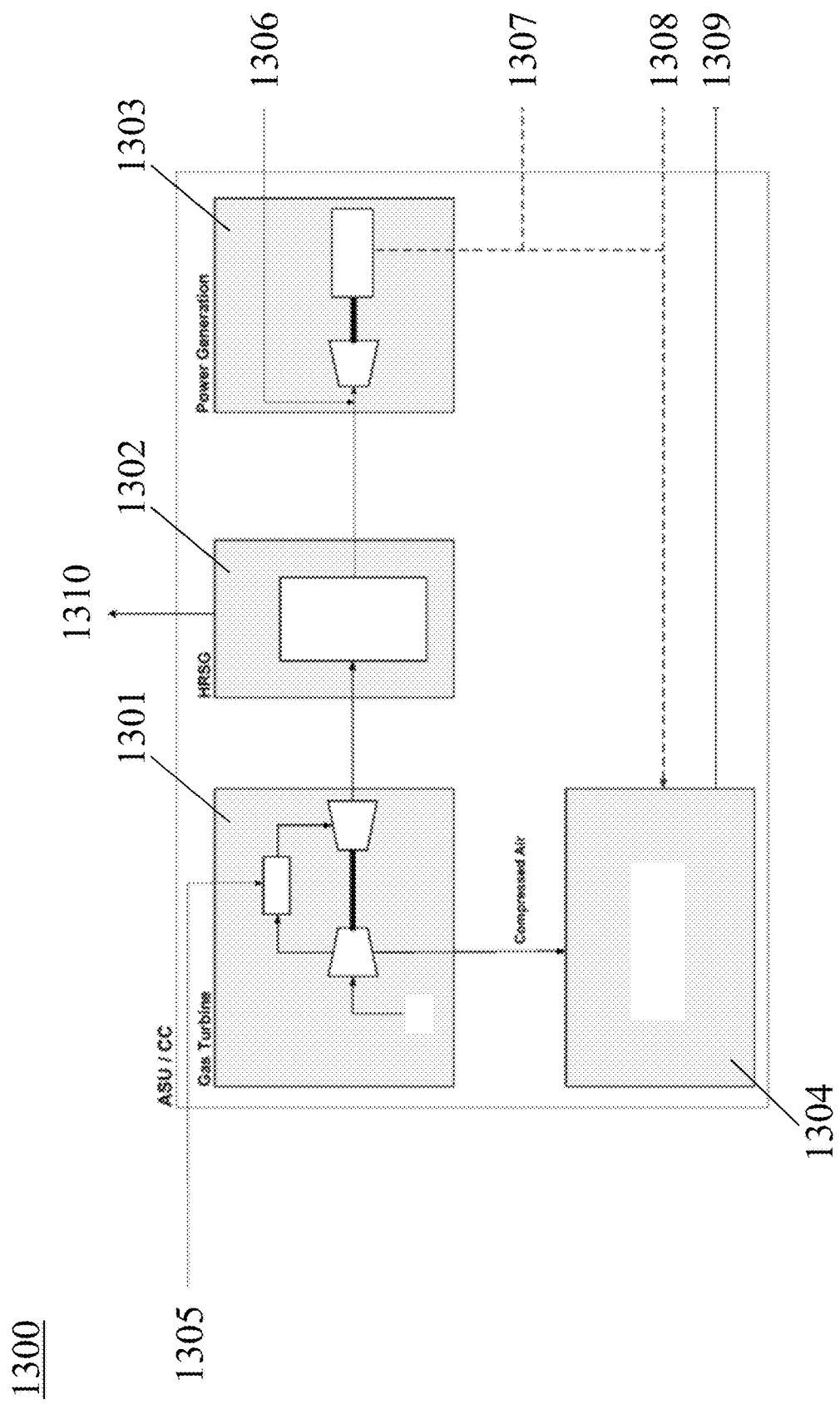
FIG. 13 shows a heat recovery steam generator system.

FIGS. 5, 8, and 13 show various sub-systems that may be suitable for use in a system that is configured for the production of ethylene at world scale. With reference to FIG. 8A, a system 800 comprises a first OCM unit 801 and second OCM unit 802. The OCM units 801 and 802 are in series—the second OCM unit 802 receives OCM effluent from the first OCM unit 801. Each OCM unit 801 and 802 includes and OCM reactor that is configured to react methane with an oxidizing agent to generate $C_{2+}$ compounds. One or both of the OCM units 801 and 802 can include a PBC reactor downstream of the OCM reactor. In the illustrated example, the second OCM unit 802 comprises a PBC reactor downstream of the OCM reactor of the second OCM unit 802.

During use, oxygen along stream 803 is directed into the OCM units 801 and 802. Methane is directed to the first OCM unit 801 along stream 804. In the first OCM unit 801, methane and oxygen react in an OCM process to yield an OCM effluent stream 805 that is directed to a heat exchanger and subsequently the second OCM unit 802. The second OCM unit 802 generates addition $C_{2+}$ compounds from oxygen and any unreacted methane in the stream 805. In addition, the second OCM unit 802 accepts ethane along stream 806 into the PCB reactor of the second OCM unit 802, and generates ethylene from the ethane. $C_{2+}$ compounds generated in the second OCM unit 802, along with any non-$C_{2+}$ impurities are directed out of the second OCM unit 802 along stream 807 to multiple heat exchangers and subsequently a separator 808, which removes water from the OCM effluent stream. Water is directed out of the separator 808 along stream 809, and $C_{2+}$ compounds and any non-$C_{2+}$ impurities are directed along stream 810.

The system 800 further includes a methanation unit 811 that generates methane from $H_2$ and CO and/or $CO_2$. Methane generated in the methanation unit 811 is directed along stream 804 to the first OCM unit 801. The methanation unit 811 may be as described elsewhere herein. Methane, such as recycled methane, is directed along stream 812 through a heat exchanger and to the methanation unit 811. CO and/or $CO_2$ are directed to the methanation unit 811 along stream 813.

The system 800 includes process stream that is used in the heat exchangers. Process steam is directed along stream 814 to various heat exchangers and is outputted along stream 815 and 816.

Although the system 800 includes two OCM units 801 and 802, the system 800 can include any number of OCM units in series and parallel. An OCM unit can be an OCM reactor with an OCM catalyst. The system 800 can include at least 1, 2, 3, 4, 5, 6, 7, 8, 9, or 10 OCM units.

The stream 810 may be directed to a hydrogenation reactor and separation train to convert any acetylene in the stream 810 to ethane and/or ethylene, and separate the ethane from ethylene. For world scale ethylene generation, the system 300 of FIG. 3 may be employed. A PSA unit may be used to separate $H_2$ from $N_2$ in a stream comprising $H_2$ and $N_2$.

Figure 8B:
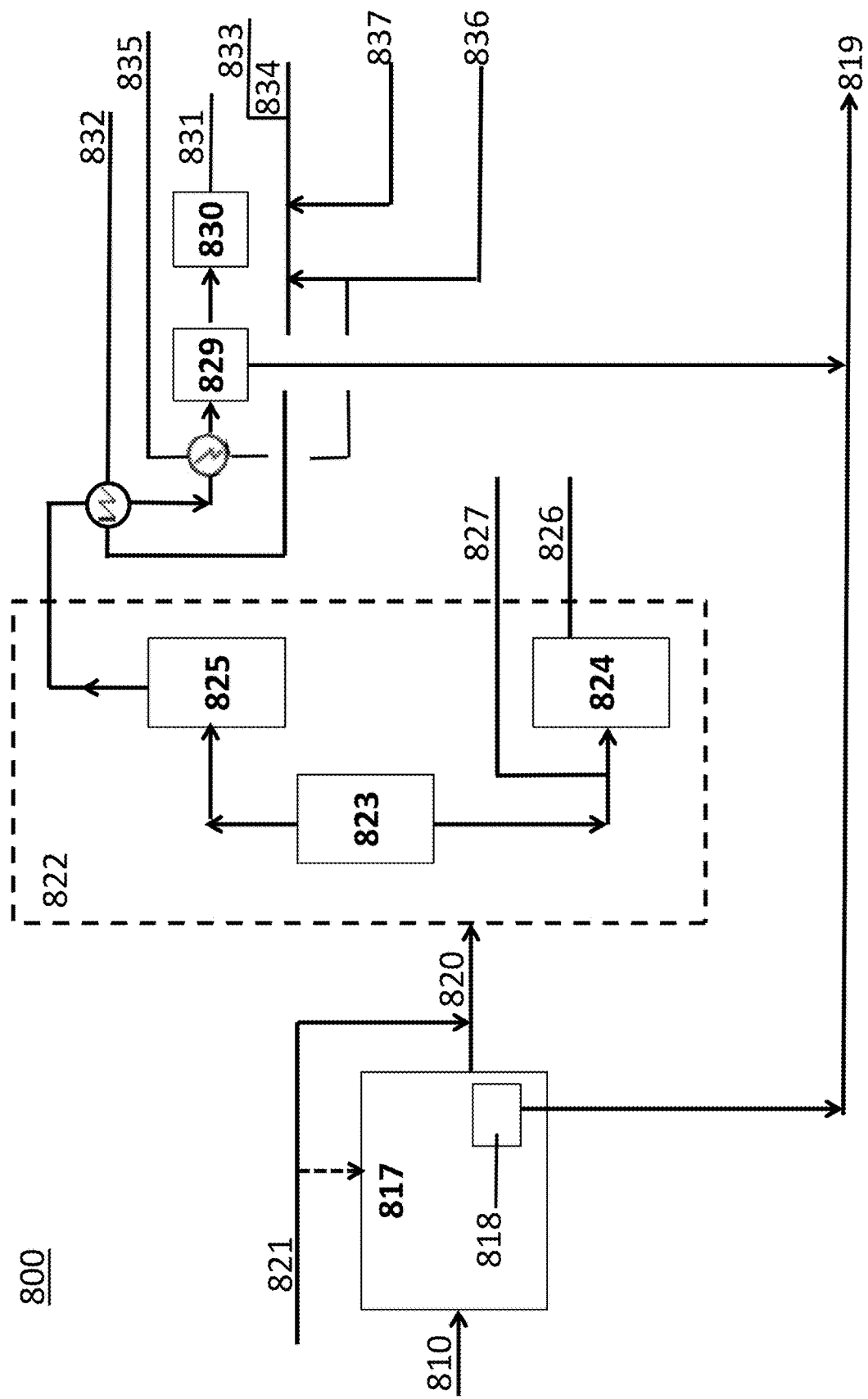

With reference to FIG. 8B, the stream 810 is directed into a series of compressors 817 and separators 818, which raise the pressure of the stream 810 (e.g., by a factor of from about 2.5:1 to 4:1) and remove water from the stream 810. The separators may be quench towers. Water removed from a first of the separators 818 is directed along stream 819. The pressurized stream 820 (which includes $C_{2+}$ compounds) can be mixed with methane from stream 821 (e.g., natural gas stream or methane from a methanation unit) and subsequently directed to an absorption system 822 for removing $CO_2$ from the stream 820. The absorption system 822 can be an amine system. The absorption system 822 comprises an absorption unit 823, a regenerator 824 and a scrubber 825. The absorption unit 823 can employ an aqueous solution of various akylamines (also "amines" herein) to scrub $CO_2$ and $H_2S$ from the stream 820. Examples of amines include, without limitation, diethanolamine, monoethanolamine, methyldiethanolamine and diisopropanolamine. The resultant "rich" amine is then routed into the regenerator 824 (e.g., a stripper with a reboiler) to produce regenerated or "lean" amine that is recycled for reuse in the absorption unit 823. The separated $CO_2$ can be purged 826 or recycled 827 (e.g., to a methanation system).

The absorption unit 823 generates an effluent stream that can have a low $CO_2$ content, which is directed to the scrubber 825. The scrubber 825 removes additional $CO_2$ from the stream, using, for example, a sodium hydroxide stream that is directed through the scrubber 825 in a counter flow configuration. The stream 828 is then directed from the scrubber 825 to a separator 829, which removes water from the stream 828. The removed water is directed along stream 819 and the $C_{2+}$ compounds and non-$C_{2+}$ impurities are directed to dryers 830, and subsequently directed along stream 831. The OCM effluent stream 828 may be cooled in a heat exchanger upon heat transfer to a $C_1$ recycle stream, for example.

The system of FIG. 8B employs various heat exchangers. A $C_1/N_2$ stream is directed along stream 832 to a heat exchanger and removed along streams 833 and 834. Process stream 835, which can comprise methane, is directed to another heat exchanger, and a portion of process stream 835 is then directed along stream 834 and a remainder is directed along stream 836. A $C_1$ purge from, for example, a PSA unit, may be directed along stream 837 to stream 834.

In FIGS. 8A-8B, in some examples, the separators 808 and 818 can be liquid/liquid separators or gas/liquid separators. For example, the separator 808 or 818 can be a gas/liquid separator.

One or more ethylene recovery sections (including, for example, separations units and cryogenic units) can comprise a series of fractionation towers to separate and recover products. The cooling to condense each of the column overhead vapors can be provided by multiple ways. The lowest temperature required is to condense demethanizer overhead vapors. In some cases, the demethanizer overhead vapor is expanded and the chill is utilized to cool the incoming feed streams.

A recycle split vapor (RSV) process can be employed. An RSV process can comprise a full RSV (modified for the OCM plant) with a propylene refrigerant, or a full three-refrigerant system typical of an ethylene plant (methane refrigerant, ethylene refrigerant and propylene refrigerant, or use a mixed refrigerant composed of two or more of these refrigerants). In some cases, a combination of these two options (i.e. RSV or modified RSV combined with utilization of one or more of the three typical refrigeration systems) can be used to provide for the refrigeration duty to the OCM system separation section.

In natural gas processing plants or NGLs fractionation unit, methane can be separated from ethane and higher carbon-content hydrocarbons (conventionally called natural gas liquids or NGLs) to produce a methane-rich stream that can meet the specifications of pipelines and sales gas. Such separation can be performed using cryogenic separation, such as with the aid of one or more cryogenic units, and/or by implementing one of the gas processing technologies (e.g., RSV) for maximum or optimum recovery of the NGLs.

The raw natural gas fed to gas processing plants can have a molar composition of 70% to 90% methane and 4% to 20% NGLs, the balance being inert gas(es) (e.g., $CO_2$ and $N_2$). The ratio of methane to ethane can be in the range of 5-25. Given the relatively large amount of methane present in the stream fed to cryogenic sections of gas processing plants, at least some or substantially all of the cooling duty required for the separation is provided by a variety of compression and expansion steps performed on the feed stream and the methane product stream. None or a limited portion of the cooling duty can be supplied by external refrigeration units.

There are various approaches for separating higher carbon alkanes (e.g., ethane) from natural gas, such as recycle split vapor (RSV) or any other gas processing technologies and/or gas sub-cooled process (GSP) processes, which may maximize the recovery of ethane (e.g., >99%, 98%, 97%, 96% or 95% recovery) while providing most or all of the cryogenic cooling duty via internal compression and expansion of portion of the natural gas itself (e.g., at least about 10%, 15%, 20%, 25%, 30%, 35%, 40%, or 50%). However, the application of such approach in separating alkenes (e.g., ethylene) from an OCM product stream comprising methane is novel and may result in a limited recovery in some cases when inert gas in present (e.g., provide less than 95% recovery) of the alkene product, due at least in part to i) the different vapor pressure of alkenes and alkanes, and/or ii) the presence of significant amounts of $H_2$ in the OCM product stream, which can change the boiling curve and, particularly, the Joule-Thomson coefficient of the methane stream that needs to be compressed and expanded to provide the cooling duty. Hydrogen can display a negative or substantially low Joule-Thomson coefficient, which can cause a temperature increase or a substantially low temperature decrease in temperature when a hydrogen-reach stream is expanded.

In some embodiments, the design of a cryogenic separation system of an OCM-based plant can feature a different combination of compression/expansion steps for internal refrigeration and, in some cases, external refrigeration. The present disclosure provides a separation system comprising one or more cryogenic separation units and one or more demethanizer units. Such a system can maximize alkene recovery (e.g., provide greater than 95% recovery) from a stream comprising a mixture of alkanes, alkenes, and other gases (e.g., $H_2$), such as in an OCM product stream.

In such separation system, the cooling duty can be supplied by a combination of expansion of the OCM effluent (feed stream to the cryogenic section) when the OCM effluent pressure is higher than a demethanizer column; expansion of at least a portion or all of the demethanizer overhead methane-rich stream; compression and expansion of a portion of the demethanizer overhead methane-rich stream; and/or external propane, propylene or ethylene refrigeration units.

Figure 9:
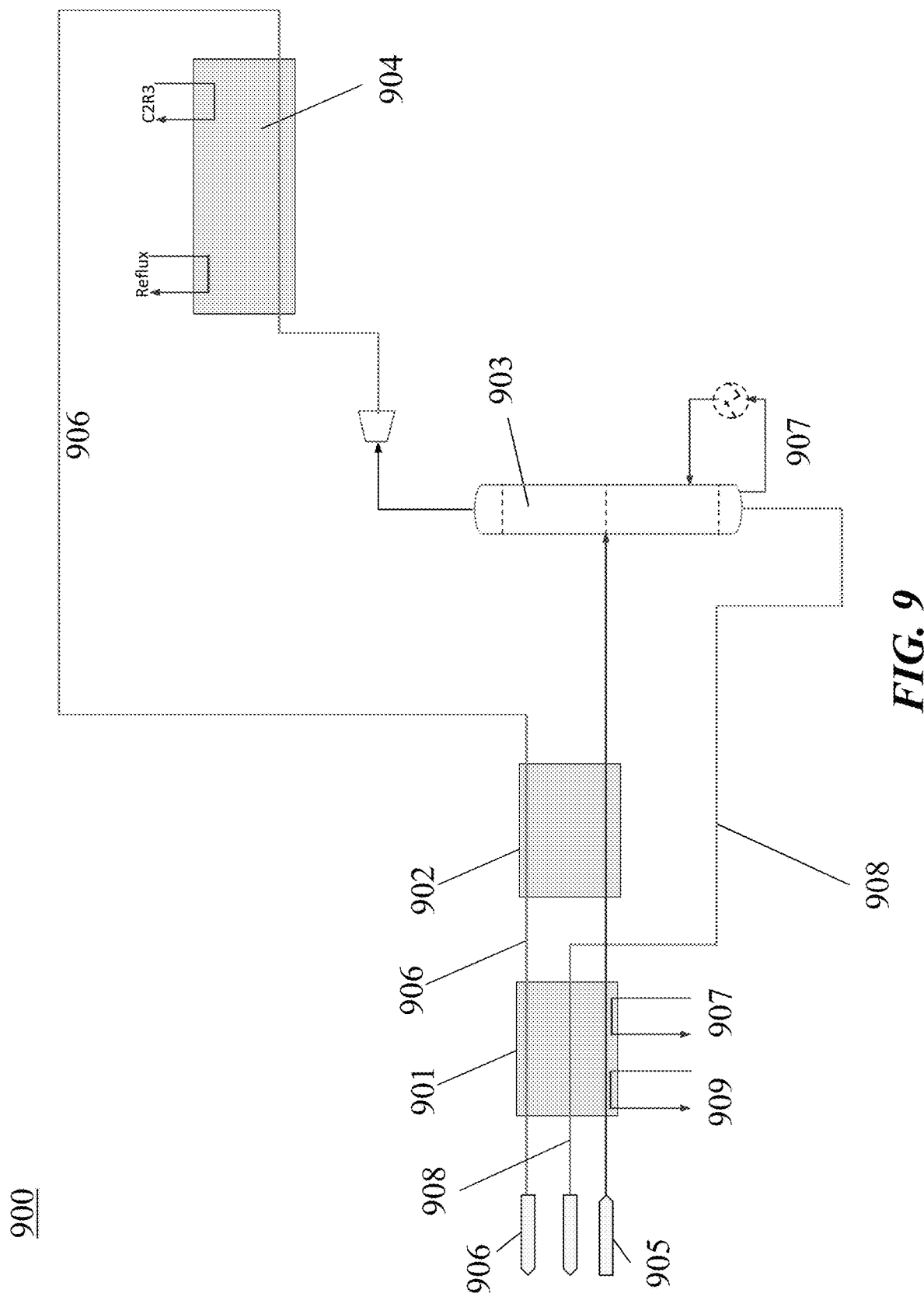
FIG. 9 shows a separation system that may be employed for use with systems and methods of the present disclosure.

FIGS. 9-12 show various separation systems that can be employed with various systems and methods of the present disclosure, including small scale and world scale systems. FIG. 9 shows a separation system 900 comprising a first heat exchanger 901, a second heat exchanger 902, a demethanizer 903, and a third heat exchanger 904. The direction of fluid flow is shown in the figure. The demethanizer 903 can be a distillation unit or multiple distillation units (e.g., in series). In such a case, the demethanizer can include a reboiler and a condenser, each of which can be a heat exchanger. An OCM effluent stream 905 is directed to the first heat exchanger 901 at a pressure from about 10 to 100 bar (absolute), or 20 to 40 bar. The OCM effluent stream 905 can include methane and $C_{2+}$ compounds, and may be provided in an OCM product stream from an OCM reactor (not shown). The OCM effluent stream 905 is then directed from the first heat exchanger 901 to the second heat exchanger 902. In the first heat exchanger 901 and the second heat exchanger 902, the OCM effluent stream 905 is cooled upon heat transfer to a demethanizer overhead stream 906, a demethanizer reboiler stream 907, a demethanizer bottom product stream 908, and a refrigeration stream 909 having a heat exchange fluid comprising propane or an equivalent cooling medium, such as, but not limited to, propylene or a mixture of propane and propylene.

The cooled OCM effluent 905 can be directed to the demethanizer 903, where light components, such as $CH_4$, $H_2$ and CO, are separated from heavier components, such as ethane, ethylene, propane, propylene and any other less volatile component present in the OCM effluent stream 905. The light components are directed out of the demethanizer along the overhead stream 906. The heavier components are directed out of the demethanizer along the bottom product stream 908. The demethanizer can be designed such that at least about 60%, 70%, 80%, 90%, or 95% of the ethylene in the OCM effluent stream 905 is directed to the bottom product stream 908.

The demethanizer overhead stream 906 can contain at least 60%, 65%, 70%, 75%, or 80% methane. The overhead stream 906 can be expanded (e.g., in a turbo-expander or similar machine or flashed over a valve or similar device) to decrease the temperature of the overhead stream 906 prior to directing the overhead stream 906 to the second heat exchanger 902 and subsequently the first heat exchanger 901. The overhead stream 906 can be cooled in the third heat exchanger 904, which can be cooled using a reflux stream and a hydrocarbon-containing cooling fluid, such as, for example, ethylene.

The overhead stream 906, which can include methane, can be recycled to an OCM reactor and/or directed for other uses, such as a natural gas pipeline. In some examples, the bottom product stream, which can contain $C_{2+}$ compounds (e.g., ethylene), can be directed to an ETL system.

Figure 10:
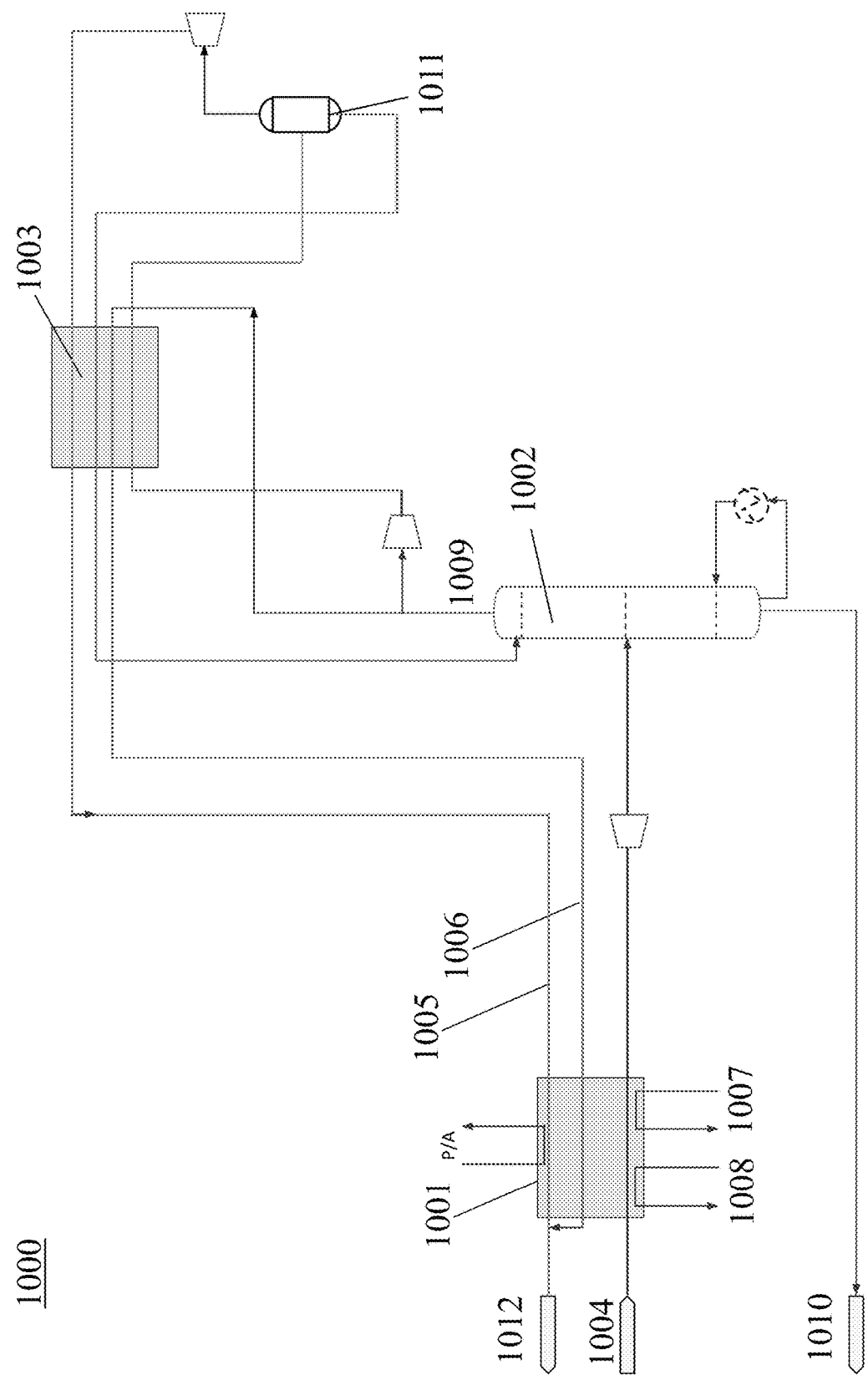
FIG. 10 shows another separation system that may be employed for use with systems and methods of the present disclosure.

FIG. 10 shows another separation system 1000 that may be employed for use with systems and methods of the present disclosure. The direction of fluid flow is shown in the figure. The system 1000 comprises a first heat exchanger 1001, demethanizer 1002 and a second heat exchanger 1003. The demethanizer 1002 can be a distillation unit or multiple distillation units (e.g., in series). An OCM effluent stream 1004 is directed into the first heat exchanger 1001. The OCM effluent stream 1004 can include methane and $C_{2+}$ compounds, and may be provided in an OCM product stream from an OCM reactor (not shown). The OCM effluent stream 1004 can be provided at a pressure from about 10 bar (absolute) to 100 bar, or 40 bar to 70 bar. The OCM effluent stream 1004 can be cooled upon heat transfer to a demethanizer overhead streams 1005 and 1006 from the second heat exchanger 1003, a demethanizer reboiler stream 1007, and a refrigeration stream having a cooling fluid comprising, for example, propane or an equivalent cooling medium, such as, but not limited to, propylene or a mixture of propane and propylene. In some cases, the demethanizer overhead streams 1005 and 1006 are combined into an output stream 1012 before or after passing through the first heat exchanger 1001.

Subsequent to cooling in the first heat exchanger 1001, the OCM effluent stream 1004 can be expanded in a turbo-expander or similar device or flashed over a valve or similar device to a pressure of at least about 5 bar, 6 bar, 7 bar, 8 bar, 9 bar, or 10 bar. The cooled OCM effluent stream 1004 can then be directed to the demethanizer 1002, where light components (e.g., $CH_4$, $H_2$ and CO) are separated from heavier components (e.g., ethane, ethylene, propane, propylene and any other less volatile component present in the OCM effluent stream 1004). The light components are directed to an overhead stream 1009 while the heavier components (e.g., $C_{2+}$) are directed along a bottoms stream 1010. A portion of the overhead stream 1009 is directed to second heat exchanger 1003 and subsequently to the first heat exchanger 1001 along stream 1006. A remainder of the overhead stream 1009 is pressurized (i.e., pressure is increased) in a compressor and directed to the second heat exchanger 1003. The remainder of the overhead stream 1009 is then directed to a phase separation unit 1011 (e.g., distillation unit or vapor-liquid separator). Liquids from the phase separation unit 1011 are directed to the second heat exchanger 1003 and subsequently returned to the demethanizer 1002. Vapors from the phase separation unit 1011 are expanded (e.g., in a turbo-expander or similar device) and directed to the second heat exchanger 1003, and thereafter to the first heat exchanger along stream 1005. The demethanizer 1002 can be designed such that at least about 60%, 70%, 80%, 90%, or 95% of the ethylene in the OCM effluent stream 1004 is directed to the bottom product stream 1010.

Figure 11:
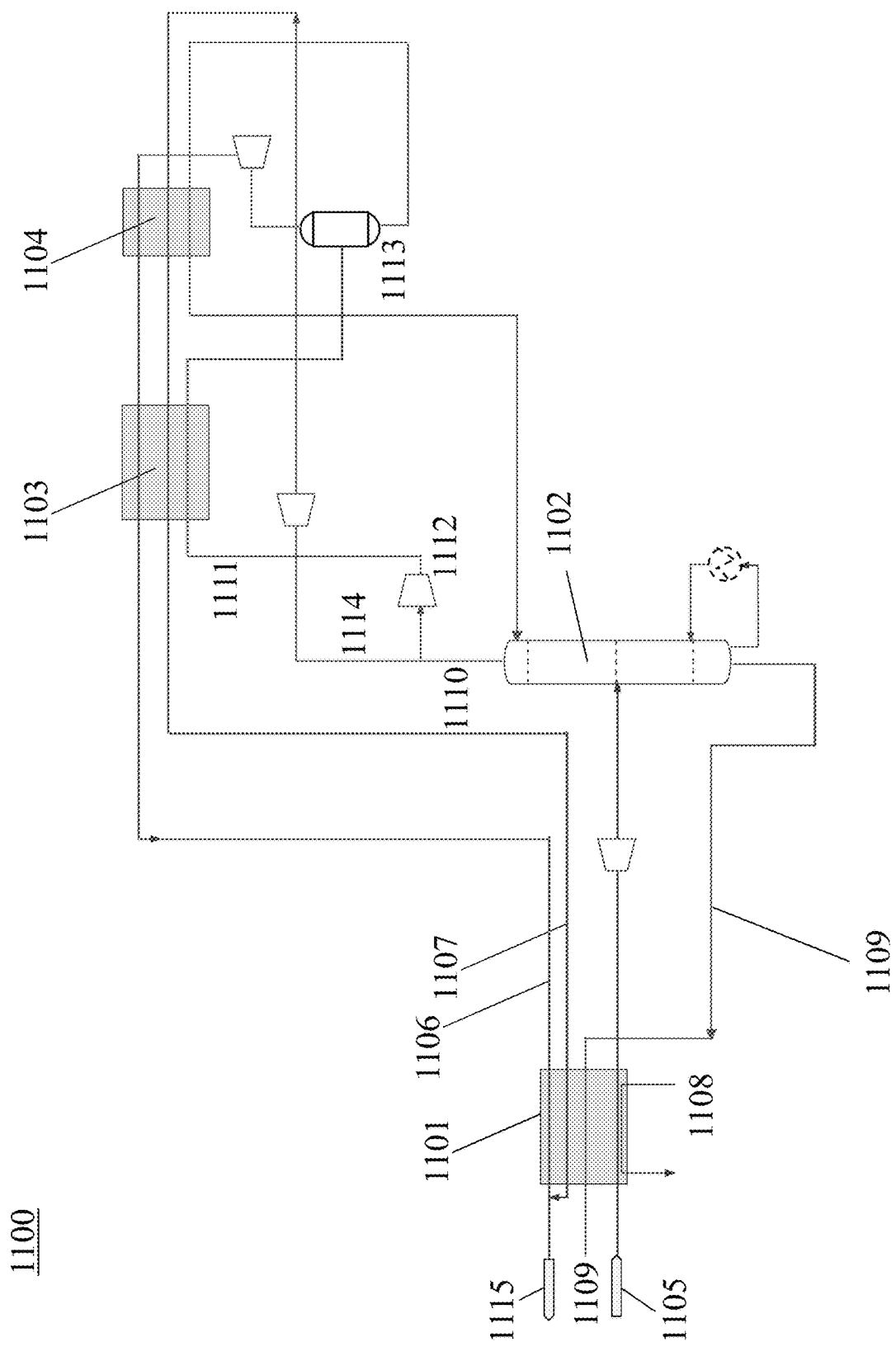
FIG. 11 shows another separation system that may be employed for use with systems and methods of the present disclosure.

FIG. 11 shows another separation system 1100 that may be employed for use with systems and methods of the present disclosure. The direction of fluid flow is shown in the figure. The system 1100 comprises a first heat exchanger 1101, a demethanizer 1102, a second heat exchanger 1103 and a third heat exchanger 1104. The system 1100 may not require any external refrigeration. The demethanizer 1102 can be a distillation unit or multiple distillation units (e.g., in series). An OCM effluent stream 1105 is directed to the first heat exchanger 1101 at a pressure from about 10 bar (absolute) to 100 bar, or 40 bar to 70 bar. In the first heat exchanger 1101, the OCM effluent stream 1105 can be cooled upon heat transfer to demethanizer overhead streams 1106 and 1107, a demethanizer reboiler stream 1108 and a demethanizer bottom product stream 1109. In some cases, the demethanizer overhead streams 1106 and 1107 are combined into a common stream 1115 before or after they are passed through the first heat exchanger 1101. The OCM effluent stream 1105 is then expanded to a pressure of at least about 5 bar, 6 bar, 7 bar, 8 bar, 9 bar, 10 bar, or 15 bar, such as, for example, in a turbo-expander or similar machine or flashed over a valve or similar device. The cooled OCM effluent stream 1105 is then directed to the demethanizer 1102, where light components (e.g., $CH_4$, $H_2$ and CO) are separated from heavier components (e.g., ethane, ethylene, propane, propylene and any other less volatile component present in the OCM effluent stream 1105). The light components are directed to an overhead stream 1110 while the heavier components are directed along the bottom product stream 1109. The demethanizer 1102 can be designed such that at least about 60%, 70%, 80%, 90%, or 95% of the ethylene in the OCM effluent stream 1105 is directed to the bottom product stream 1109.

The demethanizer overhead stream 1110, which can contain at least 50%, 60%, or 70% methane, can be divided into two streams. A first stream 1111 is compressed in compressor 1112 and cooled in the second heat exchanger 1103 and phase separated in a phase separation unit 1113 (e.g., vapor-liquid separator or distillation column). Vapors from the phase separation unit 1113 are expanded (e.g., in a turbo-expander or similar device) to provide part of the cooling duty required in heat exchangers 1101, 1103 and 1104. Liquids from the phase separation unit 1113 are sub-cooled in the third heat exchanger 1104 and recycled to the demethanizer 1102. A second stream 1114 from the overhead stream 1110 can be expanded (e.g., in a turbo-expander or similar device) to decrease its temperature and provide additional cooling to the heat exchangers 1101, 1103 and 1104.

Figure 12:
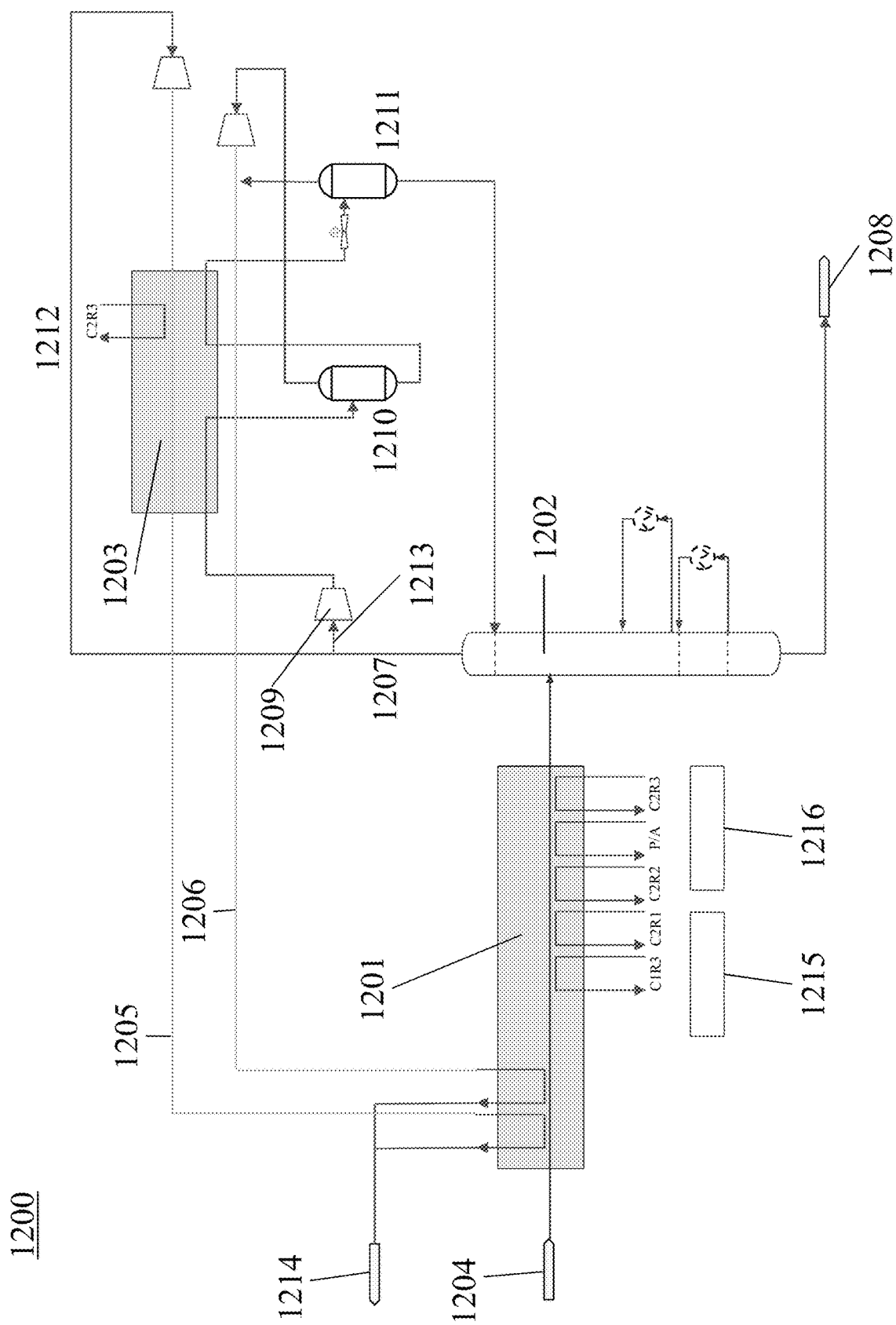
FIG. 12 shows another separation system that may be employed for use with systems and methods of the present disclosure.

FIG. 12 shows another separation system 1200 that may be employed for use with systems and methods of the present disclosure. The direction of fluid flow is shown in the figure. The system 1200 comprises a first heat exchanger 1201, a demethanizer 1202, and a second heat exchanger 1203. An OCM effluent stream 1204 is directed to the first heat exchanger 1201 at a pressure from about 2 bar (absolute) to 100 bar, or 3 bar to 10 bar. The first heat exchanger 1201 can interface with a propane refrigeration unit 1215 and/or an ethylene refrigeration unit 1216. In the first heat exchanger 1201, the OCM effluent stream 1204 can be cooled upon heat transfer to demethanizer overhead streams 1205 and 1206, a demethanizer reboiler stream, a demethanizer pump-around stream, and various levels of external refrigeration, such as using cooling fluids comprising ethylene and propylene. In some cases, the demethanizer overhead streams 1205 and 1206 are combined into a single stream 1214 before or after they are cooled. The cooled OCM effluent stream 1204 is then directed to the demethanizer 1202, where light components (e.g., $CH_4$, $H_2$ and CO) are separated from heavier components (e.g., ethane, ethylene, propane, propylene and any other less volatile component present in the OCM effluent stream 1204). The light components are directed to an overhead stream 1207 and the heavier components are directed along a bottom product stream 1208. The demethanizer 1202 can be designed such that at least about 60%, 70%, 80%, 90%, or 95% of the ethylene in the OCM effluent stream 1204 is directed to the bottom product stream 1208.

The demethanizer overhead stream, which can contain at least about 50%, 60%, 70%, or 80% methane, can be divided into two streams. A first stream 1213 can be compressed in a compressor 1209, cooled in the second heat exchanger 1203 and phase-separated in a phase separation unit 1210 (e.g., distillation column or vapor-liquid separator). Vapors from the phase separation unit 1210 can be expanded (e.g., in a turbo-expander or similar device) to provide part of the cooling duty required for the heat exchanger 1201 and 1203. Liquids from the phase separation unit 1210 can be sub-cooled and flashed (e.g., over a valve or similar device), and the resulting two-phase stream is separated in an additional phase separation unit 1211. Liquids from the additional phase separation unit 1211 are recycled to the demethanizer 1202 and vapors from the additional phase separation unit are mixed with expanded vapors from the phase separation unit 1210 prior to being directed to the second heat exchanger 1203.

A second stream 1212 from the overhead stream 1207 can be expanded (e.g., in a turbo-expander or similar device) to decrease its temperature and provide additional cooling for the heat exchanger 1201 and 1203. Any additional cooling that may be required for the second heat exchanger 1203 can be provided by an external refrigeration system, which may employ a cooling fluid comprising ethylene or an equivalent cooling medium.

In some cases, recycle split vapor (RSV) separation can be performed in combination with demethanization. In such a case, at least a portion of the overhead stream from a demethanizer unit (or column) may be split into at least two streams (see, e.g., FIGS. 10-12). At least one of the at least two streams may be pressurized, such as in a compressor, and directed to a heat exchanger.

In some instances, the methane undergoes an OCM and/or ETL process to produce liquid fuel or aromatic compounds (e.g., higher hydrocarbon liquids) and contains molecules that have gone through methanation. In some embodiments, the compounds have been through a recycle split vapor (RSV) separation process. In some cases, alkanes (e.g., ethane, propane, butane) are cracked in a post-bed cracker.

It will be appreciated that systems and methods described herein are provided as examples and that various alternatives may be employed. It will be further appreciated that components of systems described herein are interchangeable. For instance, components for use in small scale production may be employed for use in world scale production, and vice versa.

Air Separation Units (ASU) and Power Production

An OCM reaction can convert a natural gas into a stream containing ethane, ethylene and other short olefins and alkanes, such as propene and propane. Unlike conventional (i.e., non-OCM) cracking-based production technologies for olefin production which may utilize energy to sustain the cracking reaction, the OCM process can generate power from the exothermic OCM reaction itself. Provided herein are systems and methods that can utilize the OCM reaction heat for steam generation, which in turn can be exploited for power generation.

In an OCM process, methane can react with an oxidizing agent such as oxygen over an OCM catalyst to generate ethylene. A wide set of competitive reactions can occur simultaneously over the OCM catalyst, including combustion of both methane and partial oxidations. Natural gas can be the source of methane, and can be combined with one or more recycle streams coming from downstream separation units (e.g., which can contain methane and ethane). Air, enriched air or pure oxygen can be used to supply the oxygen required for the reaction. All these reactions are exothermic and the relevant reaction heat can be recovered in order to cool the reactor effluent and feed the effluent to a downstream compressor, which can then send the effluent stream to downstream separation and recovery units.

Several process configurations can be adopted to enable the efficient recovery of the reaction heat. In some cases, the process utilizes the OCM reaction heat to i) supply the heat for the endothermic cracking reactions that convert the additional ethane feed to ethylene; and ii) generate steam to drive a downstream compressor. This process can achieve energy neutrality (no need for energy import or export to conduct the overall process), however it can require a relatively large number of unit operations which can lead to operational complexity, large capital costs and high pressure drops between the reactor outlet and the compressor suction. When the OCM process is combined with power generation, the integrated OCM-power process can be a simpler and more efficient process when compared to an individual OCM process and a separate power production unit producing the same amounts of ethylene and power.

This flexibility and synergy between olefin and power production can be exploited as a design feature and/or an operating feature. That is, the process configuration of an integrated OCM-power system can be designed in order to maximize ethylene production, or power production, or for any intermediate level of production of the two products. In the case of maximum ethylene production, the flow of the ethane stream injected into the OCM reactor can be maximized to conduct cracking reactions to the maximum allowable extent. If the OCM reactor is adiabatic, the maximum extent of cracking corresponds to designing the system to crack an amount of ethane that results in a decrease in temperature to the minimum viable temperature for cracking. In the case of maximum power production, the system can be designed for minimum ethane injection, which can be limited by the highest possible temperature at the outlet of the OCM reactor and, accordingly, the maximum amount of steam generation. The combined OCM-power system can be designed to operate at any level of power and olefin production in between these two constraints.

The same flexibility and synergy between ethylene and power production can be achieved at an operating level. For example, the combined OCM-power process can be designed to handle both the maximum olefin and the maximum power cases. In such cases, the plant operator has the ability to change the amount of ethylene and power production during operations by deciding at any given time the amount of ethane to be injected into the OCM reactor. This operating feature can be particularly advantageous for optimizing the financial performance of the plant once it is built because it can allow variation of the composition of the product portfolio at any given time based on the real time prices of the respective products.

An aspect of the present disclosure provides an oxidative coupling of methane (OCM) system for production of olefins and power. The system can include an OCM subsystem that takes as input a feed stream comprising methane ($CH_4$) and a feed stream comprising an oxidizing agent such as oxygen, and generates a product stream comprising $C_{2+}$ compounds and heat from the methane and the oxidizing agent. The system can further include a power subsystem fluidically or thermally coupled to the OCM subsystem that converts the heat into electrical power.

The OCM subsystem can have at least one OCM reactor and at least one post-bed cracking unit within the OCM reactor or downstream of the OCM reactor. The post-bed cracking unit can be configured to convert at least a portion of alkanes in the product stream to alkenes. In some cases, the power subsystem has one or more turbines and can be a gas turbine combined cycle (GTCC). In some embodiments, the system further comprises a heat recovery steam generator (e.g., HRSG) for generating steam from the heat and the steam can be converted to electrical power in the power subsystem. In some instances, the power subsystem comprises a gas turbine and un-reacted methane from the OCM subsystem is converted to electrical power using the gas turbine.

Another aspect of the present disclosure provides a method for producing at least one $C_{2+}$ alkene and power. The method can include directing methane and an oxidizing agent into a reactor comprising a catalyst unit, where the catalyst unit comprises an oxidative coupling of methane (OCM) catalyst that facilitates an OCM reaction that produces $C_{2+}$ alkene. The method can include reacting the methane and oxidizing agent with the aid of the OCM catalyst to generate at least one OCM product comprising at least one $C_{2+}$ compound and heat. Electrical power can be generated from the heat.

In some cases, the heat is converted to steam and the steam is converted to power in a steam turbine. In some cases, un-reacted methane from the reactor is converted to electrical power in a gas turbine. In some instances, the reactor includes a cracking unit downstream of the catalyst unit, where the cracking unit generates $C_{2+}$ alkene from $C_{2+}$ alkane. The method can further include providing at least one hydrocarbon-containing stream that is directed through the cracking unit, which hydrocarbon-containing stream has at least one $C_{2+}$ alkane. At least one $C_{2+}$ alkane can be cracked to provide the at least one $C_{2+}$ alkene in a product stream that is directed out of the reactor. In some embodiments, the hydrocarbon-containing stream comprises at least one OCM product. The $C_{2+}$ alkene produced from the hydrocarbon-containing stream in the cracking unit can be in addition to the $C_{2+}$ alkene produced from the methane and the oxidizing agent in the reactor. In some embodiments, the amount of steam produced is varied or the amount of at least one hydrocarbon-containing stream that is directed through the cracking unit is varied to alter the amount of electrical power produced and the amount of $C_{2+}$ alkene produced.

FIG. 13 shows an example of a HRSG system 1300 that may be employed for use as the HRSG 507. The HRSG system 1300 comprises a gas turbine 1301, HRSG 1302, power generation unit 1303 and an air separation unit (ASU) 1304. The system 1300 comprises streams 1305, 1306, 1309 and 1310.

During use, the HRSG 1302 can transfer heat to a methane-containing stream (e.g., methane-containing stream 505). Purge gas from an OCM process can be burned to compress air as feed to ASU unit 1304. Additional high pressure steam may be provided along stream 1306. Power generated by the power generation unit 1303 can be directed to an OCM system 1307, an energy storage unit or power distribution system 1308, and/or the ASU 1304. The air separation unit accepts compressed air from the gas turbine 1301 and separates the compressed air to $O_2$ that is directed along stream 1309 and $N_2$, which can be purged. The HRSG system 1300 further comprises a purge stream 1305 that is directed into the gas turbine, and a flue gas stream 1310 that is directed out of the HRSG 1302.

Figure 14:
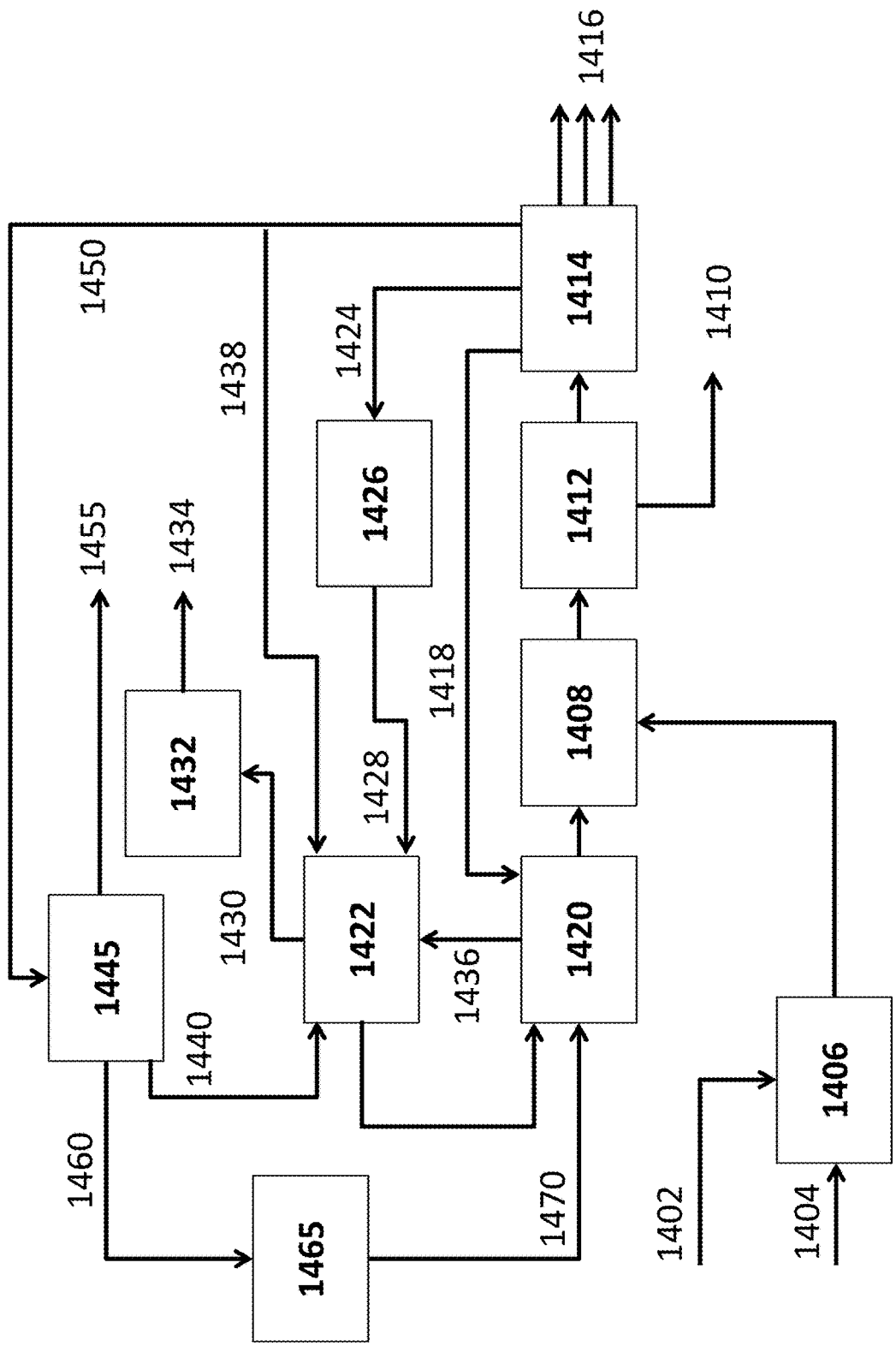
FIG. 14 shows an example of an OCM system that produces power.

FIG. 14 shows an example of an OCM process for producing ethylene and power. Natural gas 1402 and in some cases, additional ethane 1404, can be cleaned of sulfur-containing compounds in a de-sulfurization unit 1406 and fed into a process gas compressor 1408. Carbon dioxide ($CO_2$) 1410 can be removed in a process gas cleanup module 1412 and fed to the methanation reactor 1426 (connection not shown). The gas cleaned of $CO_2$ can be fed into a separations module 1414 where one or more product fractions 1416 can be isolated (e.g., $C_2$, $C_3$, $C_{4+}$ compounds).

Alkanes such as ethane can be recycled 1418 from the separations module to the OCM reactor 1420, where they can be injected into the post-bed cracking region of the reactor to generate olefins from the alkanes. The alkane recycle stream 1418 can be heated in a heat exchanger or a heat recovery steam generator (HRSG) 1422 (for simplicity, connection to HRSG not shown). Carbon monoxide 1424 from the separations module 1414 and carbon dioxide from module 1412 (connection not shown) can be fed into a methanation reactor 1426 along with hydrogen 1424 for conversion to methane. The methane recycle 1428 can be heated in the HRSG 1422 and returned to the OCM reactor 1420.

The HRSG can provide high-pressure steam 1430 to a steam turbine 1432 to produce power 1434. The steam and energy to heat the steam can be sourced from any suitable part of the process including from the OCM reactor 1436. Additional sources of steam and/or heat can include from combustion of fuel gas 1438 provided from the separations module, from the exhaust 1440 from a gas turbine 1445, and/or from cooling the effluent from the OCM reactor 1420 (not shown). Additional fuel gas 1450 can be provided to the gas turbine 1445. The gas turbine can produce electrical power 1455 and can drive a compressor (e.g., on the same shaft with the power generator) to supply compressed air 1460 for an air separation unit (ASU) 1465 or a vacuum pressure swing adsorption (VPSA) unit to supply oxygen to the OCM reactor 1420.

The combined OCM-power process shown in FIG. 14 can have numerous advantages over processes without power integration (e.g., FIGS. 26-31). For example, the total number of unit operations can be lower due to the heat recovery section of the combined cycle GTCC (that recovers the heat from the gas turbine exhaust) being utilized for OCM-related services, thus making a feed-product exchanger and a steam superheater redundant. The lower number of unit operations can lead to lower capital cost and operational simplicity. The pressure drop from the OCM reactor outlet to the compressor suction can be reduced by up to 2 bar due to the elimination of two large heat exchangers when integrating OCM with power production. The reduced pressure drop can leads to an increased process efficiency (due to the lower power consumption in compressors) and a lower capital cost (due to the smaller size of the compressors).

Oxidizing Agents

An OCM process requires the presence of an oxidizing agent. The oxidizing agent can be oxygen supplied from air fed to the reactor. In some cases the oxidizing agent can be pure oxygen, supplied by pipeline or recovered from air. In some cases oxygen can be separated from air by cryogenic distillation, as in an Air Separation Unit. In some cases, various membrane separation technologies can be applied to generate an oxygen rich stream. In certain cases, the oxygen stream can be produced by a pressure swing adsorption (PSA) unit or a vacuum pressure swing adsorption (VPSA) unit. In certain cases, while using air as the oxidizing agent, a nitrogen recovery unit (NRU) can be used to reduce the nitrogen content in the OCM reactor system. See, e.g., U.S. patent application Ser. No. 13/739,954 and U.S. patent application Ser. No. 13/936,870, which are entirely incorporated herein by reference.

Ethane Skimming

Systems and methods of the present disclosure can be used to convert both methane and ethane to ethylene, in some cases along with some co-products and by-products. Ethane can be fed directly into a post-bed cracker (PBC), which can be a portion of an OCM reactor downstream of the OCM catalyst, where the heat generated in the OCM reaction can be used to crack the ethane to ethylene. As an alternative, the PBC can be a unit that is separate from the OCM reactor and in some cases in thermal communication with the OCM reactor. The ethane feed stream to the OCM reactor can include (a) ethane recycled to the OCM reactor from an OCM reactor effluent stream, which can be separated in at least one downstream separation module and recycled to the OCM reactor, (b) ethane present in other feed streams (e.g., natural gas), which can be separated in at least one separation module and recycled to the OCM reactor, and (c) any additional (i.e., fresh) ethane feed.

The maximum amount of ethane that can be converted in the PBC can be limited by the flow rate of material exiting the OCM catalyst and/or its temperature. It can be advantageous to utilize a high proportion of the maximum amount of PBC. In some cases, the amount of ethane converted to ethylene is about 50%, about 60%, about 70%, about 80%, about 85%, about 90%, about 95%, or about 99% of the maximum amount of ethane that can be converted to ethylene in the PBC. In some instances, the amount of ethane converted to ethylene is at least about 50%, at least about 60%, at least about 70%, at least about 80%, at least about 85%, at least about 90%, at least about 95%, or at least about 99% of the maximum amount of ethane that can be converted to ethylene in the PBC.

Achieving a high proportion (e.g., greater than or equal to about 60%, 70%, or 80%) of the maximum PBC capacity can be accomplished by adding natural gas to the system, which can have a concentration of ethane that depends on many factors, including the geography and type and age of the natural gas well. The treatment and separation modules of the OCM process described herein can be used to purify the OCM effluent, but can be used to treat (e.g., remove water and $CO_2$) and purify the natural gas that is added to the system along with the OCM effluent, such as, e.g., by separating $C_{2+}$ compounds from methane and separating ethane from ethylene. In some cases, ethane contained in the natural gas feed can be recycled to the OCM reactor (e.g., PBC region) as pure ethane and the system may not be sensitive to the purity and composition of the natural gas, making raw natural gas a suitable input to the system.

The maximal PBC capacity can depend on the ratio between methane and ethane in the input to the OCM reactor, including in some instances the PBC portion. In some cases, the PBC capacity is saturated when the molar ratio of methane to ethane is about 1, about 2, about 3, about 4, about 5, about 6, about 7, about 8, about 9, about 10, about 11, about 12, about 13, about 14, or about 15. In some cases, the PBC capacity is saturated when the molar ratio of methane to ethane is at least about 1, at least about 2, at least about 3, at least about 4, at least about 5, at least about 6, at least about 7, at least about 8, at least about 9, at least about 10, at least about 11, at least about 12, at least about 13, at least about 14, or at least about 15. In some cases, the PBC capacity is saturated when the molar ratio of methane to ethane is at most about 5, at most about 6, at most about 7, at most about 8, at most about 9, at most about 10, at most about 11, at most about 12, at most about 13, at most about 14 or at most about 15. In some cases, the PBC capacity is saturated when the molar ratio of methane to ethane is between about 7 and 10 parts methane to one part ethane.

Natural gas (raw gas or sales gas) can have a concentration of ethane of less than about 30 mol %, 25 mol %, 20 mol %, 15 mol %, 10 mol %, 9 mol %, 8 mol %, 7 mol %, 6 mol %, 5 mol %, 4 mol %, 3 mol %, 2 mol % or 1 mol %. In some cases, natural gas has a methane to ethane ratio greater than about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1 or 40:1. The ethane skimmer implementation of OCM described herein can be used to inject more natural gas feed into the system than what may be required to produce the desired or predetermined amount of ethylene. The excess methane can be drawn from a stream downstream of the methanation unit and sold as sales gas (which may lack an appreciable amount of ethane but can still meet pipeline specifications and/or can be directed to a power plant for power production). The ethane in the additional natural gas feed can be used to saturate the PBC capacity. Any excess ethane can be drawn from the $C_2$ splitter and exported as pure ethane. The ethane skimmer implementation described herein can result in additional product streams from the OCM system (namely sales gas and natural gas liquids). In such a case, the OCM process can be used to achieve both ethylene production and natural gas processing.

Figure 15:
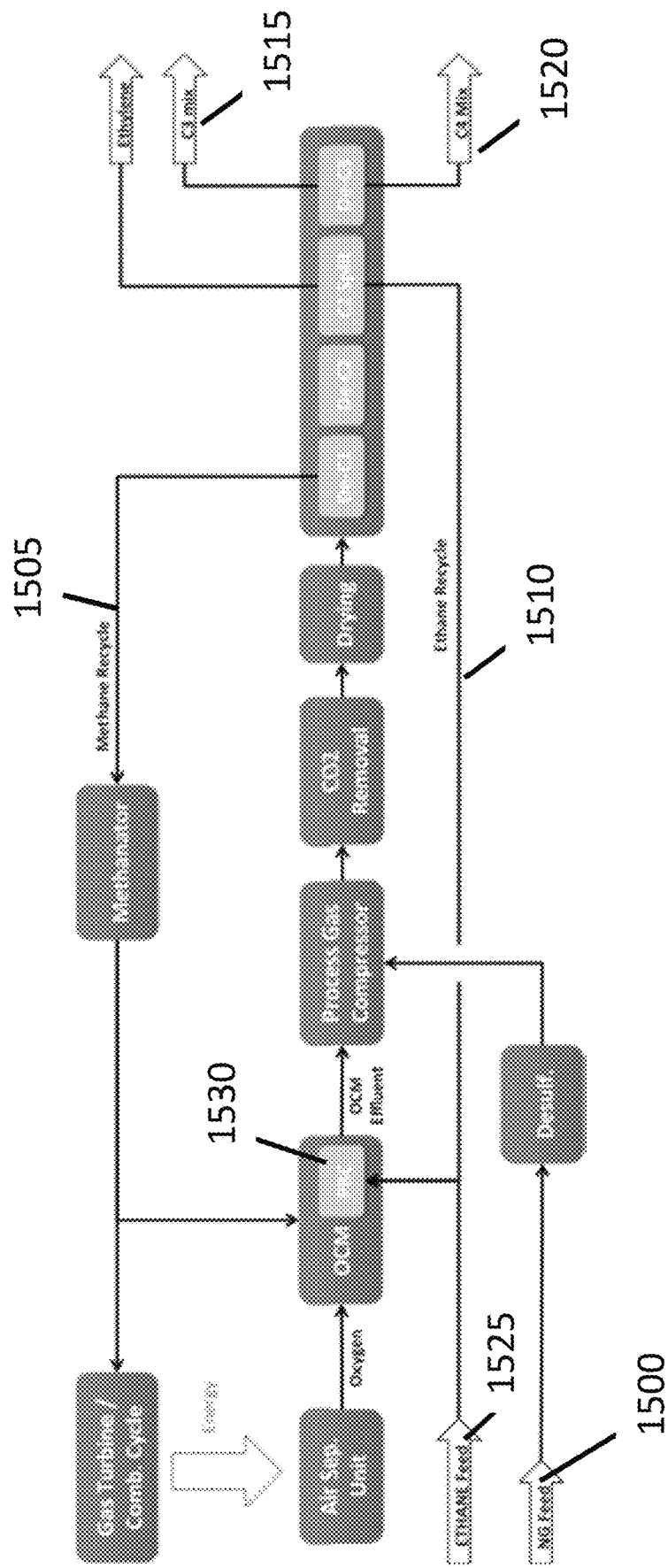
FIG. 15 shows an example of an OCM process with fresh ethane feed and no sales gas export.
Figure 16:
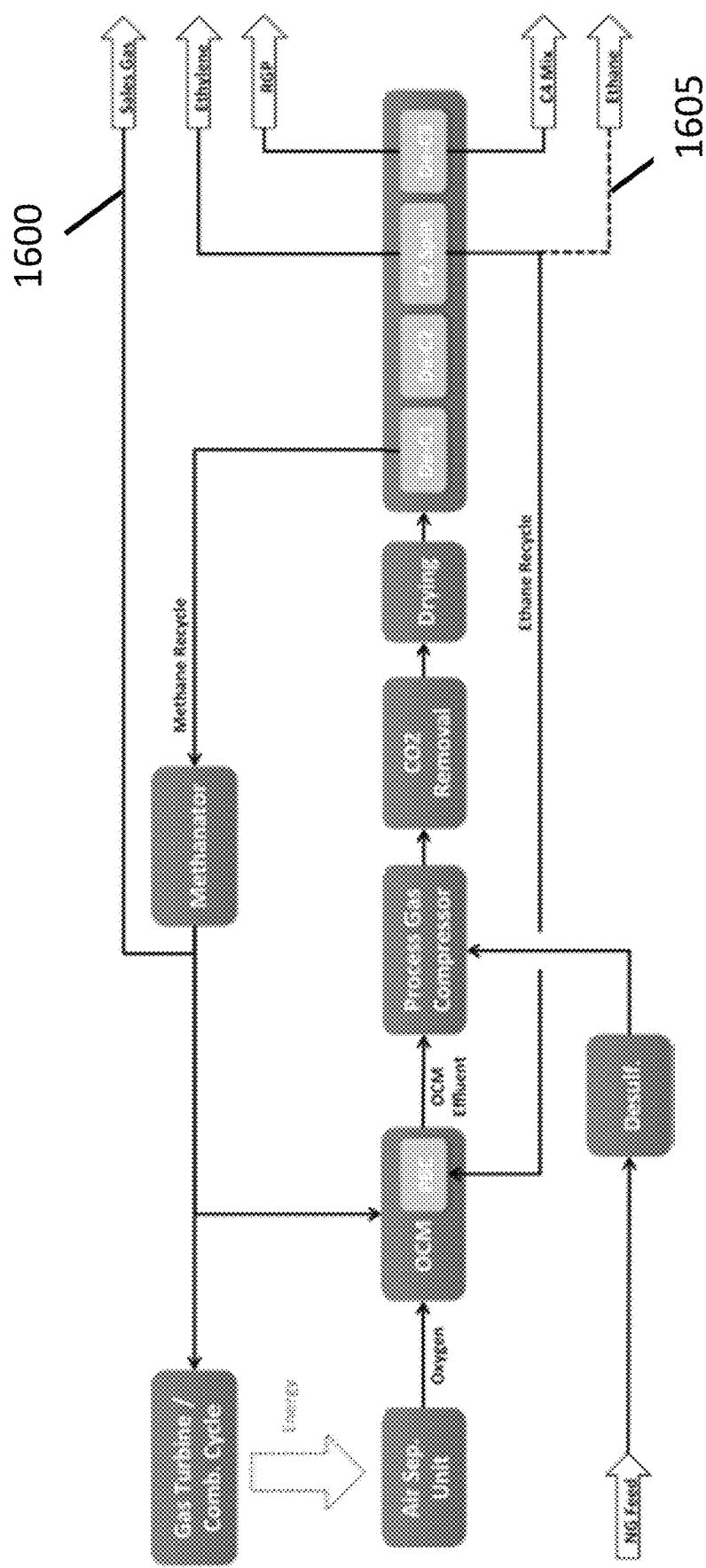
FIG. 16 shows an example of an ethane skimmer implementation of OCM.

The ethane skimmer implementation can be readily understood by reference to FIG. 15 (showing additional ethane feed to saturate PBC) and FIG. 16 (showing the ethane skimmer implementation). In FIG. 15, at least some or most (e.g., >70%, >80%, >85%, >90%, >95%, or >99%) of the methane in the natural gas (NG) feed 1500 ends up in the methane recycle 1505, at least some or most (e.g., >70%, >80%, >85%, >90%, >95%, or >99%) of the ethane in the NG feed ends up in the ethane recycle stream 1510, at least some or most (e.g., >70%, >80%, >85%, >90%, >95%, or >99%) propane in the NG feed ends up in the $C_3$ mixed products stream (e.g., Refinery Grade Propylene (RPG)) 1515, at least some or most (e.g., >70%, >80%, >85%, >90%, >95%, or >99%) of the $C_{4+}$ in the NG feed ends up in the $C_4$ mixed stream 1520, and ethane is added 1525 up to the point where the PBC cracking capacity 1530 is saturated or nearly saturated (e.g., >70%, >80%, >85%, >90%, >95%, or >99%). In contrast, in the ethane skimmer implementation (FIG. 16), some of the methane (any proportion) can end up in a sales gas stream 1600 and if there is excess ethane, it can end up in an ethane product stream 1605. The ethane skimmer implementation does not require a separate (i.e., fresh) ethane stream to saturate or nearly saturate the PBC capacity of the system.

Gas Processing Plants

An OCM process for generating olefins (e.g., ethylene) can be a standalone process, or it can be integrated in other processes, such as non-OCM processes (e.g., NGL process). FIG. 17 shows a system 1700 comprising an existing gas plant 1701 that has been retrofitted with an OCM system 1702 (or with an OCM-ETL system for the production of other olefins (e.g., propylene)). A raw natural gas (NG) feed 1703 is directed into the existing gas plant 1701, which comprises a treatment unit 1704, NGL extraction unit 1705, compression unit 1706 and fractionation unit 1707. The NGL extraction unit 1705 can be a gas processing unit that can use a gas processing recovery technology such as a recycle split vapor (RSV) technology or other technologies. The NGL extraction unit 1705 can be a demethanizer unit, optionally a demethanizer unit incorporated with a recycle split vapor (RSV) retrofit or standalone unit. The treatment unit 1704 can remove water, $H_2S$ and $CO_2$ from the NG feed 1703 and direct natural gas to the NGL extraction or processing unit 1705. The NGL extraction unit 1705 can remove NGLs (e.g., ethane, propane, butane, etc.) from methane and direct methane (with some traces of NGLs and inert gas) to the compression unit 1706 along fluid stream 1708. NGLs or $C_{2+}$ components can be directed to fractionation unit 1707. At least a portion or almost all of the methane (e.g., 10%, 20%, 30%, 40%, 50%, 60%, 70%, 80%, 90%, or 99%) from the fluid stream 1708 is directed along stream 1709 to an OCM reactor 1710 of the OCM system 1702. This integration of an OCM system (in some other cases OCM-ETL system) with an existing natural gas processing or NGLs extraction plant can improve the recovery of olefin/s production by implementing one of the gas processing technologies (e.g., RSV). This integration is suitable for a small scale and world scale olefin production (e.g., ethylene production).

With continued reference to FIG. 17, the compression unit 1706 compresses methane in the fluid stream 1708 and directs compressed methane to a methanation system 1711, which converts any CO, $CO_2$ and $H_2$ in the fluid stream 1708 to methane, which is then directed to natural gas pipeline 1712 for distribution to end users. In some cases, the methanation outlet stream can be treated to remove water (not shown). The dryer system can consist one or more of the following. A bed or multiple desiccant (molecular sieve) beds, separator vessels to condense and separate the water.

The NGLs extraction unit 1705 can extract $C_{2+}$ compounds from the NG feed 1703. NGLs or $C_{2+}$ compounds from the NGL extraction unit 1705 are directed to the fractionation unit 1707, which can be a distillation column. The fractionation unit 1707 splits the $C_{2+}$ compounds into streams comprising various $C_{2+}$ compounds, such as a $C_2$ stream along with $C_3$, $C_4$ and $C_5$ streams. The $C_2$ stream can be directed to a $C_2$ splitter 1713 (e.g., distillation column), which separates ethane from ethylene. Ethane is then directed along stream 1714 to a post-bed cracking (PBC) unit 1715 of the OCM system 1702. In some cases, $C_3$ and/or $C_4$ compounds can be taken from the $C_2$ splitter 1713 and fed into a downstream region of a post-bed cracking (PBC) reactor for olefin production. In some situations, $C_4$ and/or $C_5$ streams can be directed to a $C_4$ or $C_5$ splitter (e.g., a distillation column), which, for example, separate iso-butane ($iC_4$) from normal butane ($nC_4$) and/or separate iso-pentane ($iC_5$) from normal pentane ($nC_5$). In some situations, other alkanes, such as propane and butane, can be directed to the PBC unit 1715.

In the OCM system 1702, methane from the stream 1709 and oxygen along stream 1716 are directed to the OCM reactor 1719. The OCM reactor 1710 generates an OCM product (or effluent) stream comprising $C_{2+}$ compounds in an OCM process, as discussed elsewhere herein. $C_{2+}$ alkanes (e.g., ethane) in the product stream, as well as $C_2$ alkanes in the stream 1714, may be cracked to $C_{2+}$ alkenes (e.g., ethylene) in the PBC unit 1715 downstream of the OCM reactor 1710. The product stream is then directed to a condenser 1717, which removes water from the product stream. The product stream is then directed to a compression unit 1718 and subsequently another compression unit 1719. Methane from the compression unit 1719 is directed to the NG feed 1703 along stream 1720.

The OCM system 1702 can include one or more OCM reactor 1710. For example, the OCM reactor 1710 can be an OCM reactor train comprising multiple OCM reactors. The OCM system 1702 can include one or more PBC reactors 1715.

The compression units 1718 and 1719 can each be a multistage gas compression unit. Each stage of such multistage gas compression unit can be followed by cooling and liquid hydrocarbon and water removal.

Ethylene Plants

In an aspect, the present disclosure provides a method for producing $C_{2+}$ compounds by performing an oxidative coupling of methane (OCM) reaction to produce an OCM effluent comprising methane ($CH_4$), hydrogen ($H_2$), carbon dioxide ($CO_2$), ethylene ($C_2H_4$) and $C_{2+}$ compounds. The OCM effluent can be separated into a first stream comprising $C_{2+}$ compounds and a second stream comprising $CH_4$, $CO_2$, and $H_2$. The second stream can be methanated to produce a first OCM reactor feed comprising additional $CH_4$ formed from the $CO_2$ and the $H_2$ in the second stream. A third stream can be methanated to produce a second OCM reactor feed comprising $CH_4$. The third stream can comprise $CH_4$ and $H_2$ from demethanizer off-gas from an ethylene cracker. The first and second OCM reactor feeds can then be provided to the OCM reaction.

In some embodiments, the second stream and the third stream are methanated in a single methanation reactor. The method can further comprise providing the first stream to the separation section of the ethylene cracker. The ethylene cracker can be an existing ethylene cracker, which may be present prior to retrofitting with an OCM reactor and additional unit operations. The separation section may be evaluated for available capacity to process the additional feed. In some cases, the cracker operation can be modified to operate at a lower severity, hence making some additional capacity available in the existing separation section, especially $C_1$, $C_2$ and $C_3$ area. In some cases, the first stream is provided to a gas compressor or a fractionation unit of the ethylene cracker. In some embodiments, the third stream is the overhead stream of a demethanizer of the ethylene cracker. In some cases, separation is performed in a pressure swing adsorption (PSA) unit. In some embodiments, the OCM effluent is compressed prior to separating in the PSA unit. In some cases, the separation section also includes, but is not limited to, a $CO_2$ removal system, which typically includes an amine system or a caustic tower and/or dryers to remove water from the OCM effluent.

The method can further comprise feeding oxygen ($O_2$) to the OCM reaction. In some cases, the OCM effluent further comprises carbon monoxide (CO) and the CO is converted into $CH_4$ in operation (c). In some instances, the third stream further comprises $CO_2$ or CO. The OCM reaction can further react additional $CH_4$ from external supply of natural gas. In some embodiments, the third stream further comprises $CH_4$.

In another aspect, the present disclosure provides an oxidative coupling of methane (OCM) system for production of $C_{2+}$ compounds. The system can comprise an OCM subsystem that (i) takes as input a feed stream comprising methane ($CH_4$) and a feed stream comprising an oxidizing agent, and (ii) generates a product stream comprising $C_{2+}$ compounds from the $CH_4$ and the oxidizing agent. The system can further comprise a separation subsystem fluidically coupled to the OCM subsystem that separates the product stream into (i) a first stream comprising $C_{2+}$ compounds and (ii) a second stream comprising methane ($CH_4$) hydrogen ($H_2$) and carbon dioxide ($CO_2$) and/or carbon monoxide (CO). The system can further comprise a methanation subsystem fluidically coupled to the second stream and to the OCM subsystem, wherein the methanation subsystem converts $H_2$ and $CO_2$ and/or CO into $CH_4$. The system can further comprise an ethylene cracker subsystem fluidically coupled to the methanation subsystem that provides additional $CH_4$ and $H_2$ to the methanation subsystem.

In some embodiments, the methanation subsystem provides $CH_4$ for the OCM subsystem. The additional $CH_4$ and $H_2$ can be derived from the demethanizer overhead of the ethylene cracker subsystem. The first stream comprising $C_{2+}$ components can be fluidically coupled to the ethylene cracker subsystem. The first stream can be fractionated in the ethylene cracker subsystem. The separation subsystem can include a pressure swing adsorption (PSA) unit.

In some instances, the OCM subsystem is supplied additional $CH_4$ from a natural gas feed stream. In some cases, the oxidizing agent is $O_2$ (e.g., provided by air from an air separation unit or any other type of oxygen concentration unit).

In some embodiments, the OCM subsystem comprises at least one OCM reactor. In some instances, the OCM subsystem comprises at least one post-bed cracking unit within the at least one OCM reactor or downstream of the at least one OCM reactor, which post-bed cracking unit is configured to convert at least a portion of alkanes in the product stream to alkenes. In some cases, the reactor is adiabatic. In some instances, the post-bed cracking unit uses ethane and propane recycle streams from the existing Ethylene cracker subsystem to achieve conversion to ethylene. In some cases, the recycle streams are routed to the cracking furnaces to completely crack the recycle streams.

Figure 18:
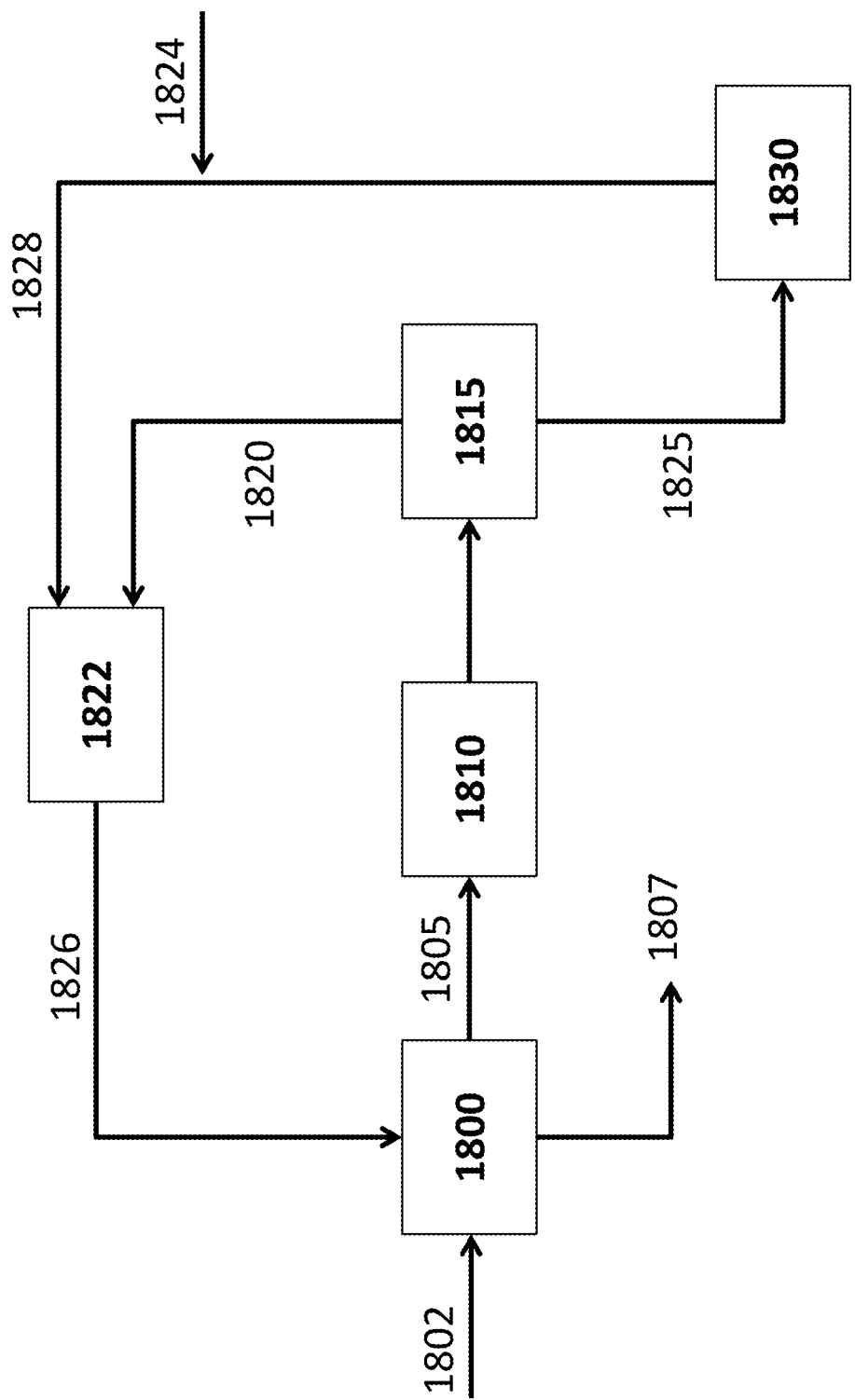
FIG. 18 shows an example of integration of OCM with an ethylene plant.

FIG. 18 shows an example of an OCM process integrated with an existing ethylene cracker. The OCM reactor 1800 takes in methane and oxygen 1802 and produces an OCM effluent 1805 having $CO_2$, $CH_4$ and $C_2H_4$, in some cases amongst other components, such as $H_2$ and CO. The OCM reaction can be exothermic and can produce steam 1807. The OCM effluent 1805 can be compressed in a compressor 1810 and fed into a pressure swing adsorption (PSA) unit 1815.

The PSA unit can produce an overhead stream 1820 that can include $H_2$, $CH_4$, $CO_2$ and CO. The overhead stream can be fed into a methanation subsystem 1822 (e.g., methanation reactor) to provide methane for the OCM reactor 1800. Additional methane can be provided by way of a natural gas stream 1824.

The process of FIG. 18 further includes an existing ethylene cracker 1830 with a demethanizer off gas stream. Demethanizer off gas from the existing ethylene cracker 1830 subsystem can supply additional $CH_4$ and $H_2$ that may be required for methanation. Methane generated in the ethylene cracker 1830 can be returned to the OCM reactor 1800 via stream 1826.

Heavier components can exit the PSA separately 1825 and include ethane, ethylene and $C_{3+}$ compounds, which can be fractionated using existing separations capacity in the ethylene cracker 1830. The heavy components can be processed in the fractionation towers of the ethylene cracker, optionally first being compressed in the existing process gas compressor of the ethylene cracker. In some cases, the heavy components stream can be routed to the $CO_2$ removal unit of the existing ethylene cracker subsystem to meet the $CO_2$ specification.

In processes, systems, and methods of the present disclosure, a Fischer-Tropsch (F-T) reactor can be used to replace a methanation reactor, for example in a methane recycle stream. CO and $H_2$, such as that found in a methane recycle stream, can be converted to a variety of paraffinic linear hydrocarbons, including methane, in an F-T reaction. Higher levels of linear hydrocarbons, such as ethane, can improve OCM process efficiency and economics. For example, effluent from an OCM reactor can be directed through a cooling/compression system and other processes before removal of a recycle stream in a de-methanizer. The recycle stream can comprise $CH_4$, CO, and $H_2$, and can be directed into an F-T reactor. The F-T reactor can produce $CH_4$ and $C_{2+}$ paraffins for recycling into the OCM reactor. A range of catalysts, including any suitable F-T catalyst, can be employed. Reactor designs, including those discussed in the present disclosure, can be employed. F-T reactor operation conditions, including temperature and pressure, can be optimized. This approach can reduce $H_2$ consumption compared to a methanation reactor.

The combination of a new OCM unit and an existing ethylene cracker is expected to have certain synergistic benefits. In some cases, prior to retrofit of an ethylene cracker with OCM, the entire overhead from the existing demethanizer was being used as fuel gas, and can now be available as one of the feeds to the methanation unit. In some cases, the demethanizer overhead off-gas comprises up to 95% methane which can be converted to Ethylene in the OCM reactor, hence increasing the total ethylene capacity. In some cases, the hydrogen content in the existing demethanizer overhead is substantial, and may be enough to meet the hydrogen requirement of the methanation unit.

In some cases, retrofitting an ethylene cracker with OCM reduces (or allows for reduction of) the severity of cracking in the existing cracker, enabling value addition by increasing the production of pyrolysis gasoline components in the cracker effluent, as the OCM reactor produces the ethylene needed to achieve the total system capacity. The cracker can then be operated on high propylene mode to produce more propylene and at the same time meeting the ethylene production rate by the new OCM unit. This retrofit can result in greater flexibility for the ethylene producer with respect to the existing cracker operation.

In some instances, the overall carbon efficiency is increased as the methane and hydrogen from the existing demethanizer off-gases can be utilized to convert the carbon dioxide and carbon monoxide to methane, which is fed to the OCM reactor.

In some instances, ethane and/or propane recycle streams from the existing cracker can be routed to the OCM unit (e.g., instead of the cracking furnaces). These recycle streams are typically routed to the cracking furnaces where they are "cracked to extinction." The advantage over routing the recycle streams to OCM over the cracking furnace is higher selectivity to ethylene in the OCM process.

Purge gas from the OCM-methanation system can (at least partially) meet the fuel gas requirements of the existing cracker complex. In some cases, the fuel requirements are met by the existing demethanizer off-gas.

Additional capacity (e.g., for ethylene, propylene or pyrolysis gasoline components) can be gained by integrating an OCM unit and supplying additional natural gas feed to the OCM reactor unit which will increase ethylene production, and the existing cracker can be operated at a reduced severity and/or increased throughput to produce more olefin and/or pyrolysis gas components. Additional fractionation equipment can be used to recover ethylene, for example, if the existing separations section does not have sufficient capacity, or if the existing cracker is operated at a substantially higher throughput than it was built for.

With regard to the present disclosure allowing for reduced severity of cracking, a cracking furnace can thermally crack the hydrocarbon feed comprising of a full range naphtha, light naphtha, ethane, propane or LPG feed to produce ethylene and propylene, along with pyrolysis gas oil, fuel oil and a methane-rich off-gas. The product mix can depend on the feed composition and the process operating conditions. Important process variables can include steam to hydrocarbon ratio (which can vary from 0.3 for ethane and propane feed, and 0.5 for naphtha feed and as high as 0.7 for light vacuum gas oil feeds), temperature (which can vary from 750-850° C.), and the residence time (which can vary, typically in the range of 0.1 to 0.5 seconds). The cracking reaction is favored by low hydrocarbon partial pressure and hence steam can be added to reduce the hydrocarbon partial pressure. Higher steam to hydrocarbon ratio can improve selectivity at the cost of more energy. Severity is the extent or the depth of cracking, with higher severity achieved by operating the cracking furnace at a higher temperature. High severity operation yields more ethylene, and also results in higher rate of coke formation and hence a reduced time between decoking. As the cracking severity is reduced, the yield of ethylene and lighter components decreases and the yield of propylene and heavier components increases. For liquid feeds, severity is measured as the weight ratio of propylene to ethylene in the cracked gases. For gaseous feeds, severity is measured as percentage conversion (mass) of the key components (e.g., percentage disappearance of ethane or propane). The cracking furnace can be operated to maximize ethylene or propylene, depending on the economics and demand. Another process variable in cracker operation is the coil outlet pressure (COP) which is the pressure at the outlet of furnace coils. Low absolute pressure improves selectivity and the pressure is usually kept at about 30 psia for gaseous feeds and 25 psia for liquid feeds.

For example, the influence of pyrolysis temperature can be isolated by keeping the residence time and steam content constant. As the furnace exit temperature increase, ethylene yield also rises, while yields of propylene and pyrolysis gasoline decrease. At very high temperature, residence time can become the controlling factor. Highest ethylene yields can be achieved by operating at high severity (e.g., about 850° C.), with residence time ranging from 0.2 to 0.4 seconds.

There are numerous ways that the synergies between an OCM unit and an existing ethylene cracker can be realized. Depending on the desired product cut, the OCM unit can significantly increase the flexibility of operation and provide additional capacity gain at a lower incremental cost. Based on the existing plant operation, the desired product spectrum and natural gas availability, integrating an OCM unit with an existing ethylene plant (e.g., naphtha cracker or gas cracker) can offer considerable benefits including:

In some cases, natural gas is more economical than naphtha for converting to ethylene and propylene. Integration with OCM can provide the plant the flexibility to operate with a different feedstock at desired severity. In some cases, the integrating with OCM gives an operational flexibility, to operate at the desired throughput and feed mix depending on the option that makes best economic sense for the operator.

Installing more cracking capacity to an existing cracker can require the entire train of process units to be debottlenecked (e.g., quench, gasoline fractionation, compression, refrigeration, and recovery unit). In contrast, gaining capacity by integrating with OCM can result in minimum impact on the existing process unit debottlenecking. For example, since the OCM reaction is highly selective to ethylene (e.g., greater than 50%), there can be a minimum impact on the rest of the system (e.g., especially the hot section and $C_{3+}$ handling unit).

The OCM reaction is highly exothermic and the high heat of reaction can be put to multiple uses. It may be used to crack more ethane (e.g., from the ethane and propane recycle streams of the existing cracker) to further improve conversion to ethylene. The heat of reaction may also be used to generate steam which can be used to meet process requirements or generate power. The OCM unit can be a net exporter of steam and/or power.

Pyrolysis Process Retrofit with OCM

In an OCM process, methane ($CH_4$) reacts with an oxidizing agent over a catalyst bed to generate $C_{2+}$ compounds. The OCM process produces olefins, such as ethylene, and can add to or replace olefin production from a pyrolysis process (e.g., ethane cracking or naphtha cracking). In some cases, a low price natural gas feedstock (used by the OCM process) makes the retrofit to the cracker (which uses expensive feedstock such as naphtha or ethane) an attractive and economical process.

Figure 19:
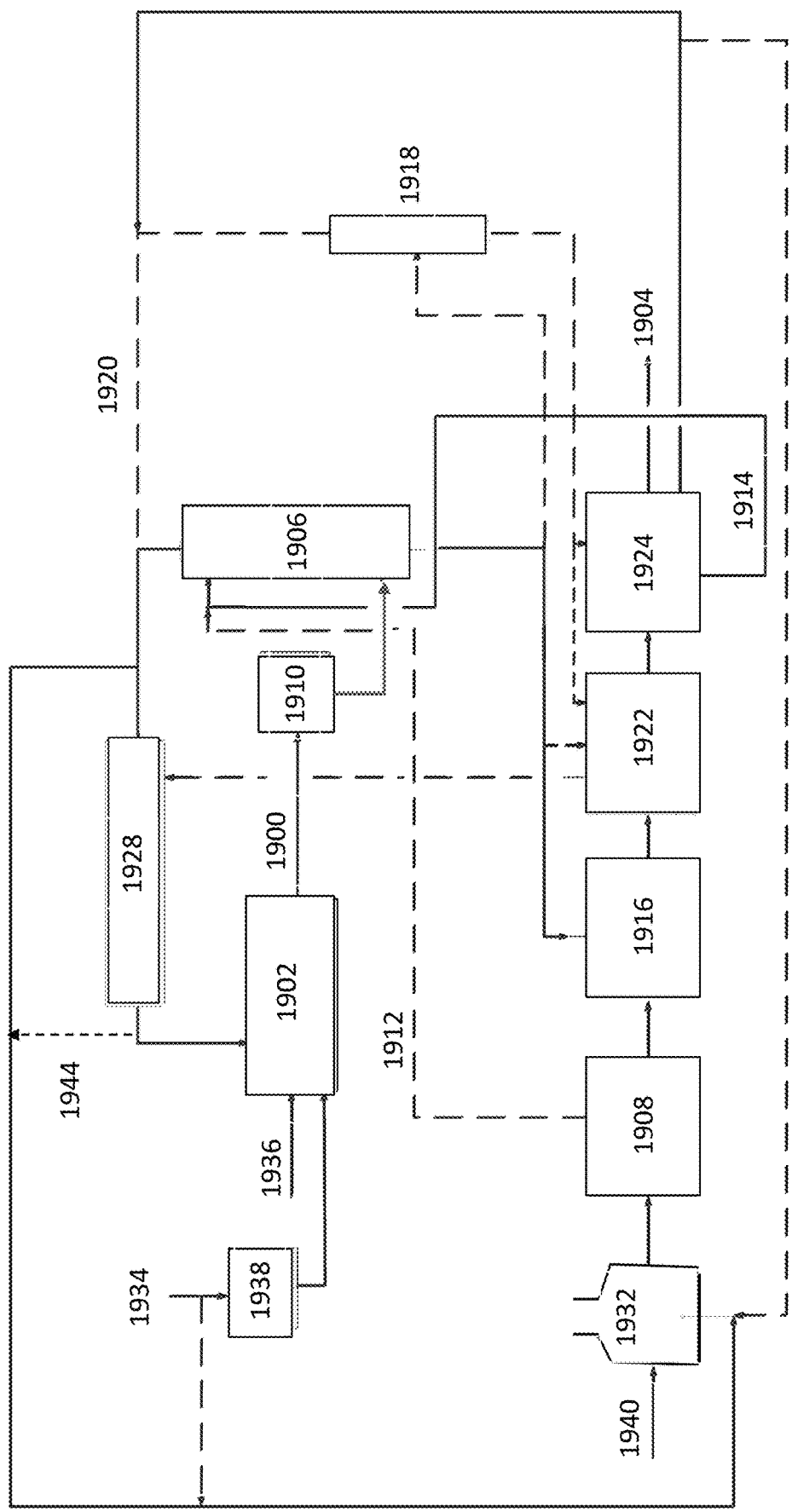
FIG. 19 shows an example of integration of an OCM process with a naphtha cracker.

FIG. 19 illustrates how a cracker 1932 can be retrofitted (integrated) with the OCM process. Various unit operations between the blocks and columns are not shown for the purposes of simplification of the drawing. With reference to FIG. 19, the integrated process uses OCM effluent 1900 from an OCM reactor 1902 (containing $C_1$, and $C_{2+}$ type hydrocarbons) that utilize a separation train downstream of the cracker 1932 to produce olefins 1904, such as ethylene and propylene. Natural gas 1934 is fed into the OCM reactor, along with a source of $O_2$ 1936 (e.g., air or enriched oxygen). The natural gas can be de-sulfurized in a sulfur removal unit 1938.

A lean oil absorber 1906 using light or heavy pyrolysis gas from the cracker, or any oil stream containing hydrocarbons in the $C_5$ to $C_{10}$ range from refining and/or natural gas processing plants, can be used to separate the $C_1$ from the $C_{2+}$ hydrocarbons and uses all or some of the unit operations downstream of the quench tower 1908 of a typical cracker for the cleaning and separations of the hydrocarbons.

The OCM effluent to the process gas compressor (PGC) 1910 compresses the gas to a pressure between 200-800 psia. Water present in the OCM effluent can be removed. A mole sieve drier is a non-limiting example of a process that may remove water from the system, but any conventional water removal system can be used in this system. The effluent is then cooled to between 50° F. and −80° F., in some cases between −20° F. to −60° F., (depending on $C_{2+}$ purity required by the cracker) and sent to lean oil absorber column 1906.

The lean oil absorber 1906 can run with both a light pyrolysis gas (such as $C_{5+}$ pyrolysis gas) obtained from the quench tower of a typical cracker 1912 and also a heavy pyrolysis gas (such as $C_{7+}$ pyrolysis gas) 1914 typically obtained from the heavies fractionator, such as a de-butanizer, de-pentanizer, or gasoline stripper of a cracker, or gasoline from the aromatics extraction plant (either raffinate/light pyrolysis gasoline or the heavy pyrolysis gasoline stream).

The absorber can operate with 40-100 stages, 200-800 psia, and −80° F. to 50° F., providing $C_2$ recovery of 75%-100%. The ratio of the lbs of $C_1$/lb ethylene from the bottoms of the absorber can be between 1.0-3.0 lbs $C_1$/lb ethylene depending on the conditions used in the absorber. The lean oil losses in the process are as low as 0.0004-0.001 wt % of lean oil. The ratio of lean oil to OCM effluent is between 0.5-5.5 on a mass basis.

The rich $C_{2+}$ stream can then be sent to the PGC of the cracker 1916, treated and separated to produce olefins, such as ethylene. For example, the rich oil can be fed to the compressor's third stage discharge drum, where it can flash lights into the fourth stage suction, while the heavies can be sent to the second stage suction for further recovery of lights. Eventually the oil can be recovered in the Quench tower 1980 and sent back to the lean oil absorber. Alternatively, the rich oil can be sent to a new stripping column, with the lights then sent to the appropriate suction drum of the PGC.

If the constraints of the cracker are such that a purer $C_2$ spec is required or if the demethanizer of the cracker is constrained by methane removal capacity, a $C_1/C_2$ fractionator 1918 can be added to recover 60-100% of the methane from the overhead of the fractionator with a much purer $C_{2+}$ stream sent to the either the demethanizer or the deethanizer of the cracker. The $C_{2+}$ can then be separated in the separations train to produce olefins and the $C_1$ sent back to the OCM as recycle $C_1$ 1920. Depending on the $CO_2$ concentration from the $C_1/C_2$ fractionator, a caustic wash can be used or the $C_{2+}$ sent to the gas treating section for $CO_2$ removal.

The $C_1/C_2$ fractionator can run between 200-800 psia, and provide 99.0-99.9% recovery of the methane from the $C_{2+}$ stream. This can be sent to gas treating 1922 before separations 1924 and/or the demethanizer and/or the deethanizer in the cracker depending on the concentration of $CO_2$ and $C_1$ in the $C_{2+}$ stream from the fractionator.

Refrigeration power can also be recovered from the $C_1$ recycle stream to the OCM depending on the conditions at which the absorber and OCM are running. Refrigeration power anywhere between 0.1 kilowatts (KW)/pound ethylene to 1 KW/pound ethylene can be recovered.

The $CO_2$ 1926 from the overhead of either the absorber or the fractionator can be sent to a methanation unit 1928 in which the $CO_2$ and CO react with the $H_2$ in the presence of a catalyst to form $CH_4$ and recycled back to the OCM reactor.

Natural gas produced in the demethanizer of the cracker train can be sent back to the OCM unit to the methanation section. The $H_2$ content in the recycle stream can be methanated in the presence of $CO_2$ and CO in the methanation reactor and sent to the OCM reactor as feed natural gas.

The OCM process also produces a purge stream 1930, with a heating value in the range of 800 BTU/SCF to 1000 BTU/SCF that can be used as fuel gas, make-up or otherwise. Additional natural gas may also be fed to the cracker furnace through streams 1920 before methanation of the $C_1$ recycle, or stream 1944 after methanation (such as, e.g., depending on cracker requirements), to provide fuel gas since the fuel oil is utilized in a more efficient manner of producing olefins. The present example shows how olefins 1904 can be produced from both natural gas 1934 and cracker feed 1940 (e.g., as shown in FIG. 19).

In some cases, the cracker 1932 generates ethane in addition to olefins. The ethane can be recycled to an ethane conversion section of the OCM reactor 1902 for conversion to olefins.

Control Systems

The present disclosure provides computer control systems that can be employed to regulate or otherwise control OCM methods and systems provided herein. A control system of the present disclosure can be programmed to control process parameters to, for example, effect a given product distribution, such as a higher concentration of alkenes as compared to alkanes in a product stream out of an OCM reactor.

Figure 20:
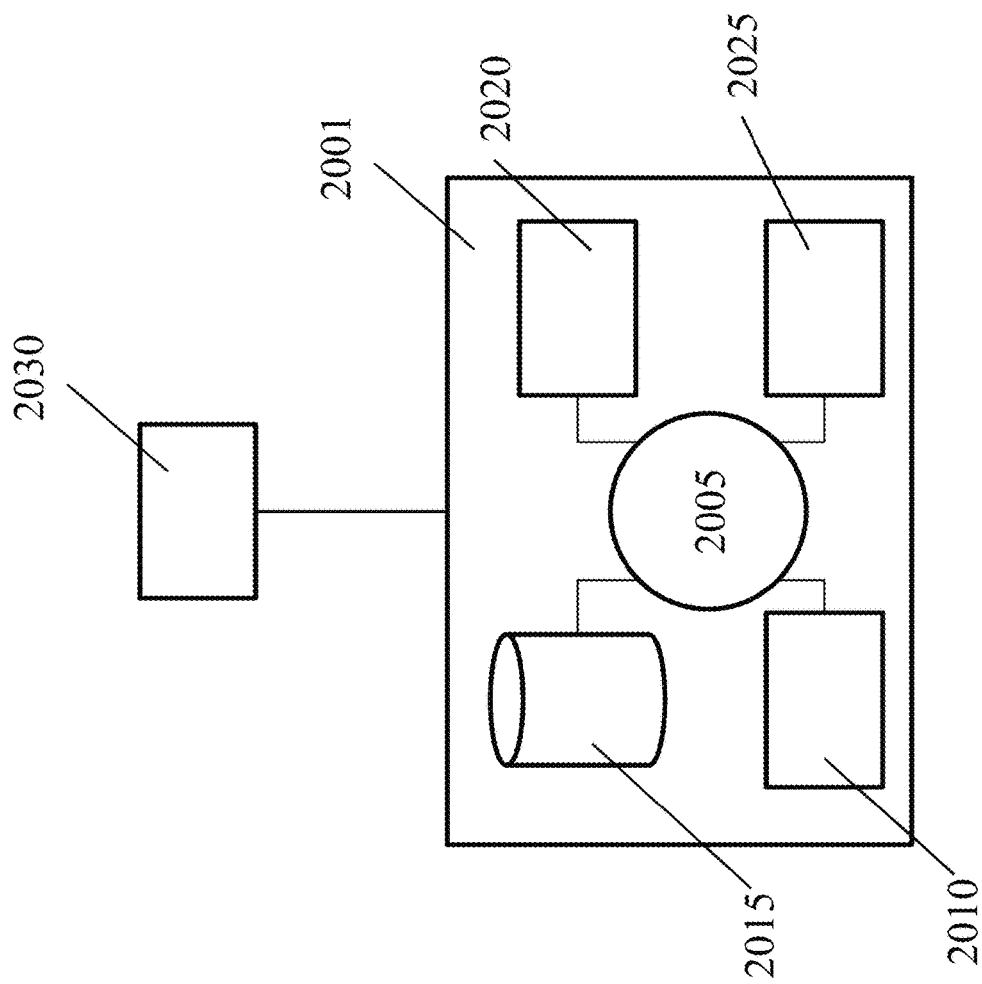
FIG. 20 shows a computer system that is programmed or otherwise configured to regulate OCM reactions.

FIG. 20 shows a computer system 2001 that is programmed or otherwise configured to regulate OCM reactions, such as regulate fluid properties (e.g., temperature, pressure and stream flow rate(s)), mixing, heat exchange and OCM reactions. The computer system 2001 can regulate, for example, fluid stream ("stream") flow rates, stream temperatures, stream pressures, OCM reactor temperature, OCM reactor pressure, the quantity of products that are recycled, and the quantity of a first stream (e.g., methane stream) that is mixed with a second stream (e.g., air stream).

The computer system 2001 includes a central processing unit (CPU, also "processor" and "computer processor" herein) 2005, which can be a single core or multi core processor, or a plurality of processors for parallel processing. The computer system 2001 also includes memory or memory location 2010 (e.g., random-access memory, read-only memory, flash memory), electronic storage unit 2015

(e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data.

The CPU 2005 can execute a sequence of machine-readable instructions, which can be embodied in a program or software. The instructions may be stored in a memory location, such as the memory 2010. Examples of operations performed by the CPU 2005 can include fetch, decode, execute, and writeback.

The storage unit 2015 can store files, such as drivers, libraries and saved programs. The storage unit 2015 can store programs generated by users and recorded sessions, as well as output(s) associated with the programs. The storage unit 2015 can store user data, e.g., user preferences and user programs. The computer system 2001 in some cases can include one or more additional data storage units that are external to the computer system 2001, such as located on a remote server that is in communication with the computer system 2001 through an intranet or the Internet.

The computer system 2001 can be in communication with an OCM system 2030, including an OCM reactor and various process elements. Such process elements can include sensors, flow regulators (e.g., valves), and pumping systems that are configured to direct a fluid.

Methods as described herein can be implemented by way of machine (e.g., computer processor) executable code stored on an electronic storage location of the computer system 2001, such as, for example, on the memory 2010 or electronic storage unit 2015. The machine executable or machine readable code can be provided in the form of software. During use, the code can be executed by the processor 2005. In some cases, the code can be retrieved from the storage unit 2015 and stored on the memory 2010 for ready access by the processor 2005. In some situations, the electronic storage unit 2015 can be precluded, and machine-executable instructions are stored on memory 2010.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

Below are various non-limiting examples of uses and implementations of OCM catalysts and systems of the present disclosure.

Example 1: Implementation of OCM

About 1,000,000 metric tons/year of polymer grade ethylene is produced via the oxidative coupling of methane (OCM). The OCM reactor comprises a 2-stage adiabatic axial fixed bed that utilizes an OCM catalyst (e.g., nanowire catalyst) to convert methane and high purity oxygen to ethylene. The methane feed to the OCM reactor is the recycle stream from a downstream demethanizer over-head supplemented by CO and $CO_2$ conversion to methane in a two-stage methanation reactor. The hot OCM effluent from a second stage of the reactor effluent is mixed with heated recycle ethane from a downstream $C_2$ splitter and cracked to convert ethane primarily into ethylene. Hot reactor effluent is used to heat OCM reactor feed, generate high-pressure steam and heat process condensate. Cold reactor effluent is compressed and mixed with sulfur-free pipeline natural gas and treated to remove $CO_2$ and $H_2O$ prior to cryogenic separations. The treated process gas is fed to a demethanizer column to recover about 99% of ethylene as column bottoms stream. Demethanizer bottoms steam is separated in deethanizer column to separate $C_2$'s from $C_{3+}$ components. Deethanizer column overhead is first treated in selective hydrogenation unit to convert acetylene into ethylene and ethane using $H_2$ from a Pressure Swing Adsorption (PSA) Unit. The resulting stream is separated in a $C_2$ splitter unit to separate ethylene from ethane. Deethanizer bottoms stream is sent to a De-propanizer to obtain Refinery Grade Propylene (RGP) and mixed $C_{4+}$ stream, both which can be sold for credit. Ethane product stream from $C_2$ splitter bottoms is recycled to second stage of the OCM reactor to complete extinction. Polymer grade ethylene product (99.96 wt % ethylene) obtained from the $C_2$ splitter overhead is compressed to 1,000 psig and exported as vapor product. A stream factor of 0.95 is used (equal to an installed capacity of 1,059,000 metric tons/yr).

The OCM process generates superheated high pressure (~1500 psia) steam that is used to run process gas compressors, refrigeration compressors, ethylene heat pump/product compressors, and major pumps. The remainder of the steam and small portion of recycle methane (purge gas) can be exported to combined cycle/gas turbine system to generate power. The OCM process has an energy intensity of −0.89 MMBTU/MT ethylene, while the energy intensity of a comparably sized steam cracking of ethane process is about 31.89 MMBTU/MT.

The reactor consists of a 2-stage adiabatic axial fixed bed with intermediate heat recovery via high-pressure steam generation. The methane stream recycled from the demethanizer overhead becomes the main OCM reactor feed. In both stages high purity oxygen is mixed with the hydrocarbon stream in a proportion of approximately 1:10 on a molar basis to achieve the optimal $O_2$-limited composition for the OCM reaction.

In the OCM reactor, the catalyst enables the partial and highly selective conversion of methane to, primarily, ethylene and ethane, with minor amounts of propylene and propane. Non-selective pathways include high temperature hydrocarbon reactions, such as combustion, reforming and shift. The second stage of the reactor is designed to accommodate an ethane conversion zone immediately downstream of the catalytic bed. Ethane recycled from the deethanizer and, optionally, additional fresh ethane feed are injected into this reactor section where ethane undergoes highly selective adiabatic thermal de-hydrogenation to ethylene.

The OCM reactor effluent flows through a series of heat exchangers to achieve optimal heat recovery and final condensation at ambient temperature, prior to being sent to the Process Gas Compressor (PGC). The natural gas feed stream is mixed with the OCM reactor effluent at the PGC delivery. Gas treating, including $CO_2$ removal and drying, follows the compression step. The product recovery train consists of a demethanizer, deethanizer, acetylene converter and $C_2$ splitter configuration where the refrigeration and heat integration scheme is designed to optimize heat recovery and minimize power consumption. The product streams comprise of polymer grade ethylene and a $C_{3+}$ mixed stream, similar in composition to Refinery Grade Propylene (RGP), which can be optionally further separated and purified. The $C_1$ recycle stream leaving the demethanizer head is sent to a conventional methanation unit where all CO and a portion of the $CO_2$ product react with hydrogen to form methane. The integration of the methanation unit into the overall process design is instrumental to maximize the carbon efficiency of the OCM technology.

The OCM process design is energy neutral. The OCM reaction heat is utilized to provide mechanical power to the rotating units required for compression and pumping. The OCM process gets pure oxygen from an adjacent Air Separation Unit (ASU) which also houses a Gas Turbine Combined Cycle (GTCC). The GTCC unit is fed with the purge gas extracted from the demethanizer overhead and provides all the mechanical power and steam required by the ASU.

The final products are 1,000,000 metric tons per annum of polymer grade ethylene and 88,530 metric tons per annum of $C_{3+}$ hydrocarbons. The $C_{3+}$ hydrocarbons are sent to a depropanizer to obtain refinery grade propylene (65% propylene) as distillate.

Example 2: Design Basis of OCM Implementation

The feedstock streams can include a natural gas stream, which supplies the process with the methane and ethane for conversion into ethylene, an oxygen stream, to be supplied by the dedicated Air Separation Unit (ASU) section, an optional ethane stream, which provides extra ethane (in addition to that contained in the natural gas feed) for conversion into ethylene.

Figure 21:
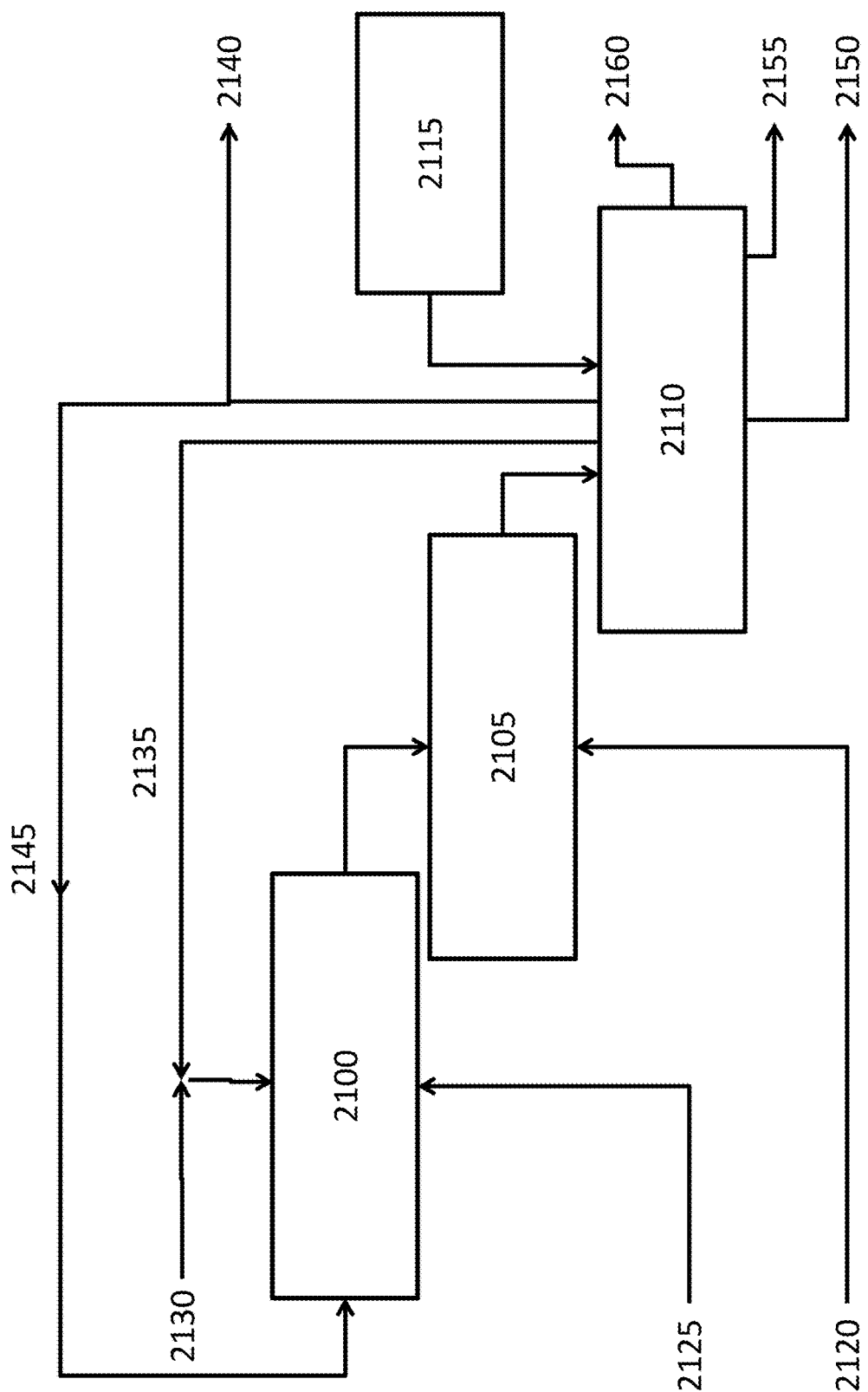
FIG. 21 shows a schematic overview of an implementation of OCM.

As shown in FIG. 21, the ethylene product plant comprises four sections including an OCM reaction section 2100 (comprising methanation, OCM and heat recover), a process gas compression and treating section 2105 (comprising PGC, $CO_2$ removal and drying), a product separation and recovery section 2110 (comprising demethanizer, deethanizer, $C_2$ splitter and de-propanizer) and a refrigeration system 2115 (comprising propylene and ethylene). The process takes in natural gas 2120, which can be desulfurized. The process can take in oxygen 2125 from an air separation unit. Ethane can be added externally 2130 or as part of a $C_2$ recycle 2135. The purge gas 2140 can contain $C_1$ compounds and can be recycled 2145. Products can include ethylene 2150, $C_{4+}$ compounds 2155 and RGP 2160.

Unlike at least some syngas based production processes, the present process is flexible in terms of quality and composition required for the natural gas stream. For example, the process can handle an extremely wide range of natural gas liquids concentration, in particular ethane. None of the typical contaminants present in natural gas, including sulfur, represents a poison for the OCM catalyst. Prior to entering the process, the natural gas feed is treated for sulfur removal in order to prevent contamination of the process outputs and sulfur accumulation in the process. The desulfurization scheme adopted is hydrotreating in a Co/Mo catalyst bed followed by adsorption on a zinc oxide bed. Depending on the actual sulfur content and composition, the adsorption bed may be the only operation. Alternatively other conventional methods of sulfur removal may be used.

The source of the oxygen for the OCM reaction can be air or pure oxygen or any enriched air stream. The presence and concentration of nitrogen may not impact the performances of the OCM reactor system. However, under certain conditions, utilizing pure oxygen as delivered by a conventional Air Separation Unit may minimize the overall process production costs at large scale. Alternatively, enriched air produced via a PSA or air sourced via a compressor may provide the optimal economic solution under other large scale applications.

The OCM reactor has the capability of efficiently processing separate streams of methane and ethane. In the process, the methane stream comes from the demethanizer overhead while the ethane stream, which includes both the unconverted ethane and the ethane contained in the natural gas feed, comes from the deethanizer bottom. Depending on the actual ethane content in natural gas there may be additional ethane processing capacity available in the OCM reactor, which can be saturated with a fresh ethane feed directly mixed with the ethane recycle.

In the particular US Gulf Coast based case presented herein, the natural gas feed is relatively lean (~4.5% mol ethane), thus additional ethane feed is considered to exploit the available reactor capacity and optimize the overall process economics.

A generic process layout for an ethylene plant based on information described in U.S. Patent Publication No. 2014/0012053 and PCT Patent Application No. US/2013/042480, each of which is herein incorporated by reference in its entirety. The process configurations presented herein are illustrative of a commercial system designed to produce high purity (e.g., 99.96 wt % purity) ethylene via oxidative coupling of methane.

As described in Example 1, the plant is sized to produce at least 1,000,000 metric ton/year (2,214 million lb/yr) of polymer grade ethylene at an on-stream factor of 0.95. Hence, the annual installed capacity is equivalent to 1,059,000 metric t/year (2,330 million lb/yr). The plant also produces 61,185 metric ton/year of refinery grade (65%) propylene and 27,345 metric ton/year of $C_{4+}$ compounds. The reactor system is a 2-stage adiabatic axial fixed bed with intermediate heat recovery via high pressure steam generation; OCM nanowire catalyst with bed height=8.3 ft.; 12" refractory lining; $2^{nd}$ stage bottom section used for ethane cracking; and a 2-stage adiabatic methanation unit to convert CO and $CO_2$ recycle into methane. The feedstock is pipeline natural gas, 99.5% oxygen (fed in 1:10 molar basis with hydrocarbon stream), and make-up ethane. The operating conditions include OCM reactor inlet conditions: 540° C. (1004° F.), 131 psia; OCM reactor exit temperature: 830° C. (1525° F.); and methanation reactor inlet conditions: 200° C. (392° F.), 161 psia. The overall conversion is 21.5%, which includes conversion of methane and ethane to all reaction products across the OCM reactor. The carbon efficiency is 71% for the ISBL process (specifies carbon utilization for all ISBL units) and 64% overall (includes energy consumption to run OSBL units (mainly ASU)). The selectivity for each reaction product across the OCM reactor is: 55.9% for $C_2H_4$; 2.2% for $C_3H_6$; 9.7% for CO; 31.3% for $CO_2$; and 0.9% for others.

Example 3: Catalyst Preparation and Catalyst Life

The catalyst is made according to U.S. patent application Ser. Nos. 13/115,082, 13/479,767, 13/689,514 13/757,036 and 13/689,611, and PCT/US2014/028040 filed on Mar. 14, 2014 each of which is entirely incorporated herein by reference. The catalyst is based upon mixed metal oxide catalysts. In some cases, the mixed metal oxide catalysts are comprised of nanowires, mixtures of nanowires and bulk metal oxides, or bulk catalysts. The OCM catalysts can be synthesized via a reaction similar to a standard co-precipitation reaction that takes place in an aqueous solution. The catalysts are then filtered out of the solution, and the resulting solids are calcined.

Figure 22:
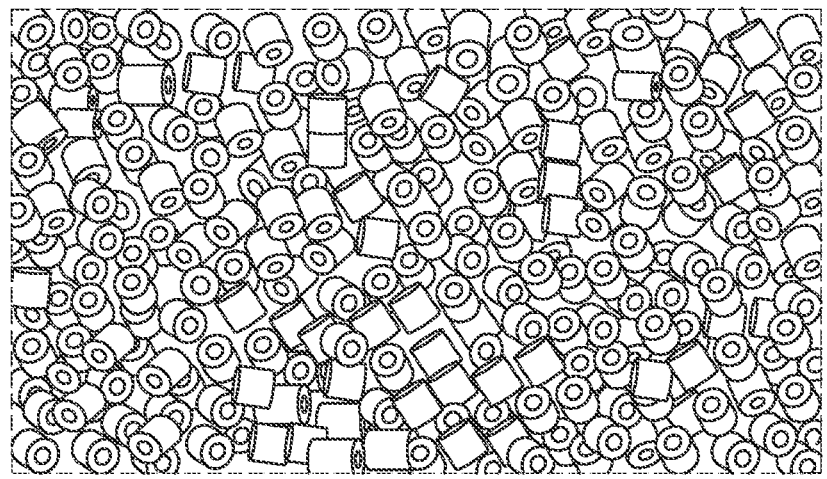
FIG. 22 shows a photograph of a formed OCM catalyst.
Figure 23:
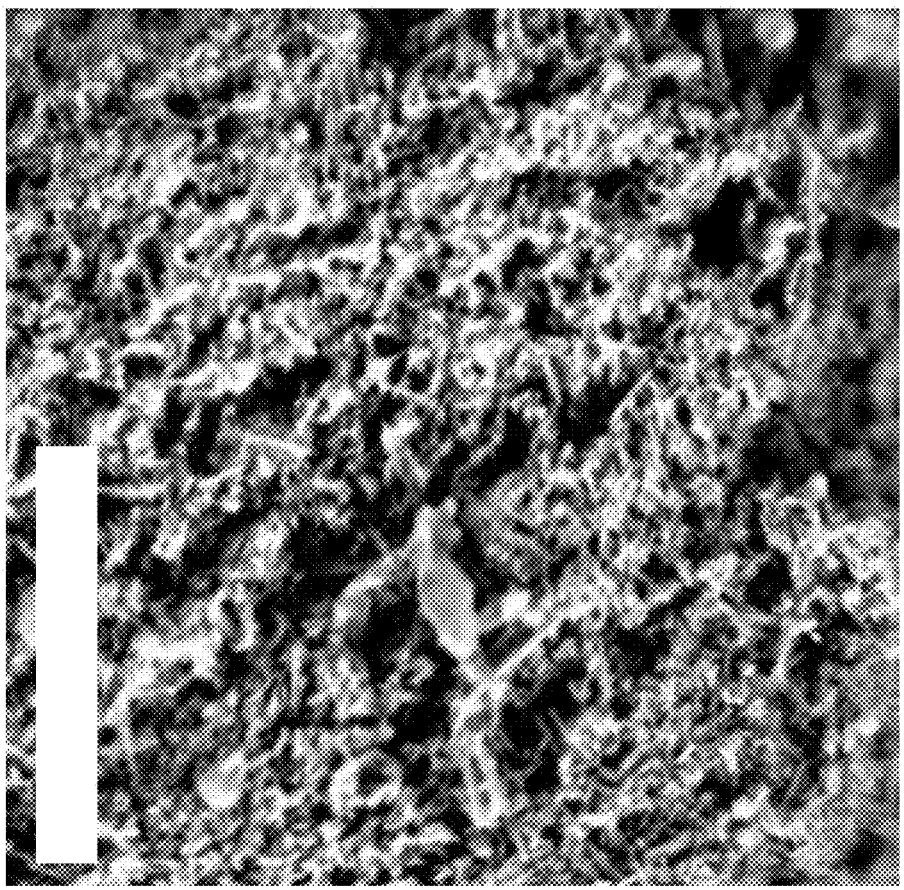
FIG. 23 shows a scanning electron micrograph (SEM) of an OCM catalyst.
Figure 24:
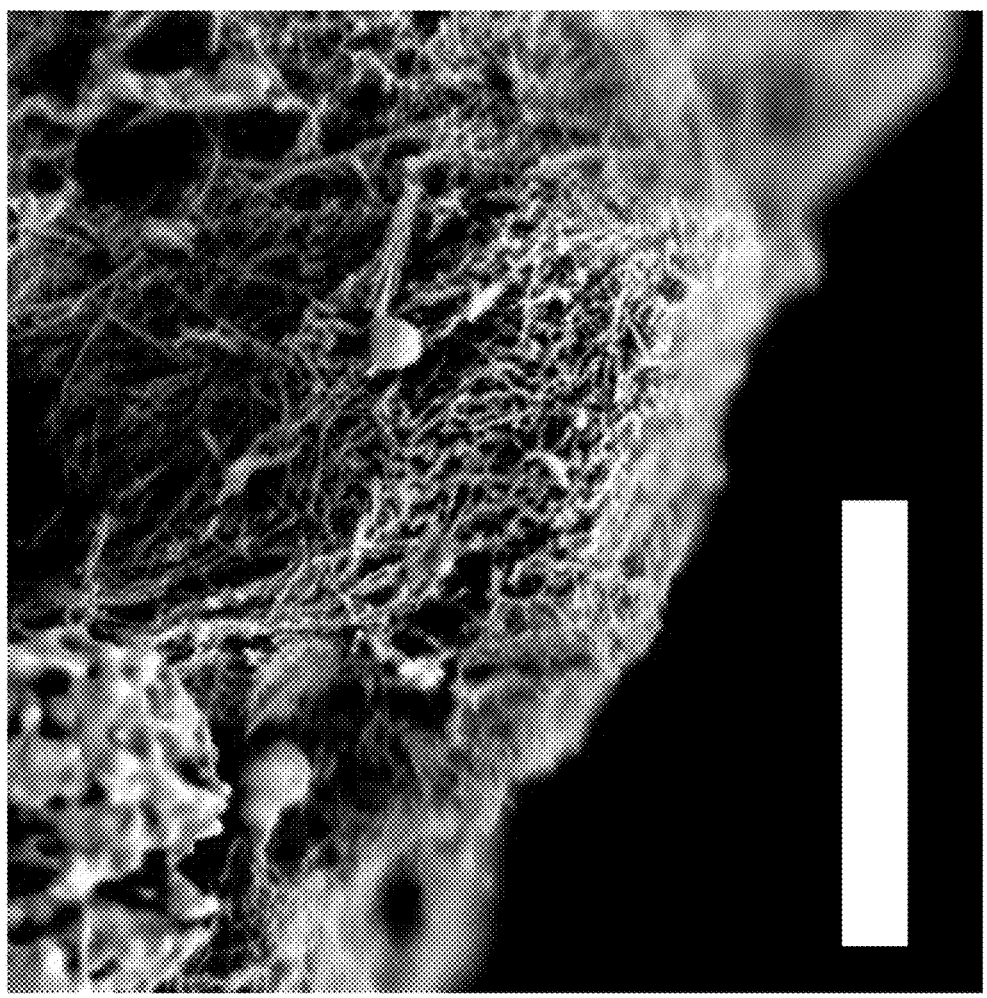
FIG. 24 shows another SEM of an OCM catalyst.

In order to produce a commercial catalyst, the calcined powder is then mixed with catalyst diluents and binders and formed into commercial forms. Catalyst forming tools are then used to form the combined powder, diluents, and binders into solid cylinders (or other shapes, such as spheres, rings, etc.) with the requisite strength and performance requirements. See, e.g., WO2013177461, which is entirely incorporated herein by reference. Such forming can take place via extrusion or tableting or other conventional catalyst forming techniques. FIG. 22 shows an image of the formed cylindrical commercial OCM catalyst. FIG. 23 and FIG. 24 show Scanning Electron Microscope images of a magnified portion of the commercial catalyst. FIG. 23 and FIG. 24 show the entire, formed catalyst with nanowires incorporated along with diluents and binders. The white bar in each of the figures designates a scale bar of 5 micrometers (microns).

Under the operating conditions described within this application, an OCM catalyst is stable, with a minimum lifetime of at least 1 year, 2 years, 3 years, 4 years, 5 years, 6 years, 7 years, 8 years, 9 years, 10 years, or 20 years. An OCM catalyst can be regenerated in-situ or regenerated ex-situ. Alternatively, instead of regeneration, an OCM catalyst can be unloaded and returned to the catalyst manufacturer. There, it can be recycled to reclaim its constituent elemental components, or, alternatively, disposed of.

Example 4: OCM Reactors and Reaction Systems

The OCM reactor contains two reaction zones. The entire reactor is a refractory-lined adiabatic reactor. The first reaction zone contains a fixed OCM catalyst bed, to convert methane into ethylene. This is called the methane conversion zone. In the lower section of the reactor, ethane is injected to homogeneously convert ethane to ethylene utilizing the heat generated during methane conversion. This is called the ethane conversion zone. The introduction of reactants into the OCM reactor system is achieved using, extremely low residence time gas mixers. This allows the reactants to be introduced at elevated temperatures, without participating in non-selective side reactions.

Figure 25:
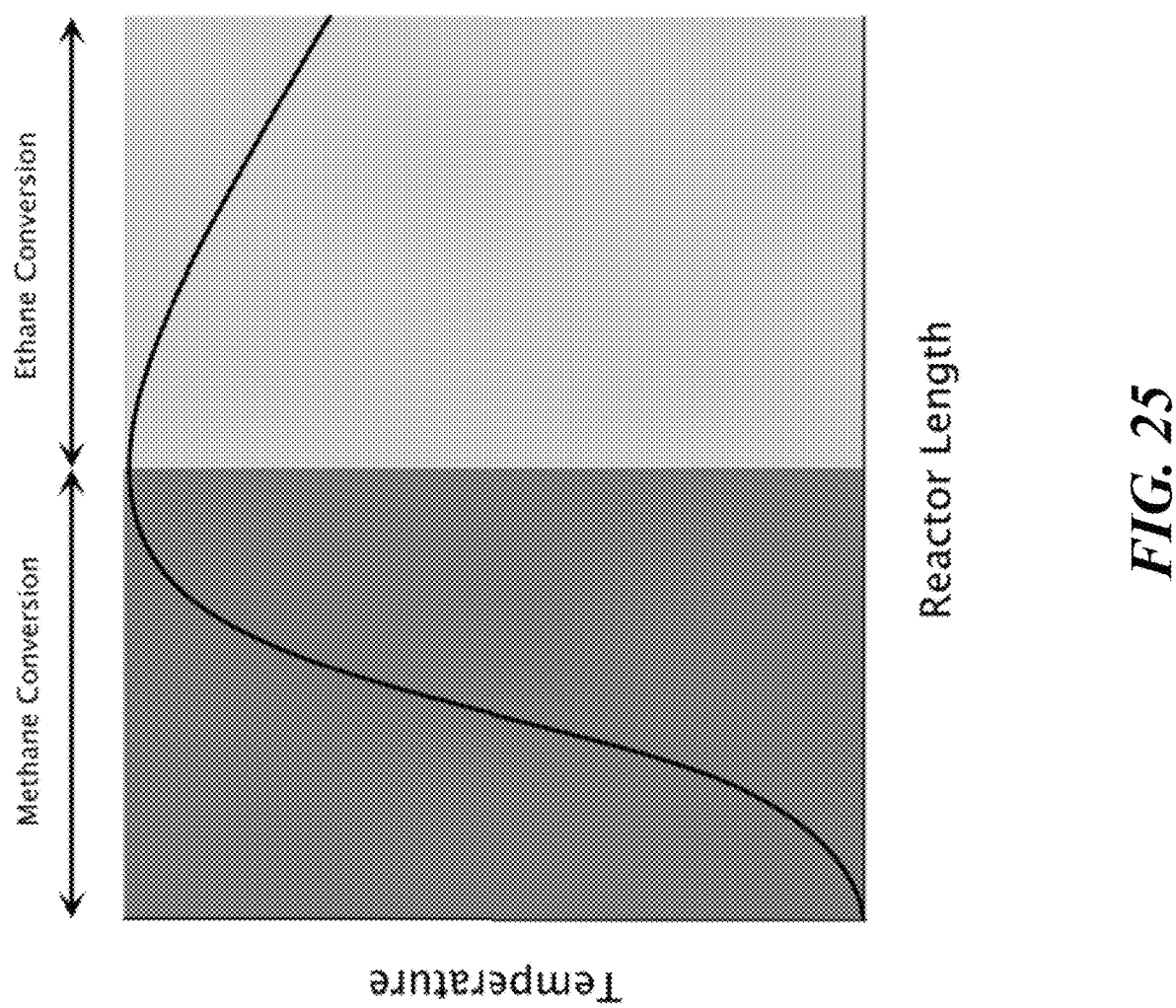
FIG. 25 shows an example of a temperature profile of an OCM reactor.
Figure 26:
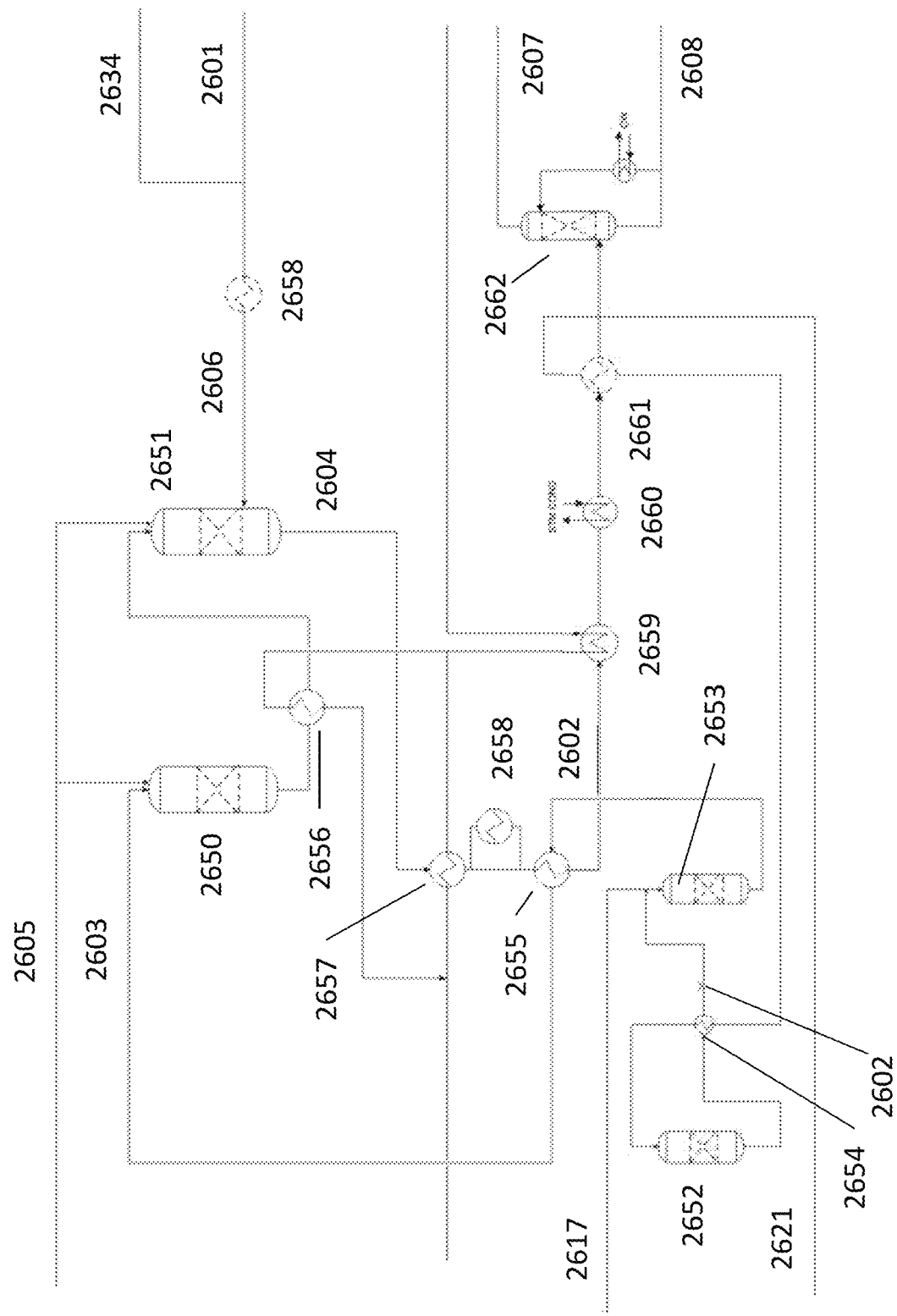
FIG. 26 shows a process flow diagram of a portion of an implementation of OCM.
Figure 27:
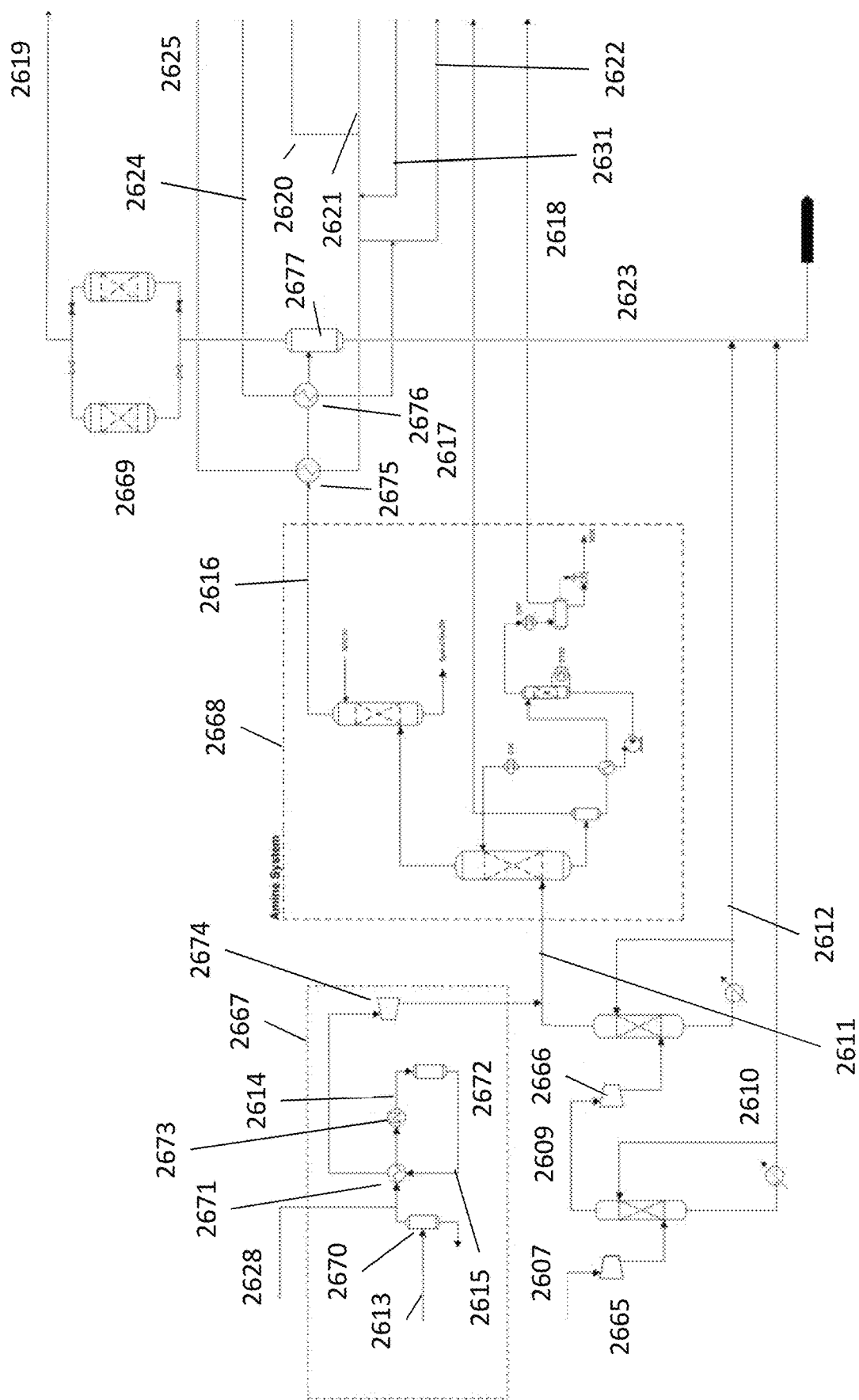
FIG. 27 shows a process flow diagram of a portion of an implementation of OCM.
Figure 28:
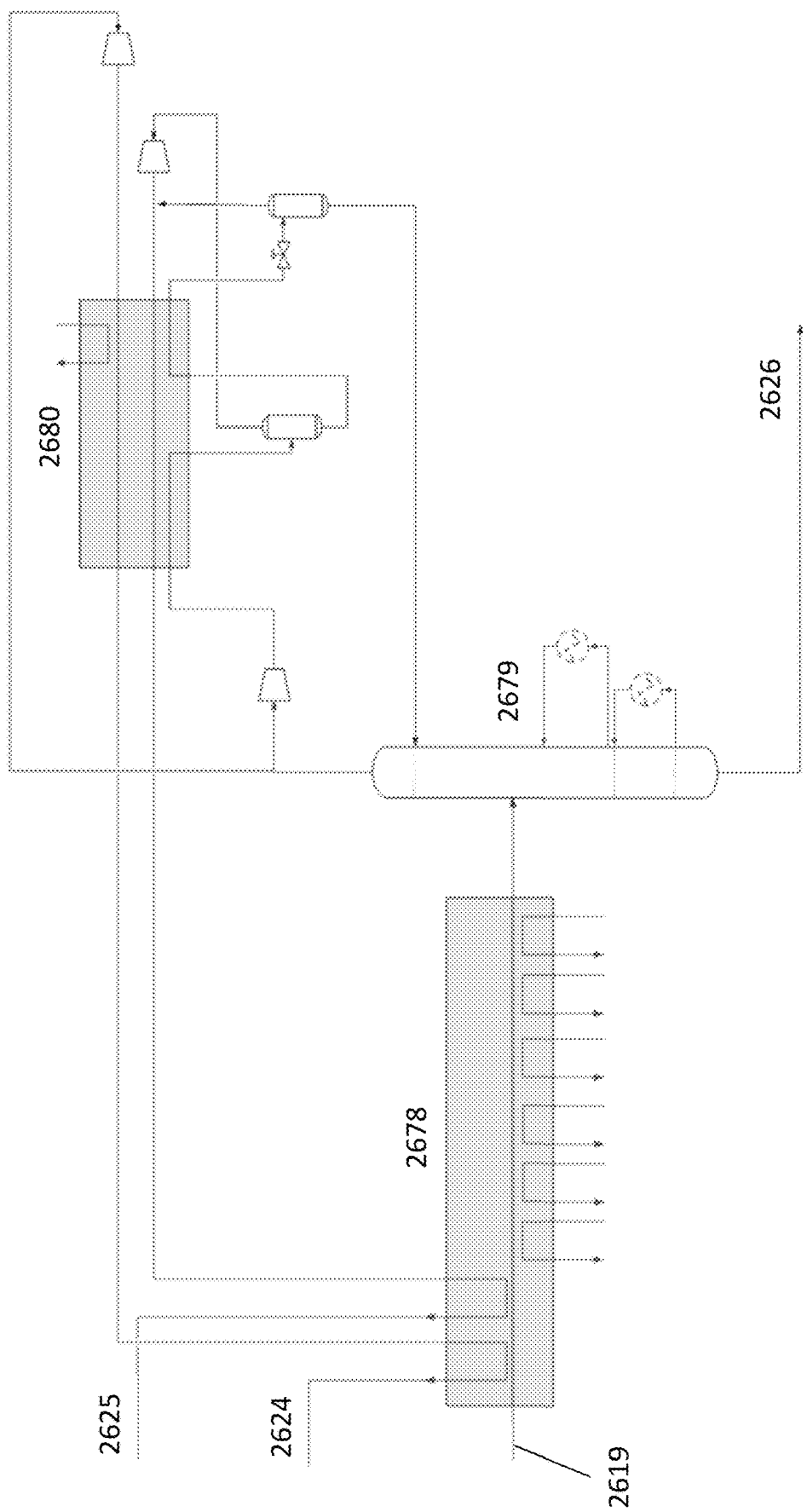
FIG. 28 shows a process flow diagram of a portion of an implementation of OCM.
Figure 29:
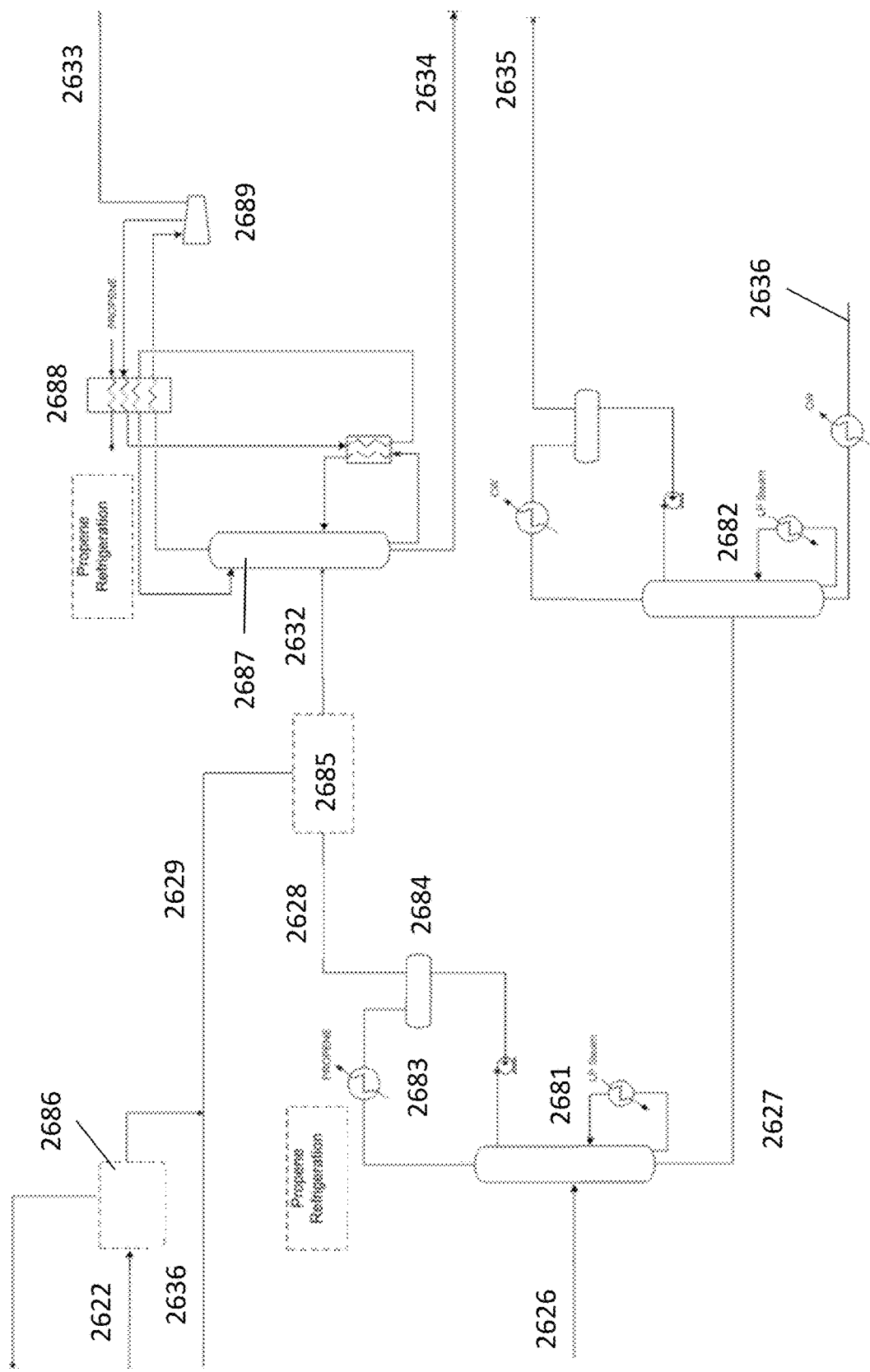
FIG. 29 shows a process flow diagram of a portion of an implementation of OCM.

In the adiabatic OCM reactor system, the temperature is allowed to rise within a reactor stage through the catalytic bed (methane conversion zone), from approximately 460° C., 470° C., 480° C., 490° C., 500° C., 510° C., 520° C., 530° C., 540° C., 550° C., 560° C., 570° C., 580° C., 590° C., or 600° C. at the inlet to about 850° C., 860° C., 870° C., 880° C., 890° C., 900° C., 910° C., 920° C., 930° C. at the outlet of the bed. Ethane at a lower inlet temperature (about 400° C.-500° C.) is injected into the ethane conversion zone to allow for additional non-oxidative dehydrogenation to take place thereby cooling the reactor effluent. A representative temperature profile of the entire reactor is shown in FIG. 25. The reactor has a methane conversion section (e.g., for OCM) and an ethane conversion section (e.g., for conversion of ethane to ethylene).

In some cases, performance of the process in terms of overall carbon efficiency is higher than that of the OCM reactor alone. The higher carbon efficiency derives from the presence of the catalytic methanation step, which converts all CO and a portion of the $CO_2$ product back to methane by utilizing the hydrogen generated in the thermal ethane conversion zone of the OCM reactor.

The methanation unit is a 2-stage adiabatic reaction system, which adopts the same or similar process technology used for Synthetic Natural Gas (SNG) production from syngas. The methanation section is designed to maximize hydrogen consumption and, thus, CO and $CO_2$ recovery to methane. Alternative process configurations may include the use of an isothermal reactor in place of the 2-stage adiabatic system.

The design basis also illustrates the impact of the outside battery limits (OSBL) units (mainly the Air Separation Unit) on the overall carbon and energy balance. In the process the purge gas from the demethanizer overhead fuels the GTCC unit, which is used to provide the mechanical power required by the ASU and make the entire process energy neutral.

With reference to FIGS. 26-31, the OCM Reaction System includes two conversion steps: i) the 2-stage OCM Reactor (R-101A&B 2650 and R-102A&B 2651) that converts the methane and ethane recycle streams into ethylene; and ii) the 2-stage Methanation Reactor (R-103 2652 & R-104 2653) that converts the CO and $H_2$ present in the methane recycle (and some additional $CO_2$) into methane. A series of feed-product economizers, steam generator and super-heater, BFW pre-heater and cooling water exchangers is also included in this process area to provide optimal heat recovery The methane recycle feed stream 2621 coming from the Demethanizer head is first pre-heated to 116° C. (240° F.) in the cross exchanger (E-110) 2661 with the hot effluent from the $2^{nd}$ stage of OCM reactor and then further heated to approximately 200° C. (392° F.) in the Methanator Feed/Product Exchanger (E-101) 2654. This methane stream is then sent to $1^{st}$ stage (R-103) 2652 of the methanation unit where CO is almost completely converted to methane in presence of an excess of hydrogen. Methanation is an exothermic reaction limited by equilibrium and it is carried out over a suitable hydrogenation catalyst in a fixed bed adiabatic reactor. R-103 2652 effluent 2602 is cooled in E-101 2654 against R-103 2652 feed, mixed with additional $CO_2$ coming from $CO_2$ removal unit and then fed to the $2^{nd}$ stage (R-104) 2653 of methanation. In R-104, $H_2$ is the limiting reactant and is almost completely converted in the reaction.

R-104 effluent 2603 is further pre-heated in the Hot Gas-Gas Exchanger (E-102) 2655 to achieve the OCM reactor inlet temperature of 540° C. (1004° F.). It is then fed to the $1^{st}$ stage (R-101) 2650 of the OCM Reactor to undergo OCM conversion to ethylene. In R-101 2650 the pre-heated methane feed stream is mixed with the part of the oxygen supplied by the Air Separation Unit 2605. The mixed feed flows over the OCM catalytic bed and leaves R-101 2650 at a temperature of approximately 830° C. (1525° F.). The reaction heat generated in the $1^{st}$ stage is recovered in the steam generator (E-103) 2656 by generating high pressure (1500 psia) steam. The high pressure stream from E-103 2656 is further superheated to 476° C. (889° F.) in exchanger E-104 2657.

R-101 2650 effluent is then fed to the $2^{nd}$ stage (R-102 A&B) 2651 of the OCM reactor. It is again mixed with oxygen and fed to the OCM catalyst to carry out the OCM reactions. The ethane feed stream 2606 comprising of the ethane recycle 2634 from the $C_2$ splitter bottoms and make-up ethane 2601 is first preheated in the Ethane Gas-Gas Exchanger (E-107 2658) and then injected into the bottom section of R-102 2651 immediately downstream of the OCM catalytic bed to undergo thermal de-hydrogenation to ethylene.

R-102 2651 effluent at approximately 830° C. (1528° F.) is sent to the Steam Generator and Super-Heater Unit, E-106 2657, respectively where the reaction heat generated in the $2^{nd}$ stage is optimally recovered. The product stream leaving E-106 2657 flows through the Ethane and the Hot Gas-Gas Exchangers, prior to entering the Boiler Feed Water (BFW) Pre-Heater (E-108) 2659. The low temperature fraction of the reaction heat is recovered first in the BFW Pre-Heater E-108 2659 and then in the Steam Condensate Pre-Heater E-109 2660. The product gas leaving 2660 flows into the Cold Gas-Gas Exchanger (E-110) 2661 prior to injection into the Quench Tower-I (C-101) 2662.

In the Quench Column (C-101) 2662, the product gas is further cooled to ambient temperature and a significant portion of the water produced in the OCM reactors is condensed and separated as Process Condensates 2608. The C-101 2662 overhead gas stream 2607 is sent to Process Gas Compression and Treating.

Example 5: OCM Process Gas Compression and Treating

The process gas compressor discharge pressure is set to 540 psia to maintain the downstream process gas circuit to a single train with column and vessel sizes limited to a maximum 25 feet diameter. However, the demethanizer can operate as low as 175 psia. This can significantly reduce process gas compression requirements, but requires parallel process gas treatment and demethanizer unit trains and larger propylene and ethylene refrigerant systems. All tradeoffs between capital expense (CAPEX) and operating expense (OPEX) are resolved in a manner that maximizes overall financial return.

Process gas is treated to remove carbon dioxide and water to 0.5 ppmv prior to cryogenic separations using a monoethanol amine-based unit followed by a two-stage caustic wash. Molecular sieve dryers are utilized to remove all moisture from the treated process gas.

With reference to FIGS. 26-31, the Process Gas Compression & Treating section is comprised of four main units: i) The 2-stage (K-201A&B 2665 and K-202 2666) Process Gas Compressors (PGC); ii) a natural gas desulfurization unit 2667; iii) the $CO_2$ removal Unit 2668, including an amine-based absorber and a caustic wash column (G-201); and iv) a drying unit based on molecular sieves absorption (M-201 A-C) 2669.

Process gas from the Quench Column C-101 2662 is compressed in the 2-stage PGC unit (K-201 2665 & 202 2666) to a final pressure of 540 psia. The compressed process gas delivered by K-202 2666 is mixed with the desulfurized natural gas feed stream 2615 and sent to the Amine system unit (G-201) 2668. Pipeline natural gas is first sent through a knockout (KO) drum (V-201) 2670, pre-heated to 260° C. (500° F.) in exchanger (E-201) 2671 against the hot desulfurization reactor (R-201) 2672 effluent 2615 and further heated to 316° C. (600° F.) in a process furnace (F-201) 2673 before entering R-201 2672. The reactor R-201 2672 consists of two beds: the top bed consists of a standard Co/Mo catalyst to convert the sulfur species to $H_2S$ and a bottom ZnO bed to adsorb it. The treated natural gas is sent through a turboexpander (S-201) 2674 to recover some energy.

The rich amine stream leaving the amine absorber bottom is first flashed at an intermediate pressure in the $CO_2$ Flash Drum. The $CO_2$ vapors leaving flash drum 2617 are sent to the methanation unit, as described in the previous section. The liquid bottoms leaving flash drum are heated against the lean amine from the Amine Regeneration Columns in the Lean-Rich Solution Exchanger. Medium pressure steam is used to provide the necessary heat for the Regeneration Columns Reboilers. The Regeneration column overhead vapor is cooled and then washed with process water to remove any residual amines prior to $CO_2$ venting 2618 to atmosphere. The overhead process gas from the $CO_2$ Absorber is further treated in the Caustic Wash Column, which consists of two stages (rich and lean caustic wash), followed by water-wash stage. The treated process gas from Caustic Wash Column 2616 is cooled in exchangers, E-204 2675 and E-205 2676, against the methane recycle 2623 and H$_2$ recycle 2624 streams from the demethanizer, respectively, and then separated in the Knock-Out Drum V-202 2677. The methane recycle streams after exchanging heat through E-204 2675, receives part of the H$_2$ recycle and the PSA purge stream 2631, before being split into the purge gas stream 2620 and C$_1$ recycle stream 2621. The purge gas can be sold for credit or alternatively sent to the Gas Turbine Combined Cycle (GTCC) unit housed in an adjacent Air Separation Unit (ASU) to generate mechanical power. Part of the H$_2$ recycle stream is sent to the PSA unit 2622 to recover hydrogen for NG desulfurization in R-201 2672 and Acetylene dehydrogenation in R-301.

The process gas leaving V-202 2677 is then fed to the Molecular Sieve Gas Dryers (M-201A-C) 2669 where all moisture present in the vapors is removed. The dried process gas is then routed to product separation and recovery.

Example 6: OCM Process Gas Separations

The cryogenic separation section of this example utilizes demethanizer and deethanizer technology, but refrigeration is supplemented by expansion-cooling of the olefin-rich process gas as explained in U.S. patent application Ser. No. 13/739,954, which is herein incorporated by reference in its entirety. By utilizing these methods, the amount of refrigeration provided by propylene and ethylene can be reduced, which provides substantial energy savings.

The treated process gas is separated through a demethanizer, deethanizer, ethylene fractionator (C$_2$ splitter) and de-propanizer. Treated process gas is cooled using the demethanizer unit overhead product streams and side reboiler and the remainder of the cooling duty is provided by propylene and ethylene refrigeration. The demethanizer recovers 99% of the contained ethylene. The bottoms of the demethanizer are sent to the deethanizer. The overall heat integration scheme for the demethanizer cooling is an aspect of the present disclosure. It includes the adoption of a split vapor process scheme, where a portion of the demethanizer overhead vapor is compressed and then expanded to provide the necessary reflux to the demethanizer. The remaining vapor streams are sent to a turbo-expander to recover refrigeration value and then recycled to the OCM reactor.

The balance between the demethanizer operating pressure, the amount of cooling produced by the internal split vapor scheme and the amount of refrigeration provided by external units constitutes an area of optimization for the trade-off between CAPEX and OPEX. The deethanizer unit is a separation column designed for an ethane recovery of 99 mol %. Deethanizer unit bottoms stream is further fractionated in a de-propanizer to recover a Refinery Grade Propylene (RGP) product stream and a C$_4$ mix product stream.

The deethanizer overhead stream is treated for acetylene and fed to the C$_2$ splitter, a heat pumped fractionator system. The overhead vapor is compressed and used to provide hot vapor for the reboiler. Liquid from the reboiler is then used to provide refrigerant for the condenser. The C$_2$ splitter can have a few trays that serve as a pasteurizing section to remove most of the hydrogen or other inerts that enter the C$_2$ splitter unit from the acetylene converter. The C$_2$ splitter can recover 99% of the contained ethylene with a purity of 99.95 mol %. The bottoms product is ethane and is recycled back to ethane conversion section of the OCM reactor.

With reference to FIGS. 26-31, the process gas stream 2619 leaving the Gas Dryers M-201A-C 2669 is routed to the first cold box E-301 2678 and cooled against a series of cold streams coming from the Demethanizer system and from the external refrigeration units. The cooled gas stream leaving E-301 2678 is fed to the Demethanizer Column C-301 2679, where the C$_{2+}$ compounds are separated from the lighter components of the process gas (primarily CH$_4$, CO and H$_2$). The Demethanizer Column overhead products 2624 and 2625 are re-heated against the Demethanizer Column feed and recycled to the OCM Reaction System.

The overhead reflux necessary for the proper operation of the Demethanizer Column C-301 2679 is generated via a proprietary refrigeration process scheme, known as the Recycle Split Vapor Unit (G-301) 2680 that minimizes the need for external refrigeration input. The C-301 2679 bottom stream 2626 consists of ethane, ethylene, acetylene and a small fraction (~5.4%) of heavier (C$_{3+}$) components. This liquid stream is sent to the Deethanizer Column (C-302) 2681. The Deethanizer Column (C-302) 2681 separates the C$_{3+}$ components in the C-302 2681 feed from the C$_2$ components with minimum loss of ethylene in the C$_{3+}$ stream. C-302 2681 bottoms stream 2627 represents the mixed C$_{3+}$ product stream which is sent to a Depropanizer (C-304) 2682. Refinery grade propylene (RGP) (~65% propene) is obtained as C-304 2682 distillate stream 2635 and is sent to the appropriate distribution system to obtain by-product credit. Similarly, C-304 2682 bottoms stream 2636 contains a mixed C$_{4+}$ stream that can be sold.

The C-302 2681 overhead stream is cooled in a partial condenser (E-304) 2683 using propene refrigeration. Liquid condensate is sent as reflux to C-302 2681. C-302 2681 overhead vapor product 2628 is then heated in E-302 2684 and routed to a two-stage acetylene hydrogenation reactor R-301 2685 where all acetylene is hydrogenated to ethylene and ethane.

A pressure swing adsorption (PSA) unit (G-302) 2686 is installed on a slip stream of the demethanizer overhead vapors to produce the high-purity hydrogen stream required by the acetylene hydrogenation reactor (R-301) 2685. The acetylene reactor operates at low temperatures (100° F. Start of run and 150° F. End of run) using a selective palladium catalyst to convert acetylene to ethylene and ethane. R-301 2685 effluent 2632 is cooled and sent to the Ethylene Splitter (C-303) 2687. C-303 2687 produces a 99.96 wt % pure ethylene overhead product 2633 and a 99% pure ethane stream 2634 as bottoms. A cold box (E-306) 2688 serves as the C-303 2687 condenser and reboiler. A heat pump compressor K-302 2689 provides hot ethylene vapor to the C-303 reboiler after looping once through the condenser. The condensed ethylene liquid from the reboiler is used in the C-303 condenser.

The high-pressure ethylene product 2633 from K-302 2689 is sent to the relevant distribution system. The C-303 bottoms 2634 are recycled to OCM reaction and injected into the 2$^{nd}$ stage R-102 2651 of the OCM Reactor.

Example 7: Refrigeration and Steam Generation

Figure 30:
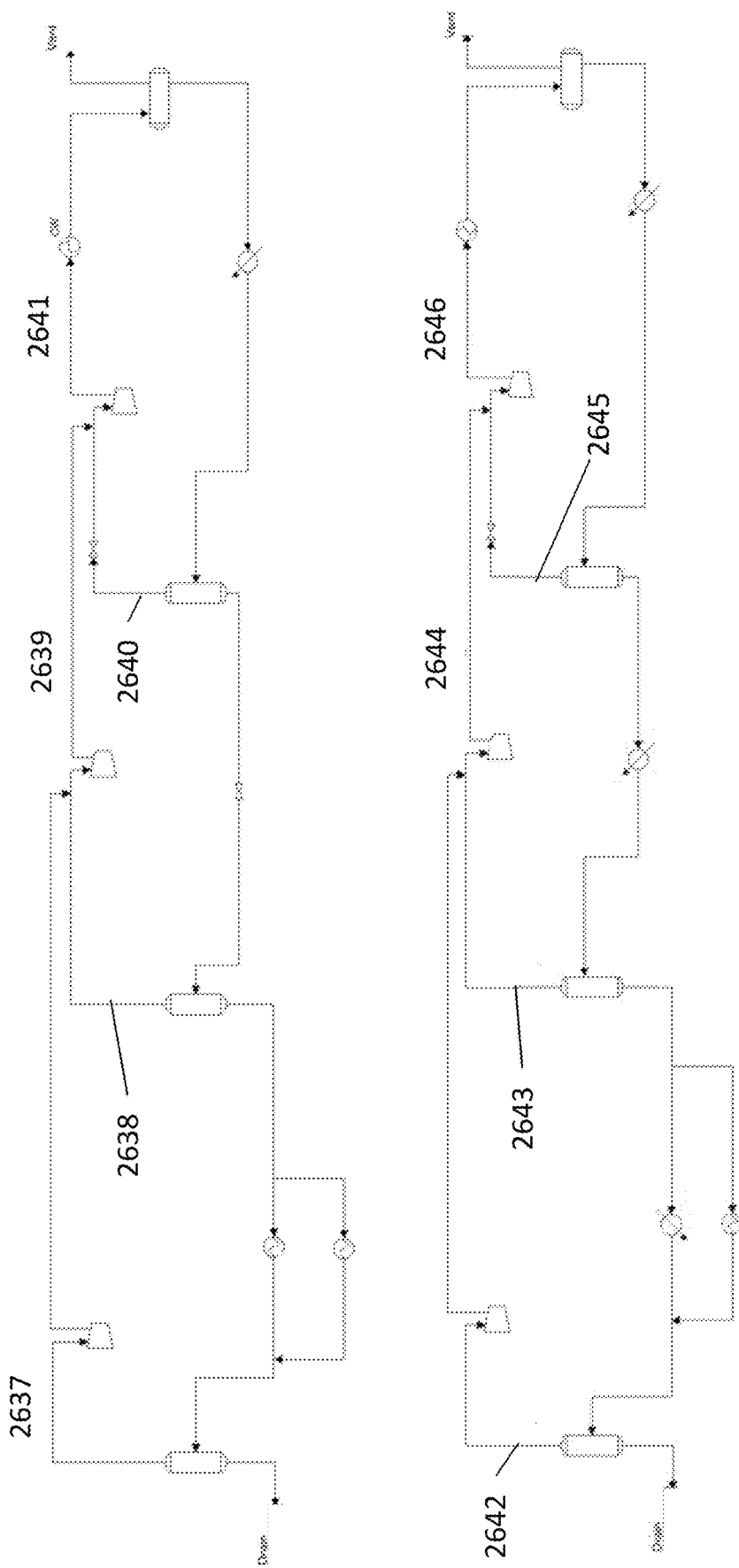
FIG. 30 shows a process flow diagram of a portion of an implementation of OCM.
Figure 31:
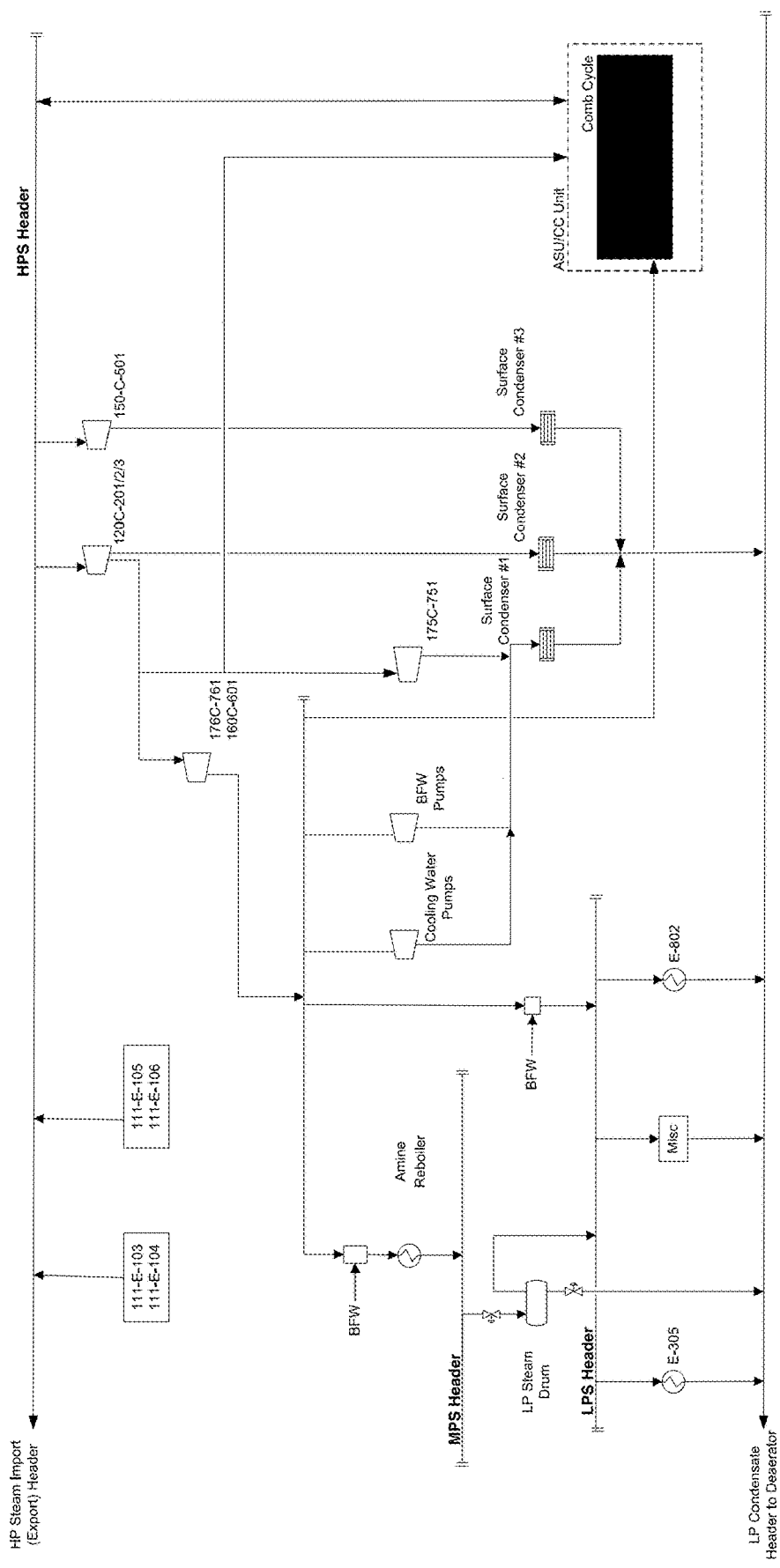
FIG. 31 shows a process flow diagram of a portion of an implementation of OCM.

The system consists of propylene and ethylene refrigeration systems. Propylene refrigeration system is a three-stage refrigeration system, with three different coolant levels, as illustrated in FIG. 30. Additional utilities are shown in FIG. 31.

Evaporating ethylene from the propylene refrigeration cycle is used to condense the ethylene in the ethylene refrigeration cycle and provide refrigerant to the deethanizer overhead condenser (E-304 2683) and the demethanizer cold box (E-301 2678).

Ethylene refrigeration system is also a three-stage refrigeration system as illustrated in FIG. 30. This system provides refrigeration to the demethanizer cold box (E-301 2678) and to the Recycle Split Vapor Unit (RSV 2680).

Superheated, high pressure (HP) steam (1500 psia, 889° F.) generated by the OCM process is used to drive the process gas compressor, the demethanizer overhead compressor, the refrigeration compressors, the ethylene fractionator heat pump and product compressors, half of cooling water and boiler feed water pumps (in offsites), and is fed to medium pressure (MP, 165 psia) and low pressure (LP, 50 psia) reboilers after proper flashing and de-superheating. Any remaining steam can be exported to the Gas Turbine Combined Cycle (GTCC) unit housed in an adjacent Air Separation Unit (ASU) that provides 99.5% $O_2$ for the OCM reaction. A purge gas stream is also sent to the GTCC unit to generate the mechanical power required by the ASU unit. In this review, excess steam and purge gas account for utility and by-product credit, respectively Example 8: Stream Compositions Table 1 shows the total flow-rate and flow rates of selected molecular entities (e.g., Hydrogen and Argon) for select streams of the example process. Stream numbers correspond to those of Examples 4-7 and FIGS. 26-31.

TABLE 1

Stream flow rates

| Stream # | Total (1000 lb/hr) | Methane | Ethylene | Ethane | Acetylene | Propene | Propane | $C_{4+}$ Compounds |
|---|---|---|---|---|---|---|---|---|
| 2001 | 65.8 | 0.0 | 0.0 | 62.0 | 0.0 | 0.0 | 3.8 | 0.0 |
| 2002 | 2694.7 | 2320.7 | 0.0 | 2.5 | 0.0 | 0.0 | 0.0 | 0.0 |
| 2003 | 2792.4 | 2348.8 | 0.0 | 2.5 | 0.0 | 0.0 | 0.0 | 0.0 |
| 2004 | 8304.9 | 1909.0 | 268.9 | 102.7 | 3.7 | 10.4 | 0.4 | 4.5 |
| 2005 | 843.6 | 0.0 | 0.0 | 0.0 | 0.0 | 0.0 | 0.0 | 0.0 |
| 2006 | 209.0 | 0.0 | 2.7 | 202.6 | 0.0 | 0.0 | 3.8 | 0.0 |
| 2007 | 3264.1 | 1908.7 | 268.9 | 102.8 | 3.7 | 10.4 | 0.4 | 4.5 |
| 2008 | 581.1 | 0.0 | 0.0 | 0.0 | 0.0 | 0.0 | 0.0 | 0.0 |
| 2009 | 3238.1 | 1908.7 | 269.0 | 102.8 | 3.7 | 10.4 | 0.4 | 4.5 |
| 2010 | 27.5 | 0.0 | 0.0 | 0.0 | 0.0 | 0.0 | 0.0 | 0.0 |
| 2011 | 3691.5 | 2303.4 | 269.0 | 138.7 | 3.7 | 10.4 | 5.5 | 7.3 |
| 2012 | 5.1 | 0.0 | 0.0 | 0.0 | 0.0 | 0.0 | 0.0 | 0.0 |
| 2013 | 457.9 | 394.7 | 0.0 | 35.9 | 0.0 | 0.0 | 5.1 | 2.8 |
| 2014 | 458.5 | 394.7 | 0.0 | 35.9 | 0.0 | 0.0 | 5.1 | 2.8 |
| 2015 | 460.1 | 395.0 | 0.0 | 35.9 | 0.0 | 0.0 | 5.1 | 2.8 |
| 2016 | 3181.9 | 2303.4 | 269.0 | 138.7 | 3.7 | 10.4 | 5.5 | 7.3 |
| 2017 | 97.7 | 0.0 | 0.0 | 0.0 | 0.0 | 0.0 | 0.0 | 0.0 |
| 2018 | 424.4 | 0.0 | 0.0 | 0.0 | 0.0 | 0.0 | 0.0 | 0.0 |
| 2019 | 3174.1 | 2303.4 | 269.0 | 138.7 | 3.7 | 10.4 | 5.5 | 7.3 |
| 2020 | 45.3 | 0.0 | 0.0 | 0.0 | 0.0 | 0.0 | 0.0 | 0.0 |
| 2021 | 2694.7 | 2268.5 | 2.4 | 0.0 | 0.0 | 0.0 | 0.0 | 0.0 |
| 2022 | 34.5 | 26.1 | 0.0 | 0.0 | 0.0 | 0.0 | 0.0 | 0.0 |
| 2023 | 6.1 | 0.0 | 0.0 | 0.0 | 0.0 | 0.0 | 0.0 | 0.0 |
| 2024 | 2094.2 | 1814.5 | 2.2 | 0.0 | 0.0 | 0.0 | 0.0 | 0.0 |
| 2025 | 647.7 | 488.9 | 0.2 | 0.0 | 0.0 | 0.0 | 0.0 | 0.0 |
| 2026 | 432.2 | 0.0 | 266.6 | 138.7 | 3.7 | 10.4 | 5.5 | 7.3 |
| 2027 | 23.5 | 0.0 | 0.0 | 0.2 | 0.0 | 10.4 | 5.5 | 7.3 |
| 2028 | 408.8 | 0.0 | 266.6 | 138.5 | 3.7 | 0.0 | 0.0 | 0.0 |
| 2029 | 0.4 | 0.0 | 0.0 | 0.0 | 0.0 | 0.0 | 0.0 | 0.0 |
| 2030 | 0.5 | 0.0 | 0.0 | 0.0 | 0.0 | 0.0 | 0.0 | 0.0 |
| 2031 | 33.6 | 26.1 | 0.0 | 0.0 | 0.0 | 0.0 | 0.0 | 0.0 |
| 2032 | 409.2 | 0.0 | 268.6 | 140.6 | 0.0 | 0.0 | 0.0 | 0.0 |
| 2033 | 266.0 | 0.0 | 265.9 | 0.0 | 0.1 | 0.0 | 0.0 | 0.0 |
| 2034 | 143.2 | 0.0 | 2.7 | 140.5 | 0.0 | 0.0 | 0.0 | 0.0 |
| 2035 | 16.2 | 0.0 | 0.0 | 0.2 | 0.0 | 10.4 | 5.5 | 0.1 |
| 2036 | 7.2 | 0.0 | 0.0 | 0.0 | 0.0 | 0.0 | 0.0 | 7.2 |
| 2037 | 1508.6 | 0.0 | 0.0 | 0.0 | 0.0 | 1508.6 | 0.0 | 0.0 |
| 2038 | 427.3 | 0.0 | 0.0 | 0.0 | 0.0 | 427.3 | 0.0 | 0.0 |
| 2039 | 1935.9 | 0.0 | 0.0 | 0.0 | 0.0 | 1935.9 | 0.0 | 0.0 |
| 2040 | 130.1 | 0.0 | 0.0 | 0.0 | 0.0 | 130.1 | 0.0 | 0.0 |
| 2041 | 2066.0 | 0.0 | 0.0 | 0.0 | 0.0 | 2066.0 | 0.0 | 0.0 |
| 2042 | 326.9 | 0.0 | 326.9 | 0.0 | 0.0 | 0.0 | 0.0 | 0.0 |
| 2043 | 524.8 | 0.0 | 524.8 | 0.0 | 0.0 | 0.0 | 0.0 | 0.0 |
| 2044 | 851.7 | 0.0 | 851.7 | 0.0 | 0.0 | 0.0 | 0.0 | 0.0 |
| 2045 | 300.4 | 0.0 | 300.4 | 0.0 | 0.0 | 0.0 | 0.0 | 0.0 |
| 2046 | 1152.1 | 0.0 | 1152.1 | 0.0 | 0.0 | 0.0 | 0.0 | 0.0 |

| Stream # | $H_2O$ | Hydrogen | Argon | Nitrogen | Oxygen | CO | $CO_2$ |
|---|---|---|---|---|---|---|---|
| 2001 | 0.0 | 0.0 | 0.0 | 0.0 | 0.0 | 0.0 | 0.0 |
| 2002 | 58.7 | 16.2 | 46.6 | 249.9 | 0.0 | 0.0 | 0.0 |
| 2003 | 123.1 | 2.0 | 46.6 | 249.9 | 0.0 | 0.0 | 19.2 |
| 2004 | 620.0 | 37.6 | 47.7 | 252.9 | 0.0 | 93.6 | 493.5 |
| 2005 | 0.0 | 0.0 | 1.1 | 3.0 | 839.6 | 0.0 | 0.0 |
| 2006 | 0.0 | 0.0 | 0.0 | 0.0 | 0.0 | 0.0 | 0.0 |
| 2007 | 39.0 | 37.7 | 47.7 | 252.9 | 0.0 | 93.6 | 493.9 |
| 2008 | 581.0 | 0.0 | 0.0 | 0.0 | 0.0 | 0.0 | 0.0 |
| 2009 | 12.9 | 37.7 | 47.7 | 252.9 | 0.0 | 93.6 | 493.9 |

TABLE 1-continued

| | | Stream flow rates | | | | | |
|---|---|---|---|---|---|---|---|
| 2010 | 27.5 | 0.0 | 0.0 | 0.0 | 0.0 | 0.0 | 0.0 |
| 2011 | 7.9 | 38.2 | 47.7 | 256.6 | 0.0 | 93.6 | 509.6 |
| 2012 | 5.1 | 0.0 | 0.0 | 0.0 | 0.0 | 0.0 | 0.0 |
| 2013 | 0.0 | 0.0 | 0.0 | 3.7 | 0.0 | 0.0 | 15.7 |
| 2014 | 0.0 | 0.5 | 0.0 | 3.7 | 0.0 | 0.0 | 15.7 |
| 2015 | 1.2 | 0.5 | 0.0 | 3.7 | 0.0 | 0.0 | 15.7 |
| 2016 | 7.9 | 38.2 | 47.7 | 256.6 | 0.0 | 93.6 | 0.0 |
| 2017 | 1.3 | 0.0 | 0.0 | 0.0 | 0.0 | 0.0 | 96.4 |
| 2018 | 12.1 | 0.0 | 0.0 | 0.0 | 0.0 | 0.0 | 412.4 |
| 2019 | 0.0 | 38.2 | 47.7 | 256.6 | 0.0 | 93.6 | 0.0 |
| 2020 | 0.0 | 1.1 | 6.7 | 0.0 | 2.4 | 0.0 | 35.2 |
| 2021 | 0.0 | 36.0 | 46.6 | 249.9 | 0.0 | 91.3 | 0.0 |
| 2022 | 0.0 | 1.0 | 0.8 | 4.9 | 0.0 | 1.8 | 0.0 |
| 2023 | 6.1 | 0.0 | 0.0 | 0.0 | 0.0 | 0.0 | 0.0 |
| 2024 | 0.0 | 20.2 | 32.8 | 163.8 | 0.0 | 60.8 | 0.0 |
| 2025 | 0.0 | 18.1 | 14.9 | 92.8 | 0.0 | 32.9 | 0.0 |
| 2026 | 0.0 | 0.0 | 0.0 | 0.0 | 0.0 | 0.0 | 0.0 |
| 2027 | 0.0 | 0.0 | 0.0 | 0.0 | 0.0 | 0.0 | 0.0 |
| 2028 | 0.0 | 0.0 | 0.0 | 0.0 | 0.0 | 0.0 | 0.0 |
| 2029 | 0.0 | 0.4 | 0.0 | 0.0 | 0.0 | 0.0 | 0.0 |
| 2030 | 0.0 | 0.5 | 0.0 | 0.0 | 0.0 | 0.0 | 0.0 |
| 2031 | 0.0 | 0.0 | 0.8 | 4.9 | 0.0 | 1.8 | 0.0 |
| 2032 | 0.0 | 0.0 | 0.0 | 0.0 | 0.0 | 0.0 | 0.0 |
| 2033 | 0.0 | 0.0 | 0.0 | 0.0 | 0.0 | 0.0 | 0.0 |
| 2034 | 0.0 | 0.0 | 0.0 | 0.0 | 0.0 | 0.0 | 0.0 |
| 2035 | 0.0 | 0.0 | 0.0 | 0.0 | 0.0 | 0.0 | 0.0 |
| 2036 | 0.0 | 0.0 | 0.0 | 0.0 | 0.0 | 0.0 | 0.0 |
| 2037 | 0.0 | 0.0 | 0.0 | 0.0 | 0.0 | 0.0 | 0.0 |
| 2038 | 0.0 | 0.0 | 0.0 | 0.0 | 0.0 | 0.0 | 0.0 |
| 2039 | 0.0 | 0.0 | 0.0 | 0.0 | 0.0 | 0.0 | 0.0 |
| 2040 | 0.0 | 0.0 | 0.0 | 0.0 | 0.0 | 0.0 | 0.0 |
| 2041 | 0.0 | 0.0 | 0.0 | 0.0 | 0.0 | 0.0 | 0.0 |
| 2042 | 0.0 | 0.0 | 0.0 | 0.0 | 0.0 | 0.0 | 0.0 |
| 2043 | 0.0 | 0.0 | 0.0 | 0.0 | 0.0 | 0.0 | 0.0 |
| 2044 | 0.0 | 0.0 | 0.0 | 0.0 | 0.0 | 0.0 | 0.0 |
| 2045 | 0.0 | 0.0 | 0.0 | 0.0 | 0.0 | 0.0 | 0.0 |
| 2046 | 0.0 | 0.0 | 0.0 | 0.0 | 0.0 | 0.0 | 0.0 |

Table 2 shows the temperatures for select streams of the example process. Stream numbers correspond to those of Examples 4-7 and FIGS. 26-31.

TABLE 2

| Stream temperatures | |
|---|---|
| Stream # | Temperature (° F.) |
| 2001 | 100 |
| 2002 | 100 |
| 2003 | 1000 |
| 2004 | 1528 |
| 2005 | 95 |
| 2006 | 1022 |
| 2007 | 100 |
| 2008 | 100 |
| 2009 | 100 |
| 2010 | 100 |
| 2011 | 100 |
| 2012 | 100 |
| 2013 | 100 |
| 2014 | 500 |
| 2015 | 501 |
| 2016 | 102 |
| 2017 | 100 |
| 2018 | 100 |
| 2019 | 55 |
| 2020 | 43 |
| 2021 | 43 |
| 2022 | 40 |
| 2023 | 55 |
| 2024 | −30 |
| 2025 | 15 |
| 2026 | −33 |
| 2027 | 145 |
| 2028 | −17 |
| 2029 | 100 |
| 2030 | 100 |
| 2031 | 100 |
| 2032 | −9 |
| 2033 | 100 |
| 2034 | −33 |
| 2035 | 126 |
| 2036 | 100 |
| 2937 | −52 |
| 2938 | −7 |
| 2039 | 139 |
| 2040 | 59 |
| 2041 | 192 |
| 2042 | −154 |
| 2043 | −120 |
| 2044 | −22 |
| 2045 | −94 |
| 2046 | 83 |

Example 9: Equipment, Materials of Construction and Utilities

The material of construction for the different process units shown in FIGS. 26-31 is tabulated in the major equipment list (Tables 3-8). Carbon steel material can be used for construction of at least some or most of the process equipment as the reaction medium is not corrosive. The distillation column shell and, heat exchanger shells can be constructed out of carbon steel (C.S.) or stainless steel (SS). Distillation column internals are made of stainless steel whereas the reactor shells are constructed of carbon steel. The Transfer Line Exchangers used for high pressure steam are made of Mo-Alloy steel.

The process gas compression and treatment section has two pumps and two spares operating at 516 BHP, the product separation and recovery section has four pumps and four spares operating at 1714 BHP, the refrigeration section has one pump and one spare operating at 128 BHP.

TABLE 3

Reactors and materials of construction

| Name | Number | Size | Material of Construction | Remarks |
|---|---|---|---|---|
| OCM reactor Stage-I | 111-R101 | 19 ft. dia | shell: C.S. | 2 sieve trays, 24 inch spacing |
| | | 15 ft. T-T | trays: 304 SS | Reactor Bed: H = 8.3 ft., D = 17 ft.; 12" refractory lining |
| OCM reactor Stage-II | 111-R102 | 19 ft. dia | shell: C.S. | 4 sieve trays, 24 inch spacing |
| | | 22 ft. T-T | trays: 304 SS | Reactor Bed: H = 8.3 ft., D = 17 ft.; 12" refractory lining, Post Bed Cracking bed height = 7 ft |
| Methanation Stage-I | 111-R103 | 18 ft. dia | shell: C.S. | 2 sieve trays, 24 inch spacing |
| | | 20 ft. T-T | trays: 304 SS | Reactor bed: H = 15 ft. |
| Methanation Stage-II | 111-R104 | 18 ft. dia | shell: C.S. | 2 sieve trays, 24 inch spacing |
| | | 20 ft. T-T | trays: 304 SS | Reactor bed: H = 15 ft. |
| NG desulfurization | 180-D802A | 13 ft. dia | shell: C.S. | 4 sieve trays, 24 inch spacing |
| | | 38 ft. T-T | trays: 304 SS | Top reaction bed: H = 6.4 ft. Bottom zinc oxide filter bed: H = 26 ft. |
| Acetylene hydrogenation reactor | 171-R711 | 12 ft. dia | shell: C.S. | 2 sieve trays, 24 inch spacing |
| | | 20 ft. T-T | trays: 304 SS | Reactor bed: H = 15 ft. |

TABLE 4

Columns and materials of construction

| Name | Number | Size | Material of Construction | Remarks |
|---|---|---|---|---|
| Process Gas Quench tower-I | 111-D109 | 32 ft. dia | shell: C.S. | 10 sieve trays, 12 inch spacing |
| | | 40 ft. | trays: 304 SS | |
| Process Gas Quench tower-II | 120-D202 | 25 ft. dia | shell: C.S. | 10 sieve trays, 12 inch spacing |
| | | 35 ft. | trays: 304 SS | |
| Process Gas Quench tower-III | 120-D203 | 20 ft. dia | shell: C.S. | 10 sieve trays, 12 inch spacing |
| | | 30 ft. | trays: 304 SS | |
| Demethanizer | 150-T501 | 18 ft. dia | shell: S.S. | 60 valve trays, 24 inch spacing |
| | | 155 ft. | trays: 304 SS | Top section: D = 18 ft., H = 35 ft., 15 trays; Bottom section: D = 12 ft., H = 120 ft., 45 trays |
| Deethanizer | 170-T701 | 11 ft. dia | shell: S.S. | 40 sieve trays, 12 inch spacing |
| | | 60 ft. | trays: 304 SS | |
| $C_2$ splitter | 160-T601 | 20 ft. dia | shell: C.S. | 110 sieve trays, 12 inch spacing |
| | | 140 ft. | trays: 304 SS | |
| Depropanizer | 190-T801 | 3.5 ft. dia | shell: C.S. | 20 valve trays, 24 inch spacing |
| | | 50 ft. | trays: 304 SS | |

TABLE 5

Compressors and materials of construction

| Name | Number | Size | Remarks |
|---|---|---|---|
| Process Gas compressor Stage-I | 120-C202/C203 | 63,500 bhp (EACH) | STEAM turbine |

TABLE 5-continued

Compressors and materials of construction

| Name | Number | Size | Remarks |
|---|---|---|---|
| Process Gas compressor Stage-II | 120-C204 | 68,930 bhp | STEAM turbine |
| PSA feed compressor | 172-C721 | 4,700 bhp | electric motor |
| Ethylene Product Compressor | 160-C601 | 29,390 bhp | 3-stage compressor; steam turbine |
| Propylene Compressor | 175-C751 | 58,500 bhp | 3 stage compressor; steam turbine |
| Ethylene Compressor | 176-C761 | 30,360 bhp | Includes 3-stage compressor with intercoolers; steam turbine |

All of the compressors in Table 5 are constructed from carbon steel.

TABLE 6

Heat exchangers and materials of construction

| Name | Number | Size | Material of Construction | Comments |
|---|---|---|---|---|
| Methane recycle heater-I | 111-E101 | 47,300 sq. ft. | shell: C.S. | |
| | | 252.3 MMBtu/hr | tubes: C.S. | |
| Methanation product heater | 111-E102 | 109,720 sq. ft. (EACH) | shell: C.S. | |
| | | 1,083 MMBtu/hr | tubes: C.S. | |
| OCM-I product cooler-I | 111-E103A/B | 16,200 sq. ft. (EACH) | shell: Mo alloy steel | Transfer Line Exchanger; generates 1500 psia steam |
| | | 1,330 MMBtu/hr | tubes: Mo alloy steel | |
| OCM-I product cooler-II | 111-E103C | 24,500 sq. ft. | shell: C.S. | Superheats 1500 psia steam to 890° F. |
| | | 443.5 MMBtu/hr | tubes: C.S. | |
| OCM-II product cooler-I | 111-E104A/B | 21,900 sq. ft. (EACH) | shell: Mo alloy steel | Transfer Line Exchanger; generates 1500 psia steam |
| | | 995 MMBtu/hr | tubes: Mo alloy steel | |
| OCM-II product cooler-II | 111-E104C | 15,990 sq. ft. | shell: C.S. | Superheats 1500 psia steam to 890° F |
| | | 324.4 MMBtu/hr | tubes: C.S. | |
| Ethane recycle heater | 111-E105 | 20,700 sq. ft. | shell: C.S. | |
| | | 163.6 MMBtu/hr | tubes: C.S. | |
| OCM-II product cooler-III | 111-E106 | 37,325 sq. ft. (EACH) | shell: C.S. | |
| | | 531.8 MMBtu/hr | tubes: C.S. | |
| OCM-II product cooler-IV | 111-E107 | 42,450 sq. ft. | shell: C.S. | |
| | | 271 MMBtu/hr | tubes: C.S. | |
| Methane recycle heater-II | 111-E108 | 42,480 sq. ft. (EACH) | shell: C.S. | |
| | | 297.9 MMBtu/hr | tubes: C.S. | |
| Quench tower-I cooler | 111-E109 | 40,700 sq. ft. (EACH) | shell: C.S. | Plate and frame exchanger |
| | | 609.9 MMBtu/hr | tubes: 304 SS | |
| NG feed heater-I | HRSG Coil | 35,100 sq. ft. | shell: C.S. | |
| | | 132.4 MMBtu/hr | tubes: C.S. | |
| Quench tower-II cooler | 120-D202 | 52,750 sq. ft. | shell: C.S. | Plate and frame exchanger |
| | | 292.3 MMBtu/hr | tubes: 304 SS | |
| Quench tower-III cooler | 120-D203 | 57,530 sq. ft. | shell: C.S. | Plate and frame exchanger |
| | | 267.7 MMBtu/hr | tubes: 304 SS | |
| $CO_2$ lean gas cooler-I | 145-E301 | 18,250 sq. ft. | shell: C.S. | |
| | | 81.67 MMBtu/hr | tubes: C.S. | |

TABLE 6-continued

Heat exchangers and materials of construction

| Name | Number | Size | Material of Construction | Comments |
|------|--------|------|--------------------------|----------|
| $CO_2$ lean gas cooler-II | 145-E302 | 8,500 sq. ft. 9.27 MMBtu/hr | shell: C.S. tubes: C.S. | |
| Demethanizer feed cooler | 150-E501 | | shell: Low temp C.S. tubes: low temp C.S. | Custom cold box, Weight: 44,300 lbs; W: 4.5 ft., H: 5.8 ft. and L: 22 ft. |
| Acetylene reactor feed heater | 171-E711 | 30,970 sq. ft. 21.44 MMBtu/hr | shell: C.S. tubes: C.S. | |
| Acetylene reactor prod cooler | 171-E712 | 4,230 sq. ft. 9.29 MMBtu/hr | shell: C.S. tubes: 304 SS | |
| Deetha OVHD condenser | 170-E701 | 22,820 sq. ft. 30.7 MMBtu/hr | shell: C.S. tubes: 304 SS | |
| Deethanizer reboiler | 170-E702 | 7,900 sq. ft. 73.6 MMBtu/hr | shell: C.S. tubes: C.S. | |
| $C_2$ splitter cold box | 160-E601/603 | | shell: C.S. tubes: C.S. | Includes $C_2$ splitter condenser and reboiler; Weight: 57,465 lbs ; W: 4.5 ft., H: 6 ft. and l: 27.6 ft. |
| Depropanizer OVHD condenser | 190-E801 | 3,350 sq. ft. 3.85 MMBtu/hr | shell: C.S. tubes: 304 SS | |
| Depropanizer reboiler | 190-E802 | 2,280 sq. ft. 5.97 MMBtu/hr | shell: C.S. tubes: C.S. | |
| $C_{4+}$ product cooler | 190-E803 | 350 sq. ft. 0.7 MMBtu/hr | shell: C.S. tubes: C.S. | |
| Propylene cooler | 175-E751 | 48,275 sq. ft. (EACH) 363.6 MMBtu/hr | shell: C.S. tubes: 304 SS | |
| Ethylene cooler | 178-E781 | 49,030 sq. ft. 240.9 MMBtu/hr | shell: C.S. tubes: 304 SS | |

TABLE 7

Tanks and materials of construction (stainless steel shell for demethanizer and deethanizer

| Name | Number | Size |
|------|--------|------|
| 50% Caustic Storage | 900-T901 | 95,000 gal |
| Spent Caustic Holdup | 900-T902 | 115,000 gal |
| Amine Dump Tank | 900-T903 | 150,000 gal |
| Amine Make-up storage | 900-T904 | 4,000 gal |
| $C_{4+}$ product storage | 900-T905 | 35,000 gal |

TABLE 8

Pressure vessels and materials of construction (stainless steel shell for demethanizer and deethanizer

| Name | Number | Size |
|------|--------|------|
| NG feed KO drum | 180-D801 | 4,030 gal |
| Process Gas KO drum | 145-D301 | 33,089 gal |
| Deethanizer reflux drum | 170-D701 | 11,037 gal |
| Depropanizer reflux drum | 190-D801 | 476 gal |
| Propylene collection drum | 175-D754 | 39,657 gal |
| Propylene Flash Drum-I | 175-D751 | 47,000 gal |
| Propylene Flash Drum-II | 175-D752 | 19,829 gal |
| Propylene Flash drum-III | 175-D753 | 91,800 gal |
| Ethylene collection drum | 176-D764 | 23,460 gal |
| Ethylene Flash drum-I | 176-D761 | 20,305 gal |
| Ethylene Flash drum-II | 176-D762 | 15,640 gal |
| Ethylene Flash drum-III | 176-D763 | 28,865 gal |

In addition, the process has: a natural gas heater (F-201) 2673 sized 35 MMBTU/HR made of carbon steel; three process gas driers (M-201 A-C) 2669 each having a capacity of 34,300 gallons made of carbon steel and having molecular sieve beds including all peripheral equipment and one spare column; a treated natural gas expander (S-201) 2674 of 4200 HP and made of carbon steel; a $CO_2$ removal unit (G-201) 2668 made of carbon steel and sized to 11.5 MMSCFD $CO_2$ including an amine scrubber, regeneration, caustic scrubber and peripheral units; a recycle split vapor (RSV) unit (G-301) 2680 made of carbon steel and including a cold box (Width: 4 ft., Height: 5.8 ft. and Length: 14.2 ft.), a compressor, two turboexpanders, and two knockout drums; and a $H_2$ pressure swing adsorption unit (G-302) 2686 made of carbon steel and having a size of 4.36 MMSCFD.

The utilities consumed by the process shown in FIGS. 26-31 are tabulated in Tables 9-10). Table 9 shows the average consumption of the utilities and Table 10 shows peak demands imposed upon the utilities. The utilities are scaled to be able to satisfy both average demands and peak demands.

TABLE 9

Average utility consumption

|  | Units | Battery Limits Total | OCM Reaction System | Compression & Treatment System | Separation and Recovery System | Refrigeration Section |
| --- | --- | --- | --- | --- | --- | --- |
| Cooling Water | gpm | 244,172 | 61,088 | 145,346 | 1,317 | 36,421 |
| Natural Gas | MM Btu/hr | 47 | N/A | 47 | N/A | N/A |
| Steam, 150 psig | M lb/hr | 1,030 | N/A | 1,030 | N/A | N/A |
| Steam, 860 psig | M lb/hr | 1,726 | N/A | N/A | 625 | 1,101 |
| Steam, 1500 psig | M lb/hr | 2,963 | N/A | 2,920 | 43 | — |
| Steam, 150 psig | M lb/hr | −1,225 | N/A | N/A | −625 | −600 |
| Steam, 860 psig | M lb/hr | −1,977 | N/A | −1,977 | N/A | N/A |
| Steam, 1500 psig | M lb/hr | −2,963 | −2,963 | N/A | N/A | N/A |

TABLE 10

Peak utility consumption

|  | Units | Battery Limits Total | OCM Reaction System | Compression & Treatment System | Separation and Recovery System | Refrigeration Section |
| --- | --- | --- | --- | --- | --- | --- |
| Cooling Water | gpm | 293,007 | 73,306 | 174,416 | 1,580 | 43,705 |
| Electricity | kW | −6,668 | N/A | 4,428 | −11,202 | 106 |
| Steam, 150 psig | M lb/hr | 1,236 | — | 1,236 | N/A | N/A |
| Steam, 860 psig | M lb/hr | 2,071 | — | N/A | 750 | 1,321 |
| Steam, 1500 psig | M lb/hr | 3,556 | — | 3,504 | 52 | N/A |

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for producing hydrocarbon compounds including two or more carbon atoms ($C_{2+}$ compounds), the method comprising:
   (a) performing an oxidative coupling of methane (OCM) reaction in an OCM reactor to produce an OCM effluent stream comprising carbon dioxide ($CO_2$), carbon monoxide (CO), hydrogen ($H_2$), one or more $C_{2+}$ compounds, and methane ($CH_4$);
   (b) separating the OCM effluent stream into a first stream comprising at least some of the one or more $C_{2+}$ compounds and a second stream comprising carbon monoxide (CO), $CO_2$, $H_2$, and $CH_4$;
   (c) directing a first portion of the second stream and an air stream to a gas compressor, and burning the first portion of the second stream to compress the air stream to produce a compressed air stream;
   (d) separating the compressed air stream in an air separation unit (ASU) into a third stream comprising $O_2$ and a fourth stream comprising $N_2$; and
   (e) feeding the third stream to the OCM reactor.

2. The method according to claim 1, further comprising:
   methanating a second portion of the second stream to produce a methanated stream comprising $CH_4$ formed from the $H_2$ and CO and/or $CO_2$ in the second portion of the second stream; and
   directing a first portion of the methanated stream to the OCM reactor.

3. The method according to claim 2, further comprising directing a second portion of the methanated stream into a natural gas pipeline.

4. The method according to claim 1, further comprising:
   directing the OCM effluent stream to a heat recovery steam generator (HRSG) system; and
   with the HRSG system, transferring heat from the OCM effluent stream to a water stream to produce steam.

5. The method according to claim 1, further comprising:
   transferring heat from the OCM effluent stream in a first heat exchanger, thereby cooling the OCM effluent stream;
   wherein step (b) comprises demethanizing the OCM effluent in a demethanizer to produce the first stream and the second stream;
   compressing a second portion of the second stream, thereby heating the second portion of the second stream, and subsequently in a second heat exchanger transferring heat from the second portion of the second stream, thereby cooling the second portion of the second stream;
   separating the second portion of the second stream in a phase separation unit to produce a liquid stream and a vapor stream; and transferring heat from the liquid stream in a third heat exchanger and subsequently directing the liquid stream into the demethanizer.

6. The method according to claim 5, further comprising:
expanding the vapor stream, thereby cooling the vapor stream; and
transferring heat to the vapor stream in the third heat exchanger, the second heat exchanger, and/or the first heat exchangers, thereby heating the vapor stream.

7. The method according to claim 5, further comprising:
expanding a third portion of the second stream, thereby cooling the third portion of the second stream; and
transferring heat to the third portion of the second stream in the third heat exchanger, the second heat exchanger, and/or the first heat exchanger, thereby heating the third portion of the second stream.

8. The method according to claim 1, further comprising:
transferring heat from the OCM effluent stream in a first heat exchanger, thereby cooling the OCM effluent stream;
wherein step (b) comprises demethanizing the OCM effluent in a demethanizer to produce the first stream and the second stream;
compressing a second portion of the second stream, thereby heating the second portion of the second stream, and subsequently transferring heat from the second portion of the second stream in a second heat exchanger, thereby cooling the second portion of the second stream;
separating the second portion of the second stream in a first phase separation unit to produce a first liquid stream and a first vapor stream;
expanding the first vapor stream, thereby cooling the first vapor stream and subsequently transferring heat to the first vapor stream in the second heat exchanger and/or the first heat exchanger, thereby heating the first vapor stream;
sub-cooling and flashing the first liquid stream to produce a two-phase stream;
separating the two-phase stream in a second phase separation unit to produce a second liquid stream and a second vapor stream; and
directing the second liquid stream into the demethanizer.

9. The method according to claim 1, further comprising:
transferring heat from the OCM effluent stream in a first heat exchanger and a second heat exchanger downstream of the first heat exchanger with respect to a flow direction of the OCM effluent stream, thereby cooling the OCM effluent stream;
wherein step (b) comprises demethanizing the OCM effluent in a demethanizer to produce the first stream and the second stream;
expanding a second portion of the second stream, thereby cooling the second portion of the second stream;
transferring heat to the second portion of the second stream in the second heat exchanger and the first heat exchanger downstream of the second heat exchanger with respect to a flow direction of the second portion of the second stream, thereby heating the second portion of the second stream; and
feeding the second portion of the second stream from the first heat exchanger into the OCM reactor.

10. The method according to claim 1, further comprising:
transferring heat from the OCM effluent stream in a first heat exchanger and subsequently expanding the OCM effluent stream, thereby cooling the OCM effluent stream;
wherein step (b) comprises demethanizing the OCM effluent in a demethanizer to produce the first stream and the second stream;
transferring heat to a second portion of the second stream in a second heat exchanger and the first heat exchanger downstream of the second heat exchanger with respect to a flow direction of the second portion of the second stream, thereby heating the second portion of the second stream;
compressing a third portion of the second stream and, in a phase separation unit, separating the third portion of the second stream into a liquid stream and a vapor stream; and
directing the liquid stream through the second heat exchanger and into the demethanizer.

11. The method according to claim 10, further comprising expanding the vapor stream to cool the vapor stream.

12. The method according to claim 10, further comprising transferring heat to the vapor stream in the second heat exchanger and the first heat exchanger.

13. The method according to claim 1, wherein the OCM reaction generates heat, and wherein the method further comprises generating electrical power from said heat.

14. The method according to claim 13, wherein said heat is converted to steam and said steam is converted to power in a steam turbine.

15. An oxidative coupling of methane (OCM) system for producing olefins comprising:
(a) an OCM subsystem that (i) takes as input a feed stream comprising methane ($CH_4$) and a feed stream comprising an oxidizing agent, and (ii) generates a product stream comprising $C_{2+}$ compounds and non-$C_{2+}$ impurities from the $CH_4$ and the oxidizing agent in at least one OCM reactor comprised in the OCM subsystem;
(b) a separation subsystem fluidically coupled to the OCM subsystem that separates the product stream into (i) a first stream comprising $C_{2+}$ compounds and (ii) a second stream comprising carbon monoxide (CO) hydrogen ($H_2$), carbon dioxide ($CO_2$), and $CH_4$; and
(c) an air separation unit (ASU) housing a gas turbine combined cycle (GTCC) unit fluidically coupled to the separation subsystem and to the OCM subsystem, wherein the GTCC unit is configured to accept a first portion of the second stream to burn as fuel for driving a compressor that provides compressed air to the ASU, and wherein the ASU is configured to separate the compressed air into an oxygen ($O_2$) stream and a nitrogen ($N_2$) stream and to direct the $O_2$ stream to the OCM subsystem.

16. The system according to claim 15, further comprising a methanation subsystem fluidically coupled to the separation subsystem and to the OCM subsystem, wherein the methanation subsystem is configured to convert $H_2$ and $CO_2$ and/or CO into $CH_4$ from a second portion of the second stream.

17. The system according to claim 16, further comprising a heat recovery steam generator (HRSG) system fluidically and/or thermally coupled to the OCM subsystem, wherein the HRSG system is configured to transfer heat from the product stream to a water stream to produce steam.

18. The system according to claim 15, wherein the OCM subsystem comprises at least one post-bed cracking unit within said at least one OCM reactor or downstream of said at least one OCM reactor, wherein the post-bed cracking unit is configured to convert at least a portion of alkanes in the product stream to alkenes.

* * * * *